| United States Patent [19] | [11] Patent Number: 5,041,458 |
|---|---|
| Basarab | [45] Date of Patent: Aug. 20, 1991 |

[54] FUNGICIDAL AMINOTRIAZOLES AND AMINOIMIDAZOLES

[75] Inventor: Gregory S. Basarab, Wilmington, Del.

[73] Assignee: E. I. Du Pont de Nemours and Company, Wilmington, Del.

[21] Appl. No.: 435,492

[22] Filed: Sep. 5, 1989

Related U.S. Application Data

[63] Continuation-in-part of Ser. No. 28,389, Mar. 2, 1987, abandoned.

[51] Int. Cl.$^5$ .................. A01N 43/653; C07D 249/08
[52] U.S. Cl. .................................. 514/383; 514/236.2; 514/235.5; 514/256; 514/269; 514/274; 514/333; 514/340; 514/384; 548/263.8; 548/264.8; 544/124; 544/132; 544/298; 544/316; 544/319; 544/333; 546/256; 546/276; 546/275

[58] Field of Search ............................ 548/264.8, 263.8; 514/383, 384, 340, 333, 256, 269, 274, 236.2, 235.5; 546/256, 276; 544/333, 298, 316, 319, 124, 132

[56] References Cited

U.S. PATENT DOCUMENTS 3,444,162 5/1969 Hyatt ................................ 548/264.8
3,577,553 5/1971 Ferlanto ............................. 514/383

FOREIGN PATENT DOCUMENTS 1019120 2/1966 United Kingdom ................ 548/266

Primary Examiner—Mary C. Lee
Assistant Examiner—Patricia L. Morris
Attorney, Agent, or Firm—John A. Parrish

[57] ABSTRACT

Substituted N-aminotriazoles and N-aminoimidazoles having selected substituents on the amino group and azole rings, agriculturally useful composition comprising such compounds and the use of such compounds as fungicides.

39 Claims, No Drawings

FUNGICIDAL AMINOTRIAZOLES AND AMINOIMIDAZOLES

CROSS-REFERENCE TO RELATED APPLICATIONS

This application is the national phase of PCT/US88/00726 filed Mar. 15, 1988, which in turn is a continuation-in-part of U.S. Ser. No. 028,389 filed on Mar. 2, 1987 now abandoned.

BACKGROUND OF THE INVENTION

U.S. Pat. No. 4,366,165 (Belgian Patent 867,245) discloses fungicides of the formula

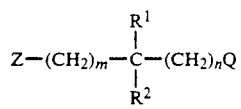

where
Z is a $C_6$ to $C_{10}$ aryl radical;
$R^1$ (in part) is CN, $C_1$ to $C_{12}$ alkyl or $C_3$ to $C_8$ cycloalkyl;
$R^2$ (in part) is H, $C_1$ to $C_{12}$ alkyl, or $C_3$ to $C_8$ cycloalkyl;
m is 0 or 1;
n is 0 or 2; and
Q is a 1-(1,2,4-triazolyl) or 4-(1,2,4-triazolyl) radical.

European Patent 175,651, published Mar. 27, 1986 discloses microbiocides of the formula

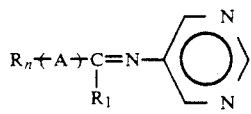

wherein
A is phenyl, naphthyl, biphenyl, phenoxyphenyl or phenylthiophenyl;
R (in part) is halogen, CN, $NO_2$ or $C_1$ to $C_4$ alkyl; and
$R_1$ is one of $OR_2$, $SR_2$, $N(R_3)(R_4)$.

L. Zirngibl, in *Prog. Drug Res.*, 27 (1983), 253–383 reviews the field of antifungal monocyclic 1-substituted-1H-azoles.

None of the above suggests an imidazole or triazole linked from a nitrogen in the heterocycle to an external nitrogen atom.

SUMMARY OF THE INVENTION

This invention pertains to N-aminotriazoles, N-aminoimidazoles and their derivatives of Formula I.

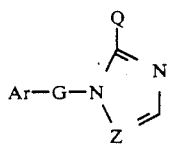

to agriculturally suitable compositions containing them and their use as fungicides.

In the formula:
Ar is phenyl, pyridyl or thienyl each substituted with 1–3 substituents selected from $R_5$, $R_6$ and $R_7$;
Z is CH or N;
Q is H, $S(O)_nR^{18}$, halogen, CHO, $C_1$-$C_4$ alkyl, or SH and its corresponding disulfide;
n is 0, 1 or 2;
G is

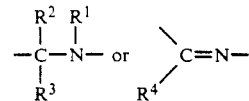

where the nitrogen is bonded to the triazole or imidazole heterocycle;

$R^1$ is H, $C_1$ to $C_6$ alkyl, $C_1$ to $C_4$ haloalkyl, ($C_3$ to $C_6$ cycloalkyl)methyl, $C_3$ to $C_6$ cycloalkyl, $CH_2CO_2R^{10}$, ($C_2$ to $C_4$ alkenyl)methyl, ($C_2$ to $C_4$ haloalkenyl)methyl, $CH_2SCH_3$, $CH_2OCH$, ($C_2$ to $C_4$ alkynyl)methyl, $C(O)R^{12}$, $C(O)(C_1$ to $C_4$ haloalkyl), CHO, $C(O)NH_2$, $C(O)NHR^{12}$, phenyl or benzyl each optionally substituted with $NO_2$, CN or 1 to 3 halogens;

$R^2$ is H, $C_2$ to $C_4$ alkyl, $C_1$ to $C_4$ haloalkyl, cyclopropyl, $CH_2CN$, $CO_2R^{11}$, CHO, $CH_2OH$, CN, $C_2$ to $C_4$ alkenyl or $C_2$ to $C_4$ alkynyl;

$R^3$ is pyridylmethyl, thienylmethyl, phenylmethyl, benzylmethyl, phenoxymethyl or thiophenoxymethyl each substituted with $R^8$ and $R^9$ on the aromatic radical and with $R^{16}$ and $R^{17}$ on the aliphatic carbon, phenyl substituted with $R^8$ and $R^9$, $C_1$ to $C_4$ alkyl, $C_1$ to $C_4$ haloalkyl, $C_3$ to $C_6$ cycloalkyl, thienyl optionally substituted with 1 to 2 halogen, styryl substituted with $R^8$ and $R^9$, ($C_3$ to $C_6$ cycloalkyl)methyl, ($C_3$ to $C_6$ cycloalkyl)ethyl, pyrimidine or pyridine each substituted with $R^8$ and $R^9$;

$R^4$ is phenyl substituted with $R^8$ and $R^9$, benzyl substituted with $R^8$ and $R^9$, $C_3$ to $C_6$ cycloalkyl, thienyl optionally substituted with 1 to 2 halogen, styryl substituted with $R^8$ and $R^9$, pyridine or pyrimidine each substituted with $R^8$ and $R^9$, ($C_3$ to $C_6$ cycloalkyl)methyl, ($C_3$ to $C_6$ cycloalkyl)ethyl, $OR^{13}$, $SR^{13}$, or $N(R^{14})(R^{15})$;

$R^5$ is H or halogen;
$R^6$ is H, halogen, methyl, $CF_3$ or $OCH_3$;
$R^7$ is H, halogen, $C_1$ to $C_4$ alkyl, $C_1$ to $C_4$ haloalkyl, $C_1$ to $C_2$ alkoxy, CN, $CO_2R^{12}$, $NO_2$, $S(O)_mCH_3$, phenyl optionally substituted with 1 to 3 halogens, or phenoxy optionally substituted with 1 to 3 halogen;
m is 0, 1 or 2;
$R^8$ is H or halogen;
$R^9$ is H, halogen, methyl, $CF_3$, $OCH_3$, CN or $CO_2R^{12}$;
$R^{10}$ is H, $C_1$ to $C_6$ alkyl, benzyl optionally substituted with 1 to 3 halogen, or phenyl optionally substituted with 1 to 3 halogen;
$R^{11}$ is H or $C_1$ to $C_3$ alkyl;
$R^{12}$ is $C_1$ to $C_4$ alkyl;
$R^{13}$ is $C_1$ to $C_5$ alkyl, ($C_2$ to $C_4$ alkenyl)methyl, ($C_2$ to $C_4$ alkynyl)methyl, phenyl substituted with $R^8$ and $R^9$; benzyl substituted with $R^8$ and $R^9$, $C_3$ to $C_7$ cycloalkyl, ($C_3$ to $C_7$ cycloalkyl)methyl or $C_1$ to $C_5$ haloalkyl
$R^{14}$ is H or $R^{13}$;
$R^{15}$ is H, $C_1$ to $C_4$ alkyl, ($C_2$ to $C_4$ alkenyl)methyl or ($C_2$ to $C_4$ alkenyl)methyl; or $R^{14}$ and $R^{15}$ may together form a b 5-or 6-membered saturated heterocycle which contains the amine nitrogen and optionally a heteroatom of N, O or S;

$R^{16}$ is H halogen, $CF_3$, OH, $C_3$ to $C_3$ alkyl, $C_1$ to $C_3$ alkoxy or $C_1$-$C_3$ alkylthio;

$R^{17}$ is H, F, Cl or $CH_3$;

$R^{18}$ is $C_1$-$C_4$ alkyl, $CH_2CN$, $CH_2SCN$;

and their agriculturally suitable salts, provided that a) when $R^2$ or $R^3$ is $CF_3$, then the other is not n-butyl;

b) when $R^3$ is phenoxymethyl or thiophenoxymethyl, then $R_{16}$ and $R_{17}$ are other than Br, I, Cl or OH.

Preferred usually for reasons of their greater fungicidal activity and/or more favorable ease of synthesis are Compounds of Formula I
wherein
Q is H;
$R^1$ is H, $C_1$ to $C_3$ alkyl, allyl or propargyl;
$R^2$ is H, $C_1$ to $C_3$ alkyl, CN or $C_2$ to $C_3$ alkenyl;
$R^3$ is phenyl substituted with $R^8$ and $R^9$; phenylmethyl, pyridylmethyl, phenoxymethyl, thiophenoxymethyl, or thienylmethyl each substitut4ed with $R^8$ and $R^9$ on the aryl radical and $R^{16}$ and $R^{17}$ on the aliphatic carbon;
$R^{15}$ is $C_1$ to $C_4$ alkyl, ($C_2$ to $C_4$ alkenyl)methyl, or ($C_2$ to $C_4$ alkynyl)methyl; and
$R^4$ is phenyl substituted with $R^8$ and $R^9$, benzyl substituted with $R^8$ and $R^9$, $C_3$ to $C_6$ cycloalkyl, thienyl optionally substituted with 1 to 2 halogen, styryl substituted with $R^8$ and $R^9$, pyridine substituted with $R^8$ and $R^9$, ($C_3$ to $C_6$ cycloalkyl)methyl or ($C_3$ to $C_6$ cycloalkyl)ethyl;

More preferred are the Preferred Compounds wherein
$R^5$ is F, Cl, $CH_3$ or $CF_3$;
$R^7$ is halogen, $CH_3$, $OH_3$, CN, phenyl optionally substituted with 1 to 3 halogens or phenoxy optionally substituted with 1 to 3 halogens;
$R^8$ is H, F, Cl;
$R^9$ is H, F, or Cl.;
$R^{16}$ is H, F, Cl or $C_1$ to $C_2$ alkyl; and $R^{17}$ is H.

Most preferred are the more preferred compounds wherein
G is

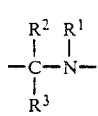

$R^1$ is H or $CH_3$;
$R^2$ is H or $CH_3$;
$R^3$ is phenyl or phenylmethyl optionally substituted with 1 to 3 F or Cl and optionally substituted on alkyl with H or $CH_3$;
$R^7$ is H, F, Cl, $CH_3$, $OCH_3$ or $C_6H_5$; and
Ar is phenyl,
or wherein
G is

and
$R^4$ is phenyl substituted with $R^8$ and $R^9$.

Specifically preferred for their more favorable ease of synthesis of greater fungicidal activity are:

1. N-[2,4-dichlorophenyl) (4-fluorophenyl)methyl]-N-methyl-1H-1H-1,2,4-triazol-1-amine;
2. N-[(2,4-dichlorophenyl)(4-fluorophenyl)methyl]-1H-1,2,4-triazol-1-amine;
3. N-[bis-(4-fluorophenyl)methyl]-N-methyl-1H-1,2,4-triazol-1-amine;
4. N-[bis-(4-fluorophenyl)methyl]-1H-1,2,4-triazol-1-amine;
5. N-[2,4-dichlorophenyl)(4-fluorophenyl)methyl]-N-methyl-1H-imidazol-1-amine;
6. N-[(2,4-dichlorophenyl)(4-fluorophenyl)methylene]-1H-1,2,4-triazole-1-amine;
7. 1H-1,2,4-triazol-1-amine, N-((1-(2,4-dichlorophenyl)-2-(4-fluorophenyl)propyl));
8. 1H-1,2,4-triazol-1-amine, N-(((4-cyanophenyl) (2,4-dichlorophenyl)methyl))-N-methyl;
9. 1H-1,2,4-triazol-1amine, N-((2-(4-chlorophenyl)-1-(2,4-difluorophenyl)propyl));
10. 1H-1,2,4-triazol-1-amine, N-((1-(2,4difluorophenyl)-2-(4-fluorophenyl)propyl)).

DETAILED DESCRIPTION OF THE INVENTION

Synthesis

The compounds of Formula I in which Q is other than H (Ia) can be prepared from compounds of Formula 1b where Q is H by metalation of Ib with strong base and subsequent treatment with appropriate reagents as described below. Suitable bases for the metalation

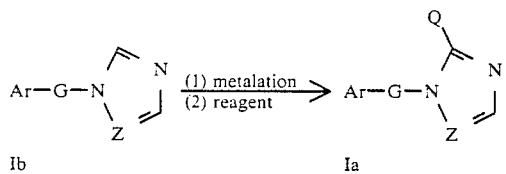

include organoalkali metal compounds such as n-butyllithium and alkali metal amides such as lithium diisopropylamide. Appropriate solvents for the metalation include hydrocarbons such as toluene or hexane, or etheral solvents such as tetrahydrofuran, dimethoxyethane of diethyl ether. The metalations can be carried out from $-80\,°$ C. to $60°$ C. for periods of 1 to 120 minutes, depending on the choice of base, solvent and substrate. The conversion of the resultant organometallic intermediate to Ia involves subsequent treatment with a methylating reagent (where Q is $CH_3$), a halogenating reagent (where Q is halogen), with a formylating reagent (where Q is CHO) or with sulfur (where Q is SH). Appropriate methylating reagents include methyl halides, methyl iodide, methyl bromide, dimethyl sulfate, and methyl sulfonates. Appropriate halogenating reagents include elemental chlorine, bromine or iodine; N-halosuccinimides, N-hakosulfonamides, carbon tetrahalides and haloperchlorates. Appropriate formylating reagents include dialkylformamides such as dimethylformamide and formic acid derivatives such as formic acetic anhydride. Typical conditions involve treatment of a solution of Ib is THF at $-78°$ C. with n-butyllithium for 15 minutes followed by addition of the halogenating reagent, the formylating reagent or sulfur as desired. When $R^1$ of Ib is H, two equivalents of base are required. Other methods for the preparation of organometallic compounds (and for subsequent transformations) which are known to one skilled in the art are applicable to the preparation of Ia. For a review of applicable metalations, see J. March, *Advanced Organic Chemistry*, 3rd Edition, J. Wiley and Sons, New York, N.Y., 1985, pp. 1169-1170.

The compounds of Formula I where Q is SH (Ic) can be converted to compounds Id where $R^{18}$ is $CH_2CN$, $CH_2SCN$ or $C_1$-$C_4$ alkyl by treatment with base and a

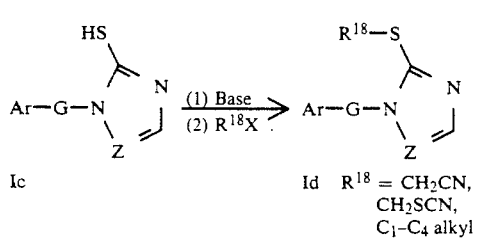

haloacetonitrile, a halomethylthiocyanate or an alkylating reagent, respectively. For example, appropriate methylating reagents include methyl iodide, methyl bromide, methyl chloride, dimethyl sulfate, and methyl sulfonates. Appropriate bases include alkali metal alkoxides such as sodium methoxide or potassium trt-butoxide, inorganic bases such as potassium carbonate or sodium hydride, or tertiary amines such as triethylamine. Suitable solvents include polar aprotic solvents such as dimethylformamide, dimethysulfoxide or acetonitrile; ethers such as tetrahydrofuran, dimethoxyethane or diethyl ether; ketones such as 2-butanone; or hydrocarbons such as toluene or benzene. The reaction temperature can vary between $-80°$ C. depending on the choice of solvent, base and substrate.

Sulfides of Formula I can be converted to the corresponding sulfoxides and sulfoxides and sulfones using standard procedures (see leading references in J. March, *Advanced Organic Chemistry* 3rd Edition, J. Wiley and Sons, New York, N.Y., 1985, pp. 1089-1090).

Compounds of Formula Ie wherein G is $-C(R^2)(R^3)N(R^1)-$ and $R^1$ is other than H can be prepared from compounds of Formula If wherein $R^1$ is H by standard literature methods for preparation of tertiary amines, secondary amides, carbamates and ureas from secondary amines (see B. C. Challis and A. R. Butler, *The Chemistry of the Amino Group*, S. Patai, Ed., Interscience, London, 1968, pp. 277-347 for an overview of such derivatizations). Typical conditions involve treatment of a solution of If and

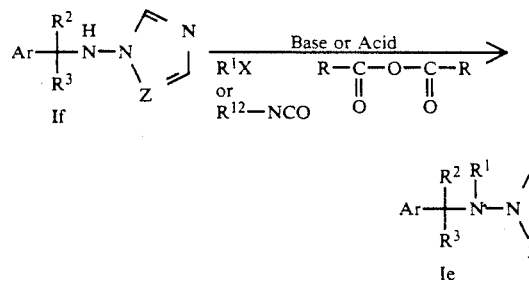

an alkylhalide, an acylhalide, a halocarbonate or an isocyanate in diethylformade with a metal hydride such as sodium hydride at 20° C. for 1 hr. $R^1$ and $R^{12}$ are as defined for Formula I. Acylation reactions can also be run under acidic conditions with the appropriate acid anhydride (such as acetic anyhdride of propionic anhydride) in acid solvents such as acetic acid or propionic acid. Addition of a strong mineral acid ($H_2SO_4$, HCl, HBr, $H_3PO_4$ and the like) catalizes the acylation reaction.

Alternatively, compounds of Formula Ie can be prepared by reaction of compounds of Formula II with

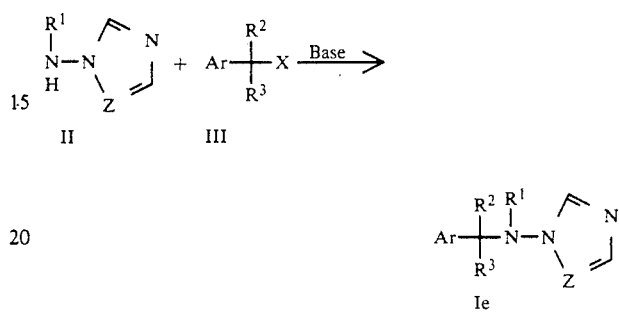

base and compounds of Formula III wherein X is an appropriate leaving group such as chlorine, bromine or iodiner a sulfonic acid radical such as methanesulfonate or p-toluenesulfonate (see B. C. Challis, and A. R. Butler, *The Chemistry of the Amino Group*, S. Patai, Ed., Interscience, London, 1968, pp. 240-301 for an overview of the alkylations of secondary amines to form tertiary amines and B. C. Challis and J. Challis, *The Chemistry of Amides*, J. Zubicky, Ed., Interscience, London, 1970, pp. 731-759 for the alkylation of primary acylated amines to form secondary acylated amines). As persons skilled in the art will recognize, the choice of solvent, base and temperature for the reaction depends on the choice of substrates. Typical conditions involve treatment of a solution of II in dimethylformamide with a strong base such as sodium hydride or potassium tert-butoxide and with III at 20° C. for twenty-four hours.

The compounds of Formula II are prepared from amines of Formula IIa by standard methods for the alkylation, acylation, carbonylation and carbamylation of primary amines (see B. C. Challis and

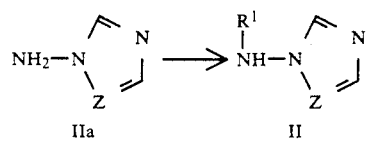

A. R. Butler, *The Chemistry of the Amino Group*, S. Patai, Ed., Interscience, London, 1968, pp. 277-347). Compounds of Formula IIa wherein Z is N or CH are known (see J. de Mendoza, M. L. Castellanos, J.-P. Fayet, M. C. Vertut, and J. Elguero, *J. Chem. Research(S)*, 1980, pp. 50-51; A. Obafemi and D. D. Kolawole; *J. Chem. Eng. Data*, 31(2) pp. 257-259).

Many of the compounds of Formula If can also be prepared from compounds of Formula IV or Formula V by reaction with $R^3M$ and $R^2M$, respectively, $R^3M$ is an organometallic reagent in which $R^3$ is

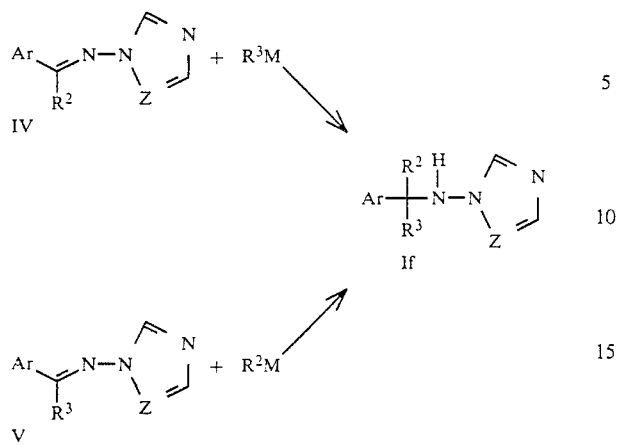

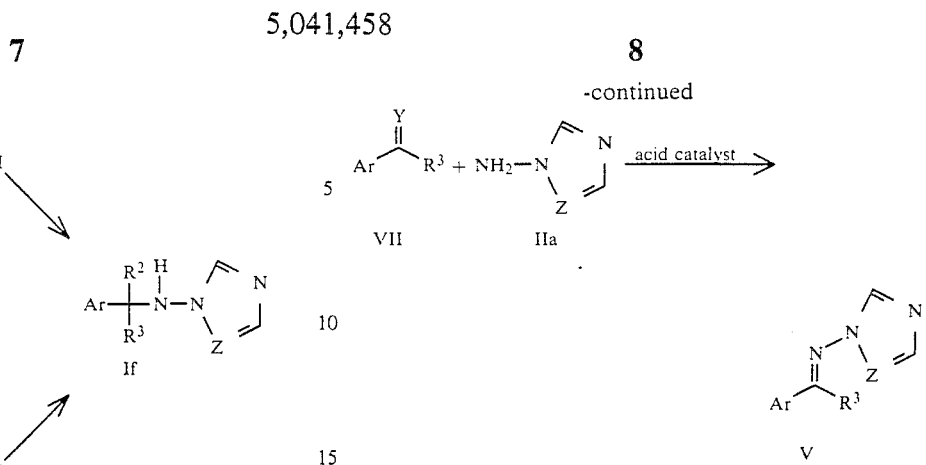

as defined for formula I and M is a metal or a metal halide, preferably lithium, sodium, magnesium chloride, magnesium bromide or magnesium iodide. R²M can be not only an organometallic reagent wherein R² is as defined previously for Formula I, but also an inorganic or organic hydride reagent (wherein R² is H) such as sodium borohydride, lithium aluminum hydride, or diisopropyl aluminum hydride. The reactions between IV and R³M and between V and R²M are typically conducted in etheral solvents such as tetrahydrofuran or diethyl ether at temperatures ranging from −80° C. to 60° C. depending on the nature of the organometallic reagent, the solvent and the substrate IV or V. The reaction of organometallic reagents with imines is well known to one skilled in the art and has been reviewed (see Harada, *The Chemistry of the Carbon-Nitrogen Double Bond*, Patai, Ed., Interscience, New York, 1970, pp. 266-272; and J. March, *Advanced Organic Chemistry*, 3rd Ed.., J. Wiley and Sons, New York, N.Y., 1985, pp. 827-828). The reduction of imines with organometallic reagents and with inorganic hydride reagents is also known in the literature. Other methods for the reduction of the carbon-nitrogen double bond are also applicable for the preparation of IV and V and have been reviewed (see Harada, *The Chemistry of the Carbon-Nitrogen Double Bond*, Patai, Ed., Interscience, New York, 1970, pp. 276-293; and J. March, *Advanced Organic Chemistry*, 3rd Ed., J. Wiley and Sons, New York, N.Y., 1985, pp. 814, 827).

Many of the compounds of Formulae IV and V can be prepared by reaction of compounds of Formula IIa with compounds of Formulae VI and VII, respectively.

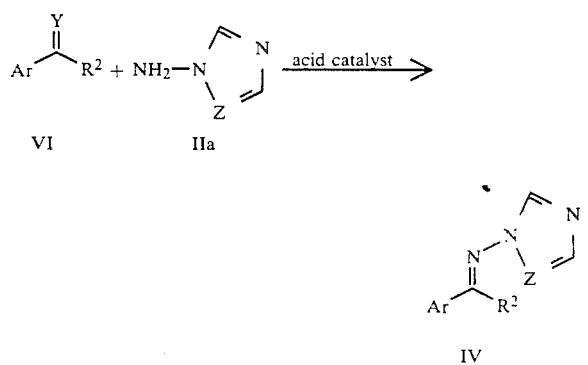

Y in VI and VII is an oxygen atom or a nitrogen atom substituted with a hydrogen. Approximately equimolar amounts of IIa relative to VI or VII are used with IIa often taken in excess of theory. The reaction is catalyzed by acid, typically an inorganic protic acid such as hydrogen chloride, hydrogen bromide or sulfuric acid; and organic protic acid such as trifluoroacetic acid, methanesulfonic acid or p-toluene-sulfonic acid; or a metallic Lewis acid such a boron trifluoride, titanium tetrachloride or aluminum trichloride. The amount of acid relative to the amount of IIa can vary from 1% to 150% depending on the nature of substrate VI or VII. Suitable solvents include ethers such as tetrahydrofuran or diethyl ether; polar aprotic solvents such as dimethylformamide, dimethyl sulfoxide or acetonitrile; hydrocarbons such as benzene, toluene or xylene; or chlorinated hydrocarbons such as methylene chloride, 1,2-dichloroethane or chlorobenzene. The reaction temperature can vary between 0° C. and 200° C. and the reaction time can vary from 5 minutes to 4 days. The optimum temperature and reaction time will vary with the concentration and choice of reagents, with the choice of solvent and with the concentration and choice of acid catalyst. Other methods for the preparation of imines are well known in the literature and are applicable for the preparation of IV and V (see J. March, *Advanced Organic Chemistry*, 3rd Ed., J. Wiley and Sons, New York, N.Y., 1985, p. 1165).

Compounds of Formula Ig in which G is C(R⁴)=N can be prepared by the methods delineated below.

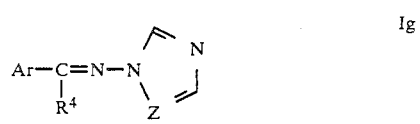

Persons skilled in the art will recognize that the set of compounds represented by Formula Ig overlaps with the set of compounds represented by V. Thus the compounds of Formula Ih (which constitute a subset of the compounds of Formula Ig in which R⁴ is other than OR¹³, SR¹³ or N(R¹⁴)(R¹⁵) can be prepared from compounds of Formula IIa and Formula VIII wherein

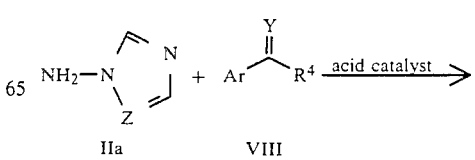

-continued

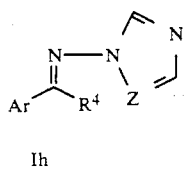
Ih

Y is oxygen or nitrogen bonded to hydrogen; and $R^4$ is as described for Formula I, excluding $OR^{13}$, $SR^{13}$ and $N(R^{14})(R^{15})$. The conditions for the preparation of V from VII are applicable for the preparation of Ih from VIII.

The compounds of Formula Ii constituting a subset of the compounds of Formula Ig in which $R^4$ is $OR^{13}$, $SR^{13}$ and $(NR^{14})(R^{15})$ can be prepared by reaction of compounds of Formula IX with $HOR^{13}$, $HSR^{13}$ and $HN(R^{14})(R^{15})$ in the presence of an acid acceptor.

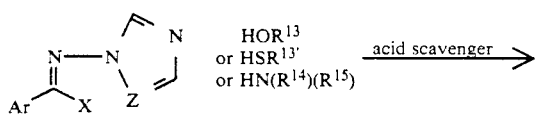

IX

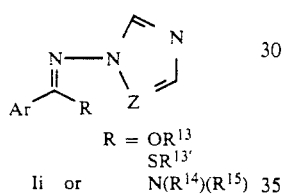

Ii

X in Formula IX is a suitable leaving group such as a halogen, preferably bromine or chlorine. Reaction of IX with $H(NR^{14})(R^{15})$ in which $R^{14}$ is H leads to Formula Ii compounds having $R^4$ as $NH(R^{15})$ and existing in two tautomeric forms, as those skilled in the art will recognize. Approximately equimolar amounts of reagents are used with $HOR^{13}$, $HSR^{13}$, $NH(R^{14})(R^{15})$ often taken in excess of IX. Suitable acid receptors include inorganic bases such as potassium carbonate or sodium hydride, tertiary amines such as triethylamine and aromatic bases such as pyridine. Suitable solvents include polar aprotic solvents such as dimethylformamide; ethers such as tetrahydrofuran, diethylether or 1,2-dimethoxyethane; ketones such as 2-butanone; hydrocarbons such as benzene or toluene; and chlorinated hydrocarbons such as 1,2-dichloroethane or chlorobenzene. The reaction temperature can vary between 0° C. and 200° C. The optimum temperature and reaction time will vary with the concentration, the choice of reagents and the choice of solvent.

The compounds of Formula IX can be prepared by reaction of compounds of Formula X

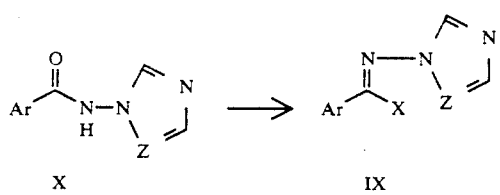

X                IX under standard dehydration/halogenation conditions known in the literature for the conversion of primary amides to imino chlorides (see Bonnett, *The Chemistry of the Carbon-Nitrogen Double Bond,* Interscience, N.Y., pp. 547–662 for an overview).

Compounds of Formula X can be prepared from amines of Formula IIa and acid halides of Formula XI,

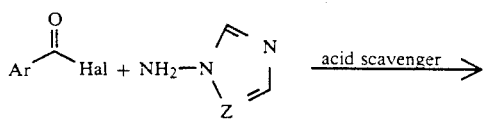

XI          IIa

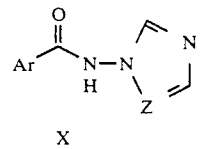

X

Those skilled in the art will recognize that not all the values of $R^2$ represent functional groups that are compatible with the reaction sequence of VIII to VI or V to If to Ie to I. For example, an alternate approach to compounds of Formula I in which $R^{16}$ is OH (Ij) are prepared in two steps, first reaction of Formula IV compounds with an appropriately protected metallic reagent XII followed by next, removal of the protecting group. M in XII is a metal

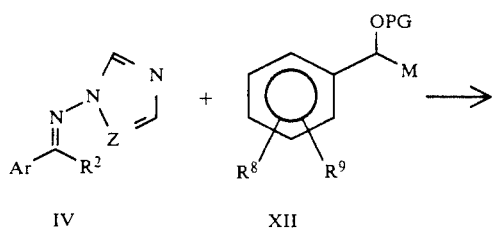

IV              XII

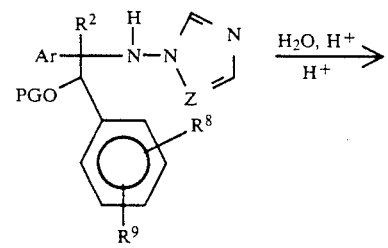

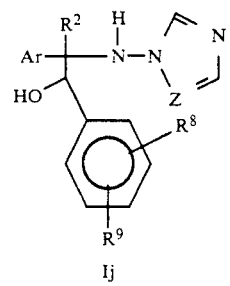

Ij or metal halide, preferably lithium, sodium, magnesium chloride, magnesium bromide or magnesium iodide. Typical protecting groups (PG) include 1-alkylethers such as 1-ethoxyethyl which are easily rendered by treatment with dilute aqueous mineral acids (HCl, HBr, H₂SO₄, H₃PO₄ and the like). In a second example, though R² as CHO will not survive the sequence of reactions to If, it can be latently manifested as an olefin (R² is CH=CH₂) by reaction of V with vinyllithium or vinylmagnesium bromide to afford compounds of Formula Ik. The amine of Ik can be acylated or alkylated to afford compounds of Formula Il as described previously for the conversion of If to Ie. Subsequent

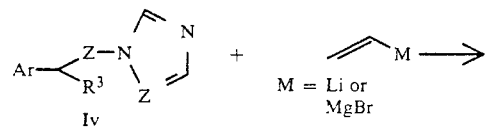

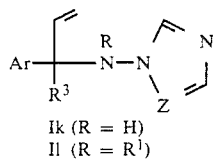

oxidative degradation of Il affords compounds of Formula I in which R² is CHO (Im). Typical methods for the conversion of olefins to aldehydes include ozonolysis with reductive work-up or

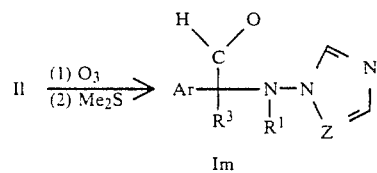

oxidation to glycols followed by oxidative cleavage (see J. March, *Advanced Organic Chemistry*, McGraw-Hill, Inc., New York, N.Y., 1977, pp. 1090–1094, 1087–1089).

Those skilled in the art will also recognize that standard functional group manipulations can be used to interconvert values of $R^1$, $R^2$ and $R^3$ at later stages of the synthetic sequence. For example, $R^2$ as CHO in Im can be converted to $R^2$ as CH₂OH, CO₂R₁₀, CN or alkenyl using standard functional group manipulations (see J. March, *Advanced Organic Chemistry*, John Wiley and Sons, New York, N.Y., 1985, pp. 806–814, 835–854, 901–906, 1086, 1096–1098, 110–1113). In a second example, compounds of Formula I in which $R^3$ is substituted with methyl (Formula In) can be prepared from compounds of Formula In in which $R^3$ is α-styryl by standard methods for the reduction of carbon-carbon double bonds

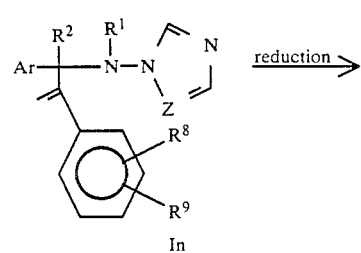

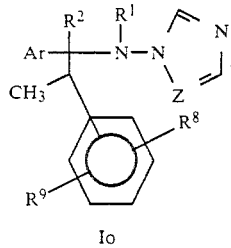

(see J. March, *Advanced Organic Chemistry*, McGraw-Hill, Inc., New York, N.Y., 1977, pp. 707–715). In a third example, compounds where $R^1$ is 4-nitrophenyl in Formula I are readily prepared from If ($R^1$=H) and p-bromanitrobenzenes by methods described for the conversion of If to Ie. The nitro group can, in turn, be converted to halogen, CN or H by methods set out in the literature (see J. March, *Advanced Organic Chemistry*, McGraw-Hill, Inc., New York, N.Y., 1977, 1125–1126, 578–579, 660–662).

The compounds of Formulae II, IV, V, IX and X are valuable intermediates for the preparation of compounds of Formula I and, consequently, for this invention. Furthermore, II, IV, IX and X can serve as intermediates for the preparation of other pesticides.

Those skilled in the art will recognize that Formula I compounds can contain one or more asymmetric carbon atoms. The stereoisomers that result can be separated using standard methods known in the art if desired. In addition, compounds of Formula I, wherein G is —C($R_4$)=N—, can contain two geometrical isomers.

In the following examples, abbreviations for nuclear magnetic resonance (NMR) spectra are as follows: s=singlet; d=doublet; t=triplet; q=quartet; and m=multiplet. Peak positions to NMR are reported as parts per million downfield from tetramethylsilane standards. Unless otherwise stated, ether refers to diethyl ether.

EXAMPLE 1

Preparation of 4-Fluoro-N-(1H-1,2,4-triazol-1-yl-benzamide

A solution of 10 mL (84.7 mmol) of 4-fluorobenzoyl chloride, 7.5 g (89.3 mmol) of 1-amino-1H-1,2,4-triazole and 1.25 mL (89.6 mmol) of triethylamine in 100 mL of benzene was heated at reflux for 3 h. The reaction mixture was diluted with ethyl acetate and washed with water and brine. Drying (MgSO₄) and removal of solvent afforded product which was purified by trituration with hot n-butylchloride; yield 2.95 g (16%); mp 210°–213° C.

Following the procedures described earlier and exemplified by Example 1, the compounds in Table I can be prepared.

TABLE I

| $R^5$ | $R^6$ | $R^7$ | Z | Properties |
|---|---|---|---|---|
| H | 2-Cl | 4-Cl | N | |
| H | H | 4-Cl | N | m.p. 227–230° C. |

TABLE I-continued

[Structure: benzene ring with R5, R6, R7 substituents connected to C(=O)-N(H)-N linked to triazole/imidazole ring with Z]

| R5 | R6 | R7 | Z | Properties |
|----|----|----|---|------------|
| H | H | H | N | |
| H | H | 4-C6H5 | N | |
| H | H | 2-Cl | N | |
| H | 4-F | 2-F | N | |
| H | H | 2-F | N | |
| H | H | 4-C6H5 | N | |
| H | 2-Cl | 4-C6H5O | N | |
| H | H | 4-(4-Cl—C6H4O) | N | |
| H | 4-F | 2-Cl | N | |
| H | H | 3-F | N | |
| H | 4-Cl | 2-Me | N | |
| H | H | 4-NO2 | N | |
| H | H | 4-CH3 | N | |
| H | H | 4-OCH3 | N | m.p. 200–201° C. |
| H | H | 4-CF3 | N | |
| H | H | 2-CN | N | |
| H | 2-F | 4-C6H5O | N | |
| H | 2-Cl | 4-(4-Cl—C6H4O) | N | |
| H | 2-Cl | 4-(4-F—C6H4O) | N | |
| H | H | 4-F | CH | |
| H | H | H | CH | |
| H | H | 2-Cl | CH | |
| H | 4-F | 2-F | CH | |
| H | H | 4-C6H5O | CH | |
| H | H | 4-(4-Cl—C6H4) | CH | |
| H | 4-F | 2-CH3 | CH | |
| H | H | 4-CH3 | CH | |
| H | H | 4-CF3 | CH | |
| H | 2-F | 4-C6H5O | CH | |
| H | 2-Cl | 4-(4-F—C6H4O) | CH | |
| H | 2-F | 4-(2,4-diCl—C6H3) | N | |
| H | 2-Cl | 4-(2,4-diF—C6H3) | N | |
| 6-F | 4-F | 2-F | N | |
| H | 2-Cl | 4-CN | N | |
| H | 2-Cl | 4-(2,4-diCl—C6H3O) | N | |
| H | H | 2-(3-Cl—C6H4O) | N | |
| H | 4-Cl | 2-(3-Cl—C6H4) | N | |

EXAMPLE 2

Preparation of N-ethyl-N-(1H-1,2,4-triazol-1-yl)amine

A solution of 5.0 g (0.114 mmol) of acetaldehyde, 10.5 g (0.125 mol) of 1-amino-1H-1,2,4-triazole and 0.3 g p-toluenesulfonic acid in 100 mL of benzene is heated of reflux with azeotropic removal of water for 4 h. Solvent is removed and the residue is dissolved in 100 mL of ethanol. 5.0 g (0.135 mol) of sodium borohydride is added and the solution is stirred 3 h. The reaction mixture is diluted with ethyl acetate and washed with aqueous sodium bicarbonate, water and brine. Drying (MgSO4) and removal of solvent gives product which may be purified by chromatography.

Following the procedures described earlier and exemplified by Examples 1 and 2, the compounds in Table II can be prepared.

TABLE II

[Structure: R1—N(H)—N linked to triazole/imidazole ring with Z]

| R1 | Z | Properties |
|----|---|------------|
| C(O)CH3 | N | |
| C(O)CH3 | CH | |
| C(O)C(CH3)3 | N | |
| C(O)C(CH3)3 | CH | |
| C(O)OCH3 | N | |
| C(O)OCH3 | CH | |
| C(O)NHCH3 | N | |
| C(O)NHCH3 | CH | |
| C(O)CF3 | N | |
| C(O)CF3 | CH | |
| C(O)(CH2)3CH3 | N | |
| C(O)(CH2)3CH3 | CH | |
| C(O)OCH(CH3)2 | N | |
| C(O)OCH(CH3)2 | CH | |
| C(O)O(CH2)3CH3 | N | |
| C(O)O(CH2)3CH3 | CH | |
| C(O)NH(CH2)3CH3 | N | |
| C(O)NH(CH2)3CH3 | CH | |
| C2H5 | CH | |
| (CH2)3CH3 | N | |
| (CH2)3CH3 | CH | |
| CH2C6H5 | N | |
| CH2C6H5 | CH | |
| CH2-(4-Cl—C6H4) | N | |
| CH2-(4-Cl—C6H4) | CH | |
| CH2-(4-F—C6H4) | N | m.p. 63–67° C. |
| CH2-(4-F—C6H4) | CH | |
| cyclopentyl | N | |
| cyclopentyl | CH | |
| CH2cyclopropyl | N | |
| CH2cyclopropyl | CH | |
| (CH2)2CH=CH2 | N | |
| (CH2)2CH=CH2 | CH | |
| CH2-(2,4-diCl—C6H3) | N | m.p. 95–97° C. |

EXAMPLE 3

Preparation of 4-Fluoro-N-(1H-1,2,4-triazol-1-yl-benzimine chloride

A solution of 5.0 g (24.3 mmol) of 4-fluoro-N-(1H-1,2,4-triazol-1-yl)-benzamide and 5.1 g (24.5 mmol) phosphorous pentachloride in 20 mL of phosphorus oxychloride is heated to reflux for 1 h. Excess POCl3 is stripped and the residue is purified by recrystallization.

Following the procedure described herein and exemplified by example 3, the compounds of Table III may be prepared.

TABLE III

[Structure: benzene ring with R5, R6, R7 substituents connected to C(=N-N-triazole)X]

| R5 | R6 | R7 | X | Z | Properties |
|----|----|----|----|---|------------|
| H | 6-Cl | 2-Cl | Cl | N | |
| H | H | 4-Cl | Cl | N | |
| H | H | H | Cl | N | |
| H | H | 4-C6H5 | Cl | N | |
| H | H | 2-Cl | Cl | N | |
| H | 4-F | 2-F | Cl | N | |
| H | H | 2-F | Cl | N | |
| H | H | 4-C6H5O | Cl | N | |
| H | 2-Cl | 4-C6H5O | Cl | N | |
| H | H | 4-(4-Cl—C6H4O) | Cl | N | |
| H | 4-F | 2-Cl | Cl | N | |

TABLE III-continued

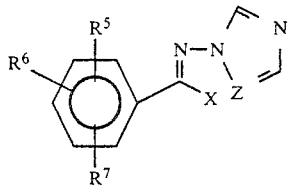

| R$^5$ | R$^6$ | R$^7$ | X | Z | Properties |
|---|---|---|---|---|---|
| H | 4-Cl | 2-Cl | Cl | N | |
| H | H | 4-CF$_3$ | Cl | N | |
| H | H | 4-OCH$_3$ | Cl | N | |
| H | H | 4-CH$_3$ | Cl | N | |
| H | H | 4-CN | Cl | N | |
| H | H | 2-CN | Cl | N | |
| H | 4-CH$_3$ | 2-Cl | Cl | N | |
| H | H | 4-NO$_2$ | Cl | N | |
| H | 2-F | 4-C$_6$H$_5$O | Cl | N | |
| H | 2-Cl | 4-(4-Cl—C$_6$H$_4$O) | Cl | N | |
| H | 2-Cl | 4-(4-F—C$_6$H$_4$O) | Cl | N | |
| H | 2-Cl | 4-(4-ClC$_6$H$_4$) | Cl | N | |
| H | 6-Cl | 2-Cl | Cl | CH | |
| H | H | 4-C$_6$H$_5$ | Cl | CH | |
| H | H | 2-Cl | Cl | CH | |
| H | 4-F | 2-F | Cl | CH | |
| H | H | 4-C$_6$H$_5$O | Cl | CH | |
| H | H | 4-(4-Cl—C$_6$H$_4$O) | Cl | CH | |
| H | 4-Cl | 2-Cl | Cl | CH | |
| H | H | 4-CF$_3$ | Cl | CH | |
| H | H | 4-CH$_3$ | Cl | CH | |
| H | H | 4-CN | Cl | CH | |
| H | 4-CH$_3$ | 2-Cl | Cl | CH | |
| H | 2-F | 4-C$_6$H$_5$O | Cl | CH | |
| H | 2-Cl | 4-(4-F—C$_6$H$_4$O) | Cl | CH | |
| H | H | 4-(4-Cl—C$_6$H$_4$) | Br | N | |
| H | 2-Cl | 4-(4-F—C$_6$H$_4$O) | Br | N | |
| H | H | 4(2,4-diCl—C$_6$H$_3$O) | Br | N | |
| H | H | 4-(4-F—C$_6$H$_4$O) | Br | N | |
| H | H | 4-(4-F—C$_6$H$_4$) | Br | N | |
| H | 2-Cl | 4-(4-Cl—C$_6$H$_4$O) | Br | N | |
| H | 4-Cl | 2-CN | Br | N | |
| H | 4-CF$_3$ | 2-F | Br | N | |
| 6-F | 4-F | 2-F | Br | N | |
| H | 4-Cl | 2-(3-Cl—C$_6$H$_4$) | Cl | N | |
| H | 4-Cl | 2-(3-Cl—C$_6$H$_4$O) | Cl | N | |

EXAMPLE 4a

Preparation of
N-[(4-Fluorophenyl)methylene]-1H-1,2,4-triazol-1-amine

A solution of 42.3 g (0.377 mol) of 75% pure 1-amino-1H-1,2,4-triazole, 40.0 mL (0.372 mol) of 4-fluorobenzaldehyde and 2.0 g of p-toluenesulfonic acid in 600 mL of tetrahydrofuran was stirred at room temperature for 2½ days. The reaction mixture was diluted with ethyl acetate, washed with saturated aqueous Na$_2$CO$_3$, water and brine and dried (MgSO$_4$). Removal of solvent gave a white solid which was recrystallized from n-butyl-chloride to afford 48.3 g (67%) of desired product as white needles; mp 118°–120° C. Concentration of the filtrate and recrystallization of the residue afforded 12.8 g (18%) more of product; mp 118°–120° C.

EXAMPLE 4b

Preparation of
N-[Phenyl-(phenylmethyl)methylene]-1H-1,2,4-triazol-1-amine

A solution of 5.7 g (50.8 mmol) of 75% pure 1-amino-1H-1,2,4-triazole, 5.0 g (25.5 mmol) of deoxybenzoin and 0.6 g p-toluenesulfonic acid in 150 mL of benzene was heated at reflux with azeotropic removal of water for 7 days. Solvent was stripped and the residue was diluted with ether, which was washed with saturated aqueous Na$_2$CO$_3$, water and brine. Drying (MgSO$_4$) and removal of solvent gave an off-white solid which was recrystallized from hexane affording 3.23 g of the desired product, m.p. 78°–80° C.

EXAMPLE 4c

Preparation of
N-(Diphenylmethylene)-1H-1,2,4-triazol-1-amine

Anhydrous methanolic HCl was prepared by dissolving 6.4 mL (90.0 mmol) of acetyl chloride in 100 mL of methanol 10.0 gm (89.3 mmol) of 1-amino-1,2,4-triazole (approximately 75% pure) was added and the solvent was removed to afford a white solid which was dried in vacuo. A portion (4.62 g, 28.7 mmol) of the solid was suspended in 100 mL of 1,2-dichloroethane and 4.0 mL (24.5 mmol) of benzophenone imine were added. The mixture was heated at reflux for 16 h. After cooling to room temperature, it was diluted with methylene chloride, washed with saturated aqueous Na$_2$CO$_3$, water and brine and dried (MgSO$_4$). Removal of solvent gave an oil from which desired product was crystallized in hexanes as off-white needles; yield 3.0 (49%), mp 126°–129° C.

EXAMPLE 4d

Preparation of
N-[(4-Fluorophenyl)(1-morpholinyl)methylene]-1H-1,2,4-triazol-1-amine A solution of 2.0 g (8.9 mmol) of 4-fluoro-N-(1H-1,2,4-triazol-1-yl)benzimino chloride, 0.90 g (10.3 mmol) of morpholine and 0.9 g (8.9 mmol) triethylamine in 40 mL of benzene is heated at reflux for 5 h. The reaction mixture is diluted with ethyl acetate and washed with water and brine. Drying (MgSO$_4$) and removal of solvent affords the desired product which can be purified by chromatography on silica gel.

EXAMPLE 4e

Preparation of
N-[1,1-Dimethylethoxy)(4-fluorophenyl)methylene]-1H-1,2,4-triazole-1-amine Added to a solution of 2.0 g (8.4 mmol) of 4-fluoro-N-(1H-1,2,4-triazol-1-yl)-benzimino chloride in tetrahydrofuran is 1.1 g (9.8 mmol) of potassium t-butoxide at 0° C. The solution is stirred 0.5 h before being diluted with ethyl acetate and being washed with water and brine. Drying (MgSO$_4$) and removal of solvent gives the desired product which can be purified by chromatography.

EXAMPLE 4f

Preparation of
N-[(4-Fluorophenyl)(1-methylethylmercapto)methylene]-1H-1,2,4-triazole-1-amine A solution of 1.83 g (8.9 mmol) of 4-fluoro-N-(1H-1,2,4-triazol-1-yl)-benzamide and 1.05 g (8.9 mmol) of phosphorous pentachloride and 20 mL of phosphorous oxychloride is heated at reflux for 1 h. Solvent is stripped and the residue dissolved in 30 mL of benzene. Triethylamine (1.4 mL, 10 mmol) and 1.0 g (13 mmol) of isopropyl mercaptan is added and the solution is heated at reflux for 4 h. The solution is diluted with ethyl acetate and washed with water and brine. Drying (MgSO₄) and removal of solvent gives product which is purified by chromatography on silica gel.

EXAMPLE 4g

Preparation of N-(Diphenylmethylene)-5-iodo-1H-1,2,4-triazol-1-amine

A solution of 1.3 g (12.8 mmol) of diisopropyl amine in 30 mL is cooled to −78° C. n-Butyllithium (4.3 mL of a 1.6M solution in hexanes, 6.9 mmol) is added dropwise. Over ½ h, the solution is warmed to 0° C. and recooled to −78° C. A solution of 2.0 g (6.3 mmol) of N-(1H-1,2,4-triazol-1-yl)-benzophenone imine in 5 mL of tetrahydrofuran is added. The solution is stirred 10 min before 1.7 g (6.7 mmol) of iodine are added. The reaction mixture is warmed to room temperature, diluted with ethyl acetate and washed with saturated aqueous NaHSO₃, water and brine. Drying (MgSO₄) and removal of solvent gives the desired product.

EXAMPLE 4h

Preparation of N-[2-(4-chlorophenoxy)-1-(4-fluorophenyl)ethylidene]-1H-1,2,4-triazol-1-amine To a stirred solution of 1-amino-1H-1,2,4-triazole (75% purity, 5.6 g, 0.05 mmol) and 2-(4-chlorophenoxy)-4'-fluoroacetophenone (13.2 g, 0.05 mmol) in 100 mL dry toluene is added a catalytic amount (1.0 g) p-toluene sulfonic acid. The mixture is heated at reflux with azeotropic removal of water for 4 days. Solvent is evaporated and the residue taken up in 200 mL ethyl acetate. The organic solution is washed with 2×100 mL 10% aqueous Na₂CO₃ and 1×100 mL brine. The dried (MgSO₄) solution is filtered and concentrated to give the desired product which can be purified by chromatography or crystallization from an appropriate solvent.

Following the procedures described earlier and exemplified by Examples 4a, 4b, 4c, 4d, 4e, 4f, 4g, and 4h, compounds in Table IVa can be prepared.

TABLE IVa

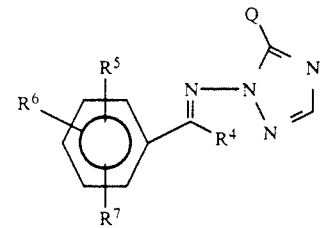

| R⁴ | R⁵ | R⁶ | R⁷ | Q | Properties |
|---|---|---|---|---|---|
| 4-Cl—C₆H₄ | H | H | 4-Cl | H | oil, δ 8.1 (s, 1H, triazole C—H) |
| 4-F—C₆H₄ | H | H | 4-F | H | m.p. 84–86° C. |
| 4-F—C₆H₄ | H | 4-Cl | 2-Cl | H | m.p. 129–131° C. |
| 2-F—C₆H₄ | H | H | 4-Cl | H | |
| 2-Cl—C₆H₄ | H | H | 4-F | H | oil, δ 8.2 (s, 1H, triazole C—H) |
| 4-C₆H₅ | H | H | 4-F | H | |
| 2,4-diCl—C₆H₃ | H | 4-Cl | 2-Cl | H | |
| 4-CF₃—C₆H₄ | H | H | 4-CF₃ | H | |
| 3-pyridyl | H | H | H | H | oil δ 4.3 and 4.0 (2s, 1H, triazole C—H) |
| 4-pyridyl | H | H | H | H | oil δ 8.3 and 8.1 (2s, 1H, triazole C—H) |
| 2-pyridyl | H | 4-Cl | 2-Cl | H | m.p. 107–110° C. |
| 3-pyridyl | H | 4-Cl | 2-Cl | H | m.p. 93–105° C. |
| 4-pyridyl | H | 4-Cl | 2-Cl | H | |
| 3-thienyl | H | 4-Cl | 2-Cl | H | |
| CH₂-(4-Cl—C₆H₄) | H | H | 4-Cl | H | |
| CH₂-(4-Cl—C₆H₄) | H | 4-Cl | 2-Cl | H | |
| CH₂-(4-F—C₆H₄) | H | H | 4-F | H | |
| 2,4-diCl—C₆H₃ | H | H | 4-C₆H₅O | H | |
| C₆H₅ | H | H | 4-(4-Cl—C₆H₄O) | H | |
| 4-CN—C₆H₅—CH₂— | H | H | 4-CN | H | |
| 4-CN—C₆H₄ | H | H | 4-Cl | H | |
| 4-CF₃—C₆H₄ | H | H | 4-Cl | H | |
| 4-CH₃—C₆H₄ | H | H | 4-Cl | H | |
| 4-Br—C₆H₄—CH₂ | H | H | 4-Cl | H | |
| 4-Cl-2-CN—C₆H₃ | H | H | 4-Cl | H | |
| 4-CN-2-Br—C₆H₃ | H | H | 4-Cl | H | |
| 4-F—C₆H₄ | 2-F | 4-F | 6-F | H | |
| 2,4-diF—C₆H₃ | H | 4-Cl | 2-Cl | H | |
| 3,4-diF—C₆H₃ | H | H | 4-Cl | H | |
| 2-Cl-4-CF₃—C₆H₄ | H | H | 4-Cl | H | |
| 2-CF₃—C₆H₄ | H | 4-CN | 2-Cl | H | |
| 3-CN—C₆H₄ | H | 4-Cl | 2-Cl | H | |
| 3-CF₃—C₆H₄ | H | 4-Cl | 2-F | H | |
| C₆H₅ | H | H | 4-CF₃ | H | |
| 1-(4-F—C₆H₄)-vinyl | H | 4-Cl | 2-Cl | H | |
| C₆H₅ | H | H | 4-CF₃ | H | |

TABLE IVa-continued

| R⁴ | R⁵ | R⁶ | R⁷ | Q | Properties |
|---|---|---|---|---|---|
| 2-(2,4-diCl—C₆H₃)-vinyl | H | H | 4-F | H | |
| cyclopentyl-CH₂ | H | 4-Cl | 2-F | H | |
| 1-(cyclopropyl)-ethyl | H | H | 4-F | H | |
| (CH₃)₂CH—O | H | H | 4-F | H | |
| (CH₃)₂CH—O | H | 4-Cl | 2-Cl | H | |
| (CH₃)₂CH—O | H | H | 4-C₆H₅O | H | |
| (CH₃)₂CH—O | H | H | 4-(4-Cl-2-F—C₆H₃) | H | |
| C₂H₅O | H | H | 4-(4-Cl—C₆H₄O) | H | |
| CH₂=CH—CH₂—O | H | 2-Cl | 4-(4-Cl—C₆H₄O) | H | |
| C₆H₅O | H | H | 4-(4-Cl—C₆H₄) | H | |
| 2-Cl-4-F—C₆H₃O | H | H | 4-(4-F—C₆H₄) | H | |
| cyclopropyl-O | H | H | 4-(4-F—C₆H₄) | H | |
| cyclopentyl-O | H | H | 4-(2,4-diF—C₆H₃) | H | |
| CF₃CH₂—O | H | H | 4-Cl | H | |
| cyclohexyl-CH₂—O | H | H | 4-F | H | |
| 3-furanyl-O | H | H | 4-CH₃ | H | |
| (CH₃)₃C—S | H | H | 4-(4-Cl—C₆H₄O) | H | |
| (CH₃)₃C—S | H | 2-Cl | 4-(4-Cl—C₆H₄O) | H | |
| 2-thienyl-S | H | 4-Cl | 2-Cl | H | |
| CH₃S | H | 4-Cl | 2-Cl | H | |
| (CH₃)₂CH—CH₂—S | H | 4-Cl | 2-Cl | H | |
| C₆H₅—S | H | 4-Cl | 2-Cl | H | |
| 2,4-diCl—C₆H₃S | H | 4-Cl | 2-Cl | H | |
| morpholinyl | H | H | 4-C₆H₅O | H | |
| pyrrolidinyl | H | H | 2-C₆H₅O | H | |
| (CH₃)₂N | H | 4-F | 2-C₆H₅ | H | |
| (CH₃)₂CH—S | H | 4-F | 2-(3-F—C₆H₄) | H | |
| (CH₃)(C₆H₅)N | H | H | 4-(4-Cl—C₆H₄O) | H | |
| (CH₃)₂N | H | H | 4-(4-F—C₆H₄O) | H | |
| (CH₃)(C₆H₅)N | H | 4-Cl | 2-Cl | H | |
| C₆H₅NH | H | 4-Cl | 2-Cl | H | |
| (CH₃)(4-Cl—C₆H₄)N | H | 4-Cl | 2-Cl | H | |
| (CH₃)(cyclopentyl)N | H | 4-Cl | 2-Cl | H | |
| (CH₂=CH—CH₂)₂N | H | 4-Cl | 2-Cl | H | |
| 4-Cl—C₆H₄ | H | 4-Cl | 2-Cl | I | |
| (CH₃)₂CH—O | H | 4-Cl | 2-Cl | Cl | |
| 4-F—C₆H₄ | H | H | 4-F | SH | |
| (CH₃)(4-Cl—C₆H₄)N | H | 4-Cl | 2-Cl | SCH₂CN | |
| 4-CN—C₆H₄— | H | 4-Cl | 2-Cl | H | m.p. 136–138° C. |
| 3,5-diCl-2-pyridyl | H | H | 4-Cl | H | m.p. 132–133° C. |
| 3,5-diCl-2-pyridyl | H | H | 4-F | H | oil, δ 8.4 (s, 1H triazole C—H) |
| 4-F—C₆H₄ | H | 4-Cl | 2-Cl | SH | m.p. 91–96° C. |
| 4-F—C₆H₄ | H | 4-Cl | 2-Cl | SCH₂SCN | m.p. 122–125° C. |
| 4-F—C₆H₄—O | H | H | 4-Cl | H | m.p. 84–87° C. |
| 4-Cl—C₆H₄—S | H | H | 4-Cl | H | m.p. 114–124° C. |
| 4-Cl—C₆H₄—N(CH₃)— | H | H | 4-Cl | H | m.p. 144–146° C. |

Following the procedures described earlier and exemplified by Examples 4a, 4b, 4c, 4d, 4e, 4f, 4g, and 4h, compounds in Table IVb can be prepared.

TABLE IVb

| R⁴ | R⁵ | R⁶ | R⁷ | Q | Properties |
|---|---|---|---|---|---|
| 4-Cl—C₆H₄ | H | H | 4-Cl | H | |

TABLE IVb-continued

| R⁴ | R⁵ | R⁶ | R⁷ | Q | Properties |
|---|---|---|---|---|---|
| 4-F—C₆H₄ | H | H | 4-F | H | |
| 4-F—C₆H₄ | H | 4-Cl | 2-Cl | H | oil, δ 6.6 (s. 1H imidazole C—H) |
| 2-F—C₆H₄ | H | H | 4-Cl | H | |
| 2-Cl—C₆H₄ | H | H | 4-F | H | |
| C₆H₅ | H | H | 4-F | H | |
| 2,4-diCl—C₆H₃ | H | 4-Cl | 2-Cl | H | |
| 4-CF₃—C₆H₄ | H | H | 4-CF₃ | H | |
| 3-pyridyl | H | H | H | H | |
| 4-pyridyl | H | H | H | H | |
| 3,5-diCl-2-pyridyl | H | H | 4-F | H | oil, δ 6.6 (s, 1H imidazole C—H) |
| 3-pyridyl | H | 4-Cl | 2-Cl | H | |
| 4-pyridyl | H | 4-Cl | 2-Cl | H | |
| 3-thienyl | H | 4-Cl | 2-Cl | H | |
| CH₂—(4-Cl—C₆H₄) | H | H | 4-Cl | H | |
| CH₂—(4-Cl—C₆H₄) | H | 4-Cl | 2-Cl | H | |
| CH₂—(4-F—C₆H₄) | H | H | 4-F | H | |
| 2,4-diCl—C₆H₃ | H | H | 4-C₆H₅O | H | |
| C₆H₅ | H | H | 4-(4-Cl—C₆H₄O) | H | |
| C₆H₅ | H | H | H | H | |
| 2-Cl-4-F—C₆H₃O | H | H | 4-(4-F—C₆H₄) | H | |
| cyclopropyl-O | H | H | 4-(4-F—C₆H₄) | H | |
| cyclopentyl-O | H | H | 4-(2,4-diF—C₆H₃) | H | |
| CF₃CH₂—O | H | H | 4-Cl | H | |
| cyclopentyl-CH₂—O | H | H | 4-F | H | |
| 3-furanyl-O | H | H | 4-CH₃ | H | |
| (CH₃)₃C—S | H | H | 4-(4-Cl—C₆H₄O) | H | |
| (CH₃)₃C—S | H | 2-Cl | 4-(4-Cl—C₆H₄O) | H | |
| 2-thienyl-S | H | 4-Cl | 2-Cl | H | |
| CH₃S | H | 4-Cl | 2-Cl | H | |
| (CH₃)₃C—CH₂—S | H | 4-Cl | 2-Cl | H | |
| C₆H₅—S | H | 4-Cl | 2-Cl | H | |
| 2,4-diCl-C₆H₃S | H | 4-Cl | 2-Cl | H | |
| morpholinyl | H | H | 4-C₆H₅O | H | |
| pyrrolidinyl | H | H | 2-C₆H₅O | H | |
| (CH₃)₂N | H | 4-F | 2-C₆H₅ | H | |
| (CH₃)₂CH—S | H | 4-F | 2-(3-F—C₆H₄) | H | |
| (CH₃)(C₂H₅)N | H | H | 4-(4-Cl—C₆H₄O) | H | |
| (CH₃)₂N | H | H | 4-(4-F—C₆H₄O) | H | |
| (CH₃)(C₆H₅N) | H | 4-Cl | 2-Cl | H | |
| C₆H₅NH | H | 4-Cl | 2-Cl | H | |
| (CH₃)(4-Cl—C₆H₄)N | H | 4-Cl | 2-Cl | H | |
| (CH₃)(cyclopentyl)N | H | 4-Cl | 2-Cl | H | |
| (CH₂=CH—CH₂)₂N | H | 4-Cl | 2-Cl | H | |
| 4-Cl—C₆H₄ | H | 4-Cl | 2-Cl | I | |
| (CH₃)₂CH—O | H | 4-Cl | 2-Cl | Cl | |
| 4-F—C₆H₄ | H | H | 4-F | SH | |
| (CH₃)(4-Cl—C₆H₄)N | H | 4-Cl | 2-Cl | SCH₂CN | |
| 4-CN—C₆H₄ | H | H | 4-Cl | H | |
| 4-CF₃—C₆H₄ | H | H | 4-Cl | H | |
| 4-CH₃—C₆H₄ | H | H | 4-Cl | H | |
| 4-Br—C₆H₄ | H | H | 4-Cl | H | |
| 4-Cl-2-CN—C₆H₃ | H | H | 4-Cl | H | |
| 4-CN-2-Br—C₆H₃ | H | H | 4-Cl | H | |
| 4-F—C₆H₄ | 2-F | 4-F | 6-F | H | |
| 2,4-diF—C₆H₃ | H | 4-Cl | 2-Cl | H | |
| 3,4-diF—C₆H₃ | H | H | 4-Cl | H | |
| 2-Cl-4-CF₃—C₆H₃ | H | H | 4-Cl | H | |
| 2-CF₃—C₆H₄ | H | 4-CN | 2-Cl | H | |
| 3-CN—C₆H₄ | H | 4-Cl | 2-Cl | H | |
| 3-CF₃—C₆H₄ | H | 4-Cl | 2-F | H | |
| C₆H₅ | H | H | 4-CF₃ | H | |
| 1-(4-F—C₆H₅)-vinyl | H | 4-Cl | 2-Cl | H | |
| C₆H₅ | H | H | 4-CF₃ | H | |
| 2-(2,4-diCl—C₆H₃)-vinyl | H | H | 4-F | H | |
| cyclopentyl-CH₂ | H | 4-Cl | 2-F | H | |
| 2-(cyclopropyl)-ethyl | H | H | 4-F | H | |
| (CH₃)₂CH—O | H | H | 4-F | H | |

TABLE IVb-continued

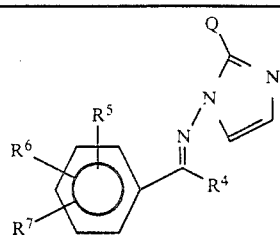

| R⁴ | R⁵ | R⁶ | R⁷ | Q | Properties |
|---|---|---|---|---|---|
| (CH₃)₂CH—O | H | 4-Cl | 2-Cl | H | |
| (CH₃)₂CH—O | H | H | 4-C₆H₅O | H | |
| (CH₃)₂CH—O | H | H | 4-(4-Cl-2-F—C₆H₃) | H | |
| C₂H₅O | H | H | 4-(4-Cl—C₆H₄O) | H | |
| CH₂=CH—CH₂—O | H | 2-Cl | 4-(4-Cl—C₆H₄O) | H | |
| C₆H₅O | H | H | 4-(4-Cl—C₆H₄) | H | |

Following the procedures described earlier and exemplified in Examples b 4a, 4b and 4c, intermediate compounds in Table IVc can be prepared.

TABLE IVc

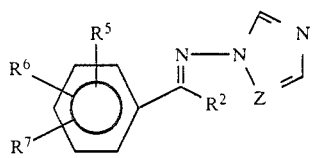

| R² | R⁵ | R⁶ | R⁷ | Z | Properites |
|---|---|---|---|---|---|
| H | H | H | 4-Cl | N | m.p. 141–144° C. |
| H | H | H | 4-CF₃ | N | |
| H | H | 4-Cl | 2-Cl | N | m.p. 151–154° C. |
| H | H | H | 2-F | N | m.p. 79–83° C. |
| H | H | H | 4-NO₂ | N | m.p. 179–190° C. |
| H | H | 4-F | 2-F | N | m.p. 128–129° C. |
| H | H | 6-F | 2-F | N | m.p. 104–109° C. |
| H | H | H | 3-F | N | |
| H | H | H | 3-Cl | N | |
| H | H | H | 4-CH₃ | N | |
| H | H | H | 4-OCH₃ | N | |
| H | H | H | 4-SO₂CH₃ | N | |
| H | H | H | 4-SCH₃ | N | |
| H | 6-F | 4-F | 2-F | N | |
| H | 6-Cl | 4-Cl | 2-Cl | N | |
| H | H | H | 4-C₆H₅ | N | |
| H | H | H | 2-(4-Cl—C₆H₄) | N | |
| H | H | 4-Cl | 2-(3-Cl—C₆H₄) | N | |
| H | H | 4-Cl | 2-(3-Cl—C₆H₄O) | N | |
| H | H | H | CN | N | |
| CF₃ | H | H | H | N | m.p. 47–53° C. |
| CF₃ | H | H | 4-Cl | N | |
| CF₃ | H | H | 4-F | N | |
| CF₃ | H | 4-Cl | 2-Cl | N | |
| CF₃ | H | H | 4-C₆H₅ | N | |
| (CH₂)₃—CH₃ | H | H | 4-C₆H₅ | N | |
| CH₃ | H | H | 4-F | N | m.p. 75–77° C. |
| CH₂CH₃ | H | H | 4-F | N | oil, δ 8.3 (s, 1H triazole C—H) |
| H | H | H | 2-CF₃ | N | m.p. 89–92° C. |
| (CH₂)₃CH₃ | H | H | 4-F | N | |
| (CH₂)₃CH₃ | H | H | 4-Cl | N | |
| (CH₂)₃CH₃ | H | 4-Cl | 2-Cl | N | |
| CH(CH₃)₂ | H | 4-Cl | 2-Cl | N | |
| CH(CH₃)₂ | H | H | 4-C₆H₅ | N | |
| CH(CH₃)(CH₂CH₃) | H | H | 4-F | N | |
| CH=CH₂ | H | 4-Cl | 2-Cl | N | |
| CH=CH₂ | H | H | 4-F | N | |
| C≡CH | H | 4-Cl | 2-Cl | N | |
| C≡C—CH₃ | H | 4-Cl | 2-Cl | N | |
| C≡C—C₂H₅ | H | H | 4-F | N | |
| (CH₂)₂C≡CH | H | 4-Cl | 2-Cl | N | |
| —(CF₂)₃CF₃ | H | H | 4-F | N | |
| CH=CH—CH₃ | H | H | 4-F | N | |
| (CH₂)₂CH=CH₂ | H | H | 4-Cl | N | |

TABLE IVc-continued

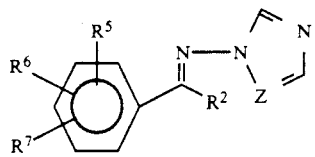

| R² | R⁵ | R⁶ | R⁷ | Z | Properties |
|---|---|---|---|---|---|
| (CH₂)₂CHBrCH₂Br | H | H | 4-Cl | N | |
| H | H | H | 4-Cl | CH | |
| H | H | H | 4-CF₃ | CH | |
| H | H | 4-Cl | 2-Cl | CH | m.p. 142–144° C. |
| H | H | H | 2-F | CH | |
| H | H | H | 4-NO₂ | CH | |
| H | H | 4-F | 2-F | CH | |
| H | H | 6-Cl | 2-Cl | CH | |
| H | H | H | 3-F | CH | |
| H | H | H | 3-Cl | CH | |
| H | H | H | 4-CH₃ | CH | |
| H | H | H | 4-OCH₃ | CH | |
| H | H | H | 4-SO₂CH₃ | CH | |
| H | H | H | 4-SCH₃ | CH | |
| H | 6-F | 4-F | 2-F | CH | |
| H | 6-Cl | 4-Cl | 2-Cl | CH | |
| H | H | H | 4-C₆H₅ | CH | |
| H | H | H | 2-(4-Cl—C₆H₄) | CH | |
| H | H | 4-Cl | 2-(3-Cl—C₆H₄) | CH | |
| H | H | 4-Cl | 2-(3-Cl—C₆H₄O) | CH | |
| H | H | H | 4-F | CH | m.p. 164–166° C. |
| H | H | H | CN | CH | |
| CF₃ | H | H | H | CH | |
| CF₃ | H | H | 4-Cl | CH | |
| CF₃ | H | H | 4-F | CH | |
| CF₃ | H | 4-Cl | 2-Cl | CH | |
| CF₃ | H | H | 4-C₆H₅ | CH | |
| (CH₂)₃CH₃ | H | H | 4-C₆H₅ | CH | |
| (CH₂)₃CH₃ | H | H | 4-F | CH | |
| (CH₂)₃CH₃ | H | H | 4-Cl | CH | |
| (CH₂)₃CH₃ | H | 4-Cl | 2-Cl | CH | |
| CH(CH₃)₂ | H | 4-Cl | 2-Cl | CH | |
| CH(CH₃)₂ | H | H | 4-C₆H₅ | CH | |
| CH(CH₃)(CH₂CH₅) | H | H | 4-F | CH | |
| CH=CH₂ | H | 4-Cl | 2-Cl | CH | |
| CH=CH₂ | H | H | 4-F | CH | |
| C≡CH | H | 4-Cl | 2-Cl | CH | |
| C≡C—CH₃ | H | 4-Cl | 2-Cl | CH | |
| C≡C—C₂H₅ | H | H | 4-F | CH | |
| (CH₂)₂C≡CH | H | 4-Cl | 2-Cl | CH | |
| —(CF₂)₃CF₃ | H | H | 4-F | CH | |
| CH=CH—CH₃ | H | H | 4-F | CH | |
| (CH₂)₂CH=CH | H | H | 4-Cl | CH | |
| (CH₂)₂CHBrCH₂Br | H | H | 4-Cl | CH | |

Following the procedures described earlier and exemplified in Examples 4a, 4b, 4c and 4h, intermediate compounds in Table IVd can be prepared.

TABLE IVd

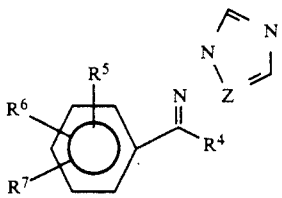

| R⁴ | R⁵ | R⁶ | R⁷ | Z | Properties |
|---|---|---|---|---|---|
| cyclopropyl | H | 4-Cl | 2-Cl | N | |
| cyclopropyl | H | H | 4-F | N | |
| cyclobutyl | H | H | 4-F | N | |
| cyclopentyl | H | H | 4-Cl | N | |
| cyclohexyl | H | H | 4-Cl | N | |
| C₆H₅CH₂ | H | 4-Cl | 2-Cl | N | |
| (4-F—C₆H₄)—CH₂ | H | 4-Cl | 2-Cl | N | |

TABLE IVd-continued

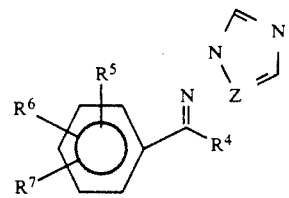

| R⁴ | R⁵ | R⁶ | R⁷ | Z | Properties |
|---|---|---|---|---|---|
| (2,4-diCl—C₆H₃)—CH₂ | H | H | 4-F | N | |
| (2,4-diCl—C₆H₃)—CH₂ | H | 4-F | 2-F | N | |
| (2,4-diCl—C₆H₃)—CH₂ | H | H | 2-F | N | |
| (2,4-diCl—C₆H₃)—CH₂ | H | 4-Cl | 2-Cl | N | |
| (4-Cl—C₆H₄)—CF₂ | H | H | 4-Cl | N | |
| 4-Cl—C₆H₄—CF₂ | H | H | H | N | |
| 4-Cl—C₆H₄—CHF | H | H | 4-Cl | N | |
| 4-Cl—C₆H₄—CH(SCH₃) | H | H | 4-Cl | N | |
| 4-CN—C₆H₄—CHCl | H | H | 4-Cl | N | |
| 4-CN—C₆H₄—CH(CH₃) | H | H | 4-Cl | N | |
| 4-NO₂—C₆H₄—CH(n-butyl) | H | H | 4-Cl | N | |

TABLE IVd-continued

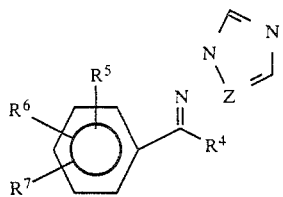

| R⁴ | R⁵ | R⁶ | R⁷ | Z | Properties |
|---|---|---|---|---|---|
| 4-CH₃—C₆H₄—CH(OCH₃) | H | H | 4-Cl | N | |
| 4-CF₃—C₆H₄—CH(isopropoxy) | H | H | 4-Cl | N | |
| 4-F—C₆H₄—CF(CH₃) | H | H | 4-Cl | N | |
| 4-F—C₆H₄—CF₂ | H | H | 4-Cl | N | |
| cyclopropyl | H | 4-Cl | 2-Cl | CH | |
| cyclopropyl | H | H | 4-F | CH | |
| cyclobutyl | H | H | 4-F | CH | |
| cyclopentyl | H | H | 4-Cl | CH | |
| cyclohexyl | H | H | 4-Cl | CH | |
| C₆H₅CH₂ | H | 4-Cl | 2-Cl | CH | |
| (4-F—C₆H₄)—CH₂ | H | 4-Cl | 2-Cl | CH | |
| (2,4-diCl—C₆H₃)—CH₂ | H | H | 4-F | CH | |
| (2,4-diCl—C₆H₃)—CH₂ | H | 4-F | 2-F | CH | |
| (2,4-diCl—C₆H₃)—CH₂ | H | H | 2-F | CH | |
| (2,4-diCl—C₆H₃)—CH₂ | H | 4-Cl | 2-Cl | CH | |
| (4-Cl—C₆H₄)—CF₂ | H | H | 4-Cl | CH | |
| 4-Cl—C₆H₄—CF₂ | H | H | H | CH | |
| 4-Cl—C₆H₄—CHF | H | H | 4-Cl | CH | |
| 4-F—C₆H₄—CH(SCH₃) | H | H | 4-Cl | CH | |
| 4-F—C₆H₄—CHCl | H | H | 4-Cl | CH | |
| 4-F—C₆H₄—CH(CH₃) | H | H | 4-Cl | CH | |
| 4-F—C₆H₄—CH(n-butyl) | H | H | 4-Cl | CH | |
| 4-CF—C₆H₄—CH(OCH₃) | H | H | 4-Cl | CH | |
| 4-Cl—C₆H₄—CH(isopropoxy) | H | H | 4-Cl | CH | |
| 4-Cl—C₆H₄—CF(CH₃) | H | H | 4-Cl | CH | |
| 4-Cl—C₆H₄—CF₂ | H | H | 4-Cl | CH | |
| 4-Cl—C₆H₄—CH₂— | H | 4-F | 2-F | N | |
| 4-Cl—C₆H₄—O—CH₂— | H | 4-F | 2-F | N | |
| 4-Cl—C₆H₄—S—CH₂— | H | 4-F | 2-F | N | |
| 4-Cl—C₆H₄—CH₂—CH(CH₃) | H | 4-F | 2-F | N | |
| 4-Cl—C₆H₄—CH(CH₃)—CH₂ | H | 4-Cl | 2-Cl | N | |
| 2,4-diCl—C₆H₃—O—CH(CH₃) | H | H | 4-Cl | N | |
| 2,4-diCl—C₆H₃—S—CH₂ | H | H | 4-Cl | N | |
| 1-cyclpropylethyl | H | 4-Cl | 2-Cl | N | |

Following the procedures described earlier and exemplified by examples 4a, 4b, 4c, intermediate compounds of Table IVe may be prepared.

TABLE IVe

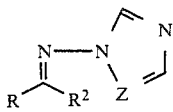

| R | R² | Z | Properties |
|---|---|---|---|
| t-butyl | H | N | m.p. 30–31° C. |
| 4-F—C₆H₄—CH(CH₃)— | H | N | oil, δ 8.3 (s, 1H triazole C—H) |
| 2,6-diF-3-pyridyl | H | N | m.p. 127–130° C. |
| 5-Cl-2-pyridyl | H | N | m.p. 163–169° C. |
| 2,Br-5-Cl-3-pyridyl | H | N | m.p. 152–153° C. |
| 3,5-diCl-2-pyridyl | H | N | |
| 5-Cl-thienyl | H | N | |
| 2,6-diCl-3-pyridyl | H | N | |
| 3-Cl-4-pyridyl | H | N | |
| 3,5-diF-2-pyridyl | H | N | |
| 5-CN-2-pyridyl | H | N | |
| 4-Cl—C₆H₄—C(CH₃)₂ | H | N | |
| 3,5-diF-2-pyridyl | H | CH | |
| 2,6-diF-3-pyridyl | H | CH | |
| 5-Cl-2-pyridyl | H | CH | |
| 3,5-diCl-2-pyridyl | H | CH | |
| 5-CN-2-pyridyl | H | CH | |

TABLE IVe-continued

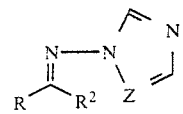

| R | R² | Z | Properties |
|---|---|---|---|
| 3-Cl-5-CN-2-pyridyl | H | CH | |

EXAMPLE 5a

Preparation of N-[(bis-(4-fluorophenyl)methyl)]-1H-1,2,4-triazol-1-amine

A solution of n-butyllithium (11.0 mL of a 1.6M hexane solution, 17.6 mmol) was added dropwise to a tetrahydrofuran solution of 2.0 mL (18.2 mmol) of 4-bromofluorobenzene cooled to −70° C. After stirring 10 min, a solution of 2.91 g (15.3 mmol) of N-[(4-fluorophenyl)-methylene]-1H-1,2,4-triazol-1-amine was added quickly. The reaction mixture was stirred 10 min. quenched with aqueous ammonium chloride and warmed to room temperature. The mixture was diluted with ethyl acetate, washed with water and brine, dried (MgSO₄) and concentrated to afford an off-white solid. Trituration with 1:1 hexanes/n-butylchloride gave produce as a white solid; yield 2.45 g (56%), mp 160°–163° C.

EXAMPLE 5b

Preparation of N-[(diphenylmethyl)]-1H-1,2,4-triazol-1-amine

Added to a solution of 2.0 g (8.1 mmol) of N-(1H-1,2,4-triazol-1-yl)-benzophenoneimine in 20 mL of ethanol was 0.45 g (12.1 mmol) sodium borohydride at room temperature. After stirring 4½ h, aqueous ammonium chloride was added and the mixture was diluted with ethyl acetate, washed with water and brine, dried (MgSO₄) and concentrated. Product can be purified by crystallization from n-butylchloride; yield 1.7 g (84%); mp 142°–145° C.

EXAMPLE 5c

Preparation of N-[(1,1-bis(4-Fluorophenyl)ethyl)]-1H-1,2,4-triazol-1-amine

A solution of 10 mL (1.5M, 150 mmol) of methyllithium in 30 mL of tetrahydrofuran was cooled to −78° C. A solution of 2.0 g (7.0 mmol) of N-[bis(4-fluorophenyl)methylene]-1H-1,2,4-triazol-1-amine in 10 mL tetrahydrofuran was added dropwise. The solution was stirred 10 min. quenched with saturated ammonium chloride and warmed to room temperature. Dilution with ethyl acetate, washing with water and brine, drying (MgSO₄) and removal of solvent gave product as a viscous oil. Chromatography on silica gel (10:1 methylene chloride-acetate) gave of desired product as a white solid; yield 1.1 g, mp 114°–119° C.

EXAMPLE 5d

Preparation of
N-[1,2-bis(4-Fluorophenyl)-2-propenyl)]-1H-1,2,4-triazol-1-amine and
N-[(1,2-bis(4-Fluorophenyl)-2-propenyl)]-N-methyl-1H-1,2,4-triazol-1-amine A solution of 4.8 g (23.8 mmol) of α-bromo-4-fluorostyrene in 10 mL of tetrahydrofuran was added dropwise to 0.55 g (22.5 mmol) of magnesium and a few grains of iodine in 30 mL of tetrahydrofuran. After most of the magnesium had been consumed (1.5 h), the reaction was cooled to 0° C. and a solution of 2.0 g (10.5 mmol) of N-[(4-fluorophenyl)methylene]-1H-1,2,4-triazol-1-amine was added dropwise. After stirring 2 h, 1.5 mL of methyl iodide were added and the reaction mixture was stirred 16 h. The mixture was diluted with ethyl acetate, washed with water and brine, dried ($MgSO_4$) and concentrated to give an oil. Chromatography on silica gel (4:1 methylene chloride/hexanes followed by gradient elation to methylene chloride) afforded 2 components. The less polar component was identified as the second title compound; yield 1.5 g, oil, $^1HNMR$ ($CDCl_3$): δ 3.0(s,3H), 5.2(s,1H), 5.4(s, 1H), 5.8(s,1H), 6.8–7.3(m,8H), 7.8(s,2H); and the more polar component was identified as the first title compound; yield 400 mg, oil, $^1HNMR$ ($CDCl_3$): δ 5.7(s,1H), 5.75(s,1H), 5.8(s,1H), 7.0–7.3(m, 8H), 7.7(s,1H), 8.0(s,1H).

EXAMPLE 5e

Preparation of
N-[(1,2-bis(4-Fluorophenyl)propyl)]-1H-1,2,4-triazol-1-amine

A solution of 0.49 g (1.5 mmol) of N-[(1,2-bis(4-fluorophenyl-2-propenyl)]-1H-1,2,4-triazol-1-amine in 50 mL of ethanol was hydrogenated at 45 psi over 500 mg of 10% palladium on carbon for 2 h at room temperature. The solution was filtered through Celite ® which was washed through with ethyl acetate. Removal of solvent gave the desired product as an oil; yield 0.45 g; $^1HNMR$ ($CDCl_3$): 0.8(d), 1.1(m), 4.2–4.7(m), 5.1(s), 6.5–7.4(m), 7.6(s), 7.8(s).

EXAMPLE 5f

Preparation of
N-[(2,4-Dichlorophenyl)(4-fluorophenyl)-methyl]-N-methyl-1H-1,2,4-triazol-1-amine A solution of 40.0 g (0.119 mol) of N-[1-(2,4-dichlorophenyl)-1-(4-fluorophenyl)methyl]-1H-1,2,4-triazol-1-amine and 40 mL (0.64 mol) of methyl iodide in 250 mL dimethyl formamide was cooled to 0° C. Sodium hydride (4.5 g; 0.19 mol, freed from oils) was added portionwise. The reaction mixture was warmed to room temperature, stirred 1 h and quenched by dropwise addition of aqueous ammonium chloride. The mixture was diluted with ether, and washed three times with water and with brine. Drying ($MgSO_4$) and removal of solvent gave product as an oil. Crystallization from hexanes afforded 27.7 g (66% yield) of the desired product as a white solid; mp 118°–119° C.

EXAMPLE 5g

Preparation of
1-[(N-(2,4-Dichlorophenyl)-1-(4-fluorophenyl)methyl)-N-methylamino]-1H-1,2,4-triazol-5-thiol A solution of (N-[(2,4-dichlorophenyl)(4-fluorophenyl)methyl]-N-methyl-1H-1,2,4-triazol-1-amine in 30 mL tetrahydrofuran was cooled to −78° C. A hexane solution of n-butyllithium (6.5 mL, 1.6M, 10.4 mmol) was added dropwise. After stirring 15 min., 1.0 g (31.0 mmol) of sulfur was added and the reaction mixture was warmed to room temperature. The reaction was quenched with saturated aqueous ammonium chloride and diluted with ethyl acetate. Washing with water and brine, drying ($MgSO_4$) and removal of solvent gave a gummy solid. Crystallization from n-butylchloride afforded the desired product as a white solid; mp 216°–218° C.

EXAMPLE 5h

Preparation of Formamide,
N-[bis(4-fluorophenyl)methyl]-N-(1H,1,2,4-triazol-1-yl)

Formic acid (5.0 mL) was added dropwise to ice-bath cooled acetic anhydride (10 mL). The mixture was warmed to 50° C. for 15 min and cooled to 20° C. $H_2SO_4$ (3 drops) and 1.7 g (5.94 mmol) of N-[bis-(fluorophenyl)methyl]-1H-1,2,4-triazol-1-amine were added and the solution was heated at reflux for 2 hours. The solution was diluted with ethyl acetate, washed twice with water and once with brine, dried ($MgSO_4$) and stripped. Chromatography on silica gel ($CH_2Cl_2$) gave 750 mg of the desired product as a white solid, m.p. 108°–110° C.

EXAMPLE 5i

Preparation of
N-[2-(4-chlorophenyl)-1-(2,4-difluorophenyl)-2-hydroxyethyl]-1H-1,2,4-triazol-1-amine A solution of s-butyllithium (36 mL of a 1.4M hexane solution, 50.4 mmol) was added dropwise to 100 mL of a tetrahydrofuran solution of 10.8 g (50.6 mmol) of 1-(4-chlorobenzyloxy)-1-ethoxyethane cooled to −78° C. After stirring 15 min. a solution of 5.85 g (27.8 mmol) of N-[(2,4-difluorophenyl)-methylene]-1H-1,2,4-triazol-1-amine was added at a rate to keep the temperature below −60° C. The reaction mixture was stirred 10 min, quenched with aqueous $NH_4Cl$ and warmed to room temperature. The mixture was diluted with ethyl acetate, washed with water and brine, dried ($MgSO_4$) and concentrated to afford an oil. The oil was chromatographed on silica gel to isolate 4.9 g of the intermediate adduct as an oil. A portion of this material (2.0 g, 4.7 mmol) was dissolved in 100 mL of 1:1 tetrahydrofuran aqueous 2N HCl. The reaction mixture was stirred 1 hour, diluted with ethyl acetate and washed with aqueous $Na_2CO_3$, water and brine. Drying ($MgSO_4$) of the organic layer and removal of solvent gave a viscous oil which was chromatographed (ether) to give the desired product as a mixture of diastoreamers, m.p. 61°–76° C. A separation of the diastereomers was achieved by fractional crystallization from n-butyl chloride: Isomer A m.p. 174°–176° C.; Isomer B m.p. 131°–134° C.

EXAMPLE 5j

Preparation of
N-[2-(4-chlorophenoxy)-1-(4-fluorophenyl)ethyl]-1H-1,2,4-traizol-1-amine To a cooled (0°), stirred solution of N-[2-(4-chlorophenoxy)-1-(4-fluorophenyl)ethylidene]-1H-1,2,4-triazole-1-amine (3.0 g, 9.1 mmol) in 20 mL methanol and 20 mL dry N,N-dimethylformamide is added 0.3 g (9.1 mmol) sodium borohydride in two portions. The mixture is warmed to room temperature and stirred for 1 hour or until complete as indicated by TLC. Water (5 mL) is added and stirring is continued for an additional 30 min to destroy any unreacted sodium borohydride. The solution is stripped to an oil then diluted with 100 mL ethyl acetate. The organic solution is washed with 2×50 mL H$_2$O, 1×50 mL brine then dried over MgSO$_4$. The solution is then filtered and concentrated. The product so obtained can be purified by crystallization or chromatography.

EXAMPLE 5k

Preparation of
5-Chloro-α-(4-fluorophenyl)-N-(1H-1,2,4-triazol-1-yl)-2-pyridineethanamine A solution of n-butyllithium (15 mL, 1.6M, 14.4 mmol) in hexanes was added dropwise at −78° C. to 4.6 g (23.9 mmol) of 2-bromo-5-chloropyridine in 50 mL ether. After stirring 10 min, 3.0 g (15.7 mmol) of N-[(4-fluorophenyl)methylene]-1H, 1,2,4-triazol-1-amine in 60 mL of 5:1 ether-tetrahydrofuran was added quickly. The reaction mixture was stirred 30 min. quenched with aqueous NH$_4$Cl and warmed to room temperature. It was diluted with ethyl acetate and washed with water and brine. Drying (MgSO$_4$), removal of solvent and chromatography (gradient elution with 9:1 CH$_2$Cl$_2$/acetone to 1:1 CH$_2$Cl$_2$/acetone) on silica gel gave 1.4 g of the desired product, m.p. 106°-107° C.

EXAMPLE 51

Preparation of
N-[(5-Chloro-2-thienyl)-4-fluorophenyl)-methyl]-1H, 1,2,4-triazol-1-amine The preparation was carried out as described for Example 5k with 6.9 mL (27 mmol) of 1.6M n-butyllithium in hexanes, 5.38 g (27 mmol) 2-bromo-5-chlorothiophene and 4.08 g (21 mmol) of N-[(4-fluorophonyl)-methylene]-1H-1,2,4-triazol-1-amine to give 1.3 g of the desired product, m.p. 111°-120° C.

Following the procedures described earlier and exemplified by Examples 5a, 5b, 5c, 5f, 5g and 5h, compound in Table Va can be prepared.

TABLE Va

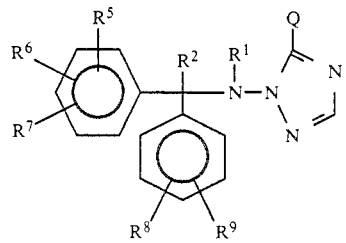

| Q | R$^1$ | R$^2$ | R$^5$ | R$^6$ | R$^7$ | R$^8$ | R$^9$ | Properties |
|---|---|---|---|---|---|---|---|---|
| H | H | H | H | H | 4-C$_6$H$_5$ | H | 4-F | |
| H | H | H | H | H | 4-F | H | 4-CF$_3$ | |
| H | H | H | H | H | 4-F | H | 2-CF$_3$ | m.p. 124-128° C. |
| H | H | H | H | H | 4-F | H | 3-CF$_3$ | m.p. 92-96° C. |
| H | H | H | H | H | 2-F | 4-F | 2-F | m.p. 98-105° C. |
| H | H | H | H | H | 4-Cl | H | 4-Cl | m.p. 138-140 ° C. |
| H | H | H | H | H | 2-CH=CH$_2$ | H | 4-F | m.p. 98-101° C. |
| H | H | H | H | H | 2-(CHBr—CH$_2$Br) | H | 4-F | m.p. 107-114° C. |
| H | H | H | H | H | 4-CH$_3$ | 4-Cl | 2-Cl | m.p. 86-93° C. |
| H | H | H | H | H | 4-OCH$_3$ | 4-Cl | 2-Cl | m.p. 136-139° C. |
| H | H | H | H | H | 2-F | H | 4-Cl | m.p. 110-114° C. |
| H | H | H | H | H | 3-CF$_3$ | 4-Cl | 2-Cl | oil, δ 7.83 (s, 1H, triazole C—H) |
| H | H | H | H | H | 4-F | 5-F | 3-F | m.p. 120-123° C. |
| H | H | H | H | H | 4-F | H | 3-F | m.p. 112-114.5° C. |
| H | H | H | H | H | 4-Cl | 4-F | 2-F | m.p. 118-123° C. |
| H | H | H | H | 3-Cl | 2-Cl | 4-Cl | 2-Cl | |
| H | H | H | H | H | 3-F | 4-Cl | 2-Cl | m.p. 100-104° C. |
| H | H | H | H | H | 4-F | 5-F | 2-F | m.p. 135-141° C. |
| H | H | H | H | H | 4-CN | H | 4-F | |
| H | H | H | H | H | 4-SCH$_3$ | H | 4-F | |
| H | H | H | 6-F | 4-F | 2-F | H | 4-Cl | |
| H | H | H | H | H | 4-SO$_2$CH$_3$ | H | 4-F | |
| H | H | H | H | H | 2-CF$_3$ | H | 4-Cl | m.p. 115-118° C. |
| H | H | H | H | H | 2-CF$_3$ | 4-Cl | 2-Cl | m.p. 165-171° C. |
| H | H | H | H | H | 2-F | 4-Cl | 2-Cl | m.p. 153-155° C. |
| H | H | H | H | H | 2-OCH$_3$ | H | 4-F | m.p. 140-144° C. |
| H | H | H | H | 5-Cl | 2-Cl | H | 4-F | m.p. 137-143° C. |
| H | H | H | H | H | 3-Cl | H | 4-F | oil, δ 7.79 (s, 1H triazole C—H) |
| H | H | H | H | 4-Cl | 3-Cl | 4-Cl | 2-Cl | m.p. 153-160° C. |
| H | H | H | H | 4-Cl | 2-Cl | H | 4-F | m.p. 121-123° C. |
| H | H | H | H | H | 4-F | H | 4-Cl | |
| H | H | H | H | H | 2-F | H | 4-F | m.p. 125-129° C. |
| H | H | H | H | H | 2-Cl | H | 4-F | m.p. 139-142° C. |
| H | H | H | H | 3-Cl | 2-Cl | H | 4-F | m.p. 129-133° C. |
| H | H | H | H | 4-F | 2-F | H | 4-F | |
| H | H | H | H | H | 4-CH$_3$ | H | 4-F | m.p. 154-155.5° C. |
| H | H | H | H | H | 4-OCH$_3$ | H | 4-F | |
| H | H | H | H | H | 4-NO$_2$ | 4-Cl | 2-Cl | oil. δ 8.19 (s, 1H triazole C—H) |
| H | H | H | H | 4-Cl | 2-CH$_3$ | H | 4-F | m.p. 109-111° C. |

TABLE Va-continued

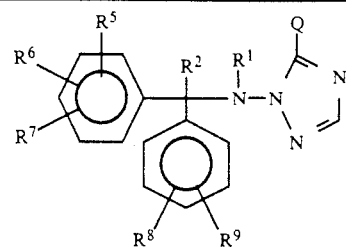

| Q | R¹ | R² | R⁵ | R⁶ | R⁷ | R⁸ | R⁹ | Properties |
|---|---|---|---|---|---|---|---|---|
| H | H | H | H | 4-F | 2-CH₃ | H | 4-F | m.p. 116–117° C. |
| H | H | H | H | 5-F | 3-F | H | 4-F | |
| H | H | H | H | 4-Cl | 2-Cl | H | 2-CH₃ | |
| H | H | H | H | 4-Cl | 2-Cl | H | 4-Cl | m.p. 109–114° C. |
| H | H | H | H | 4-Cl | 2-Cl | H | 3-Cl | oil, δ 7.92 (s, 2H triazole C—H) |
| H | H | H | H | 4-Cl | 2-Cl | H | 2-Cl | |
| H | H | H | H | 4-F | 2-CH₃ | 4-Cl | 2-Cl | m.p. 150–153° C. |
| H | H | H | H | 4-Cl | 2-CH₃ | 4-Cl | 2-Cl | m.p. 176–180° C. |
| H | H | H | H | H | 4-C₆H₅ | 4-Cl | 2-Cl | |
| H | H | H | H | H | 4-(4-Cl—C₆H₄) | 4-Cl | 2-Cl | |
| H | H | H | H | H | 4-C₆H₅O | H | 4-Cl | m.p. 76–84° C. |
| H | CH₃ | H | H | H | 4-C₆H₅ | H | 4-F | oil, δ 7.82 (s, 1H triazole C—H) |
| H | CH₃ | H | H | H | 4-F | H | 4-CF₃ | oil, δ 7.8 (s, 1H triazole C—H) |
| H | CH₃ | H | H | H | 4-F | H | 2-CF₃ | m.p. 81–87° C. |
| H | CH₃ | H | H | H | 4-F | H | 3-CF₃ | oil, δ 7.77 (s, 1H triazole C—H) |
| H | CH₃ | H | H | H | 2-F | 4-F | 2-F | m.p. 56–60° C. |
| H | CH₃ | H | H | H | H | H | H | m.p. 88–91° C. |
| H | CH₃ | H | H | H | 4-Cl | H | 4-Cl | m.p. 157–162° C. |
| H | CH₃ | H | H | H | 2-(CHBr—CH₂Br) | H | 4-F | |
| H | CH₃ | H | H | H | 4-CH₃ | 4-Cl | 2-Cl | m.p. 111–114° C. |
| H | CH₃ | H | H | H | 4-OCH₃ | 4-Cl | 2-Cl | |
| H | CH₃ | H | H | H | 2-OCH₃ | H | 4-F | m.p. 84–87° C. |
| H | CH₃ | H | H | 5-Cl | 2-Cl | H | 4-F | oil, δ 7.82 (s, 1H triazole C—H) |
| H | CH₃ | H | H | H | 3-Cl | H | 4-F | oil, δ 7.78 (s, 1H triazole C—H) |
| H | CH₃ | H | H | 4-Cl | 3-Cl | 4-Cl | 2-Cl | oil, δ 7.85 (s, 1H triazole C—H) |
| H | CH₃ | H | H | H | 2-F | H | 4-Cl | oil, δ 7.85 (s, 1H triazole C—H) |
| H | CH₃ | H | H | H | 3-CF₃ | 4-Cl | 2-Cl | oil, δ 7.81 (s, 1H triazole C—H) |
| H | CH₃ | H | H | H | 4-F | 5-F | 3-F | oil, δ 7.80 (s, 1H triazole C—H) |
| H | CH₃ | H | H | H | 4-F | H | 3-F | oil, δ 7.78 (s, 1H triazole C—H) |
| H | CH₃ | H | H | H | 4-Cl | 4-F | 2-F | oil, δ 7.85 (s, 1H triazole C—H) |
| H | CH₃ | H | H | 3-Cl | 2-Cl | 4-Cl | 2-Cl | |
| H | CH₃ | H | H | H | 3-F | 4-Cl | 2-Cl | |
| H | CH₃ | H | H | H | 4-F | 5-F | 2-F | oil, δ 7.55 (s, 1H triazole C—H) |
| H | CH₃ | H | H | H | 4-CN | H | 4-F | |
| H | CH₃ | H | H | H | 4-SCH₃ | H | 4-F | |
| H | CH₃ | H | 6-F | 4-F | 2-F | H | 4-Cl | |
| H | CH₃ | H | H | H | 4-SO₂CH₃ | H | 4-F | |
| H | CH₃ | H | H | H | 2-CF₃ | H | 4-Cl | m.p. 68–75° C. |
| H | CH₃ | H | H | 4-Cl | 2-Cl | H | 4-F | |
| H | CH₃ | H | H | H | 4-F | H | 4-Cl | |
| H | CH₃ | H | H | H | 4-F | H | 4-F | m.p. 107–108° C. |
| H | CH₃ | H | H | H | 2-F | H | 4-F | m.p. 90–93° C. |
| H | CH₃ | H | H | H | 2-Cl | H | 4-F | oil, δ 7.79 (s, 1H, triazole C—H) |
| H | CH₃ | H | H | 3-Cl | 2-Cl | H | 4-F | oil, δ 7.78 (s, 1H triazole C—H) |
| H | CH₃ | H | H | 4-F | 2-F | H | 4-F | |
| H | CH₃ | H | H | H | 4-CH₃ | H | 4-F | m.p. 118–121° C. |
| H | CH₃ | H | H | H | 4-OCH₃ | H | 4-F | m.p. 89–95° C. |
| H | CH₃ | H | H | H | 4-NO₂ | 4-Cl | 2-Cl | oil, δ 8.11 (s, 1H triazole C—H) |
| H | CH₃ | H | H | 4-Cl | 2-CH₃ | H | 4-F | m.p. 117–120° C. |
| H | CH₃ | H | H | 4-F | 2-CH₃ | H | 4-F | |
| H | CH₃ | H | H | 5-F | 3-F | H | 4-F | |
| H | CH₃ | H | H | 4-Cl | 2-Cl | H | 2-CH₃ | |
| H | CH₃ | H | H | 4-Cl | 2-Cl | H | 4-Cl | oil, δ 7.8 (s, 1H |

TABLE Va-continued

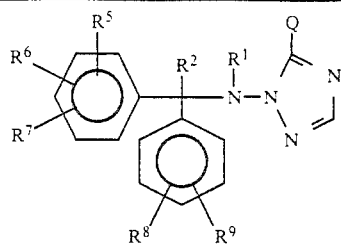

| Q | R¹ | R² | R⁵ | R⁶ | R⁷ | R⁸ | R⁹ | Properties |
|---|---|---|---|---|---|---|---|---|
| H | CH₃ | H | H | 4-Cl | 2-Cl | H | 3-Cl | oil, δ 7.83 (s, 1H triazole C—H) |
| H | CH₃ | H | H | H | 2-F | 4-Cl | 2-Cl | m.p. 98-102° C. |
| H | CH₃ | H | H | 4-Cl | 2-Cl | H | 2-Cl | |
| H | CH₃ | H | H | 4-F | 2-CH₃ | 4-Cl | 2-Cl | m.p. 114-116° C. |
| H | CH₃ | H | H | 4-Cl | 2-CH₃ | 4-Cl | 2-Cl | m.p. 122-130° C. |
| H | CH₃ | H | H | H | 4-C₆H₅ | 4-Cl | 2-Cl | |
| H | CH₃ | H | H | H | 4-(4-Cl-C₆H₄) | 4-Cl | 2-Cl | |
| H | CH₃ | H | H | H | 4-C₆H₅O | H | 4-Cl | oil, δ 7.89 (s, 1H triazole C—H) |
| H | (CH₂)₅CH₃ | H | H | 4-Cl | 2-Cl | H | 4-F | |
| H | CH₂CH=CH₂ | H | H | H | 4-F | H | 4-F | m.p. 78-85° C. |
| H | CH₂C₆H₅ | H | H | H | 4-F | H | 4-F | m.p. 155-162° C. |
| H | CH₂—CH=CH₂ | H | H | H | 4-F | H | 2-F | oil, δ 7.8 (s, 1H triazole C—H) |
| H | CH₂F | H | H | H | 4-F | H | 4-F | |
| H | CF₂H | H | H | H | 4-F | H | 4-F | |
| H | C(O)CH₃ | H | H | H | 4-F | H | 4-F | m.p. 110-114° C. |
| H | C(O)CH₃ | H | H | 4-Cl | 2-Cl | H | 4-Cl | m.p. 135-138° C. |
| H | CH₂CO₂C₂H₅ | H | H | H | 4-F | H | 4-F | m.p. 75-82° C. |
| H | CH₂CO₂CH₂C₆H₅ | H | H | H | 4-F | H | 4-F | oil, δ 7.8 (s, 1H triazole C—H) |
| H | C(O)OCH₃ | H | H | H | 4-F | H | 4-F | |
| H | C(O)OCH₃ | H | H | 4-C | | H | 4-Cl | |
| H | CH₂SCH₃ | H | H | H | 4-F | H | 4-F | m.p. 118-138° C. |
| H | CH₂OCH₃ | H | H | H | 4-F | H | 4-F | |
| H | CH₂OCH₃ | H | H | 4-Cl | 2-Cl | H | 4-F | |
| H | CH₂C≡CH | H | H | 4-Cl | 2-Cl | H | 4-F | oil, δ 7.9 (s, 1H triazole C—H) |
| H | cyclopropyl | H | H | 4-Cl | 2-Cl | H | 4-F | |
| H | CH₂-cyclopropyl | H | H | 4-Cl | 2-Cl | H | 4-F | |
| H | C₂H₅ | H | H | H | 4-F | H | 4-F | oil, δ 7.76 (s, 2H triazole C—H) |
| H | (CH₂)₃CH₃ | H | H | H | 4-F | H | 4-F | |
| H | CH₂CO₂H | H | H | H | 4-F | H | 4-F | m.p. 66-71° C. |
| H | CH₂CH=CHCl | H | H | 4-Cl | 2-Cl | H | 4-F | |
| H | CH₂CH=CH₂ | H | H | 4-Cl | 2-Cl | H | 4-F | oil, δ 7.7 (s, 2H triazole C—H) |
| H | CH₂CF₃ | H | H | 4-Cl | 2-Cl | H | 4-F | |
| H | C(O)NHCH₃ | H | H | 4-Cl | 2-Cl | H | 4-F | |
| H | C(O)OC(CH₃)₃ | H | H | 4-Cl | 2-Cl | H | 4-F | |
| H | CHO | H | H | 4-Cl | 2-Cl | H | 4-F | m.p. 145-153° C. |
| H | CHO | H | H | 4-F | 2-F | H | 4-F | |
| H | CH₂CH(CH₃)₂ | H | H | 4-Cl | 2-Cl | H | 4-F | |
| H | C(O)(CH₂)₃CH₃ | H | H | 4-Cl | 2-Cl | H | 4-F | |
| SCH₂SCN | CH₃ | H | H | 4-Cl | 2-Cl | H | 4-F | oil, δ 7.7 (s, 1H triazole C—H) |
| S(O)CH₂SCN | CH₃ | H | H | 4-Cl | 2-Cl | H | 4-F | Isomer A: m.p. 61-67° C. Isomer B: m.p. 57-61° C. |
| S(O)₂CH₃SCN | CH₃ | H | H | 4-Cl | 2-Cl | H | 4-F | m.p. 56-62° C. |
| SCH₃ | CH₃ | H | H | 4-Cl | 2-Cl | H | 4-F | |
| SCH₂CN | CH₃ | H | H | 4-Cl | 2-Cl | H | 4-F | m.p. 48-51° C. |
| S(O)CH₂CN | CH₃ | H | H | 4-Cl | 2-Cl | H | 4-F | oil, δ 7.4 (s, 1H triazole C—H) |
| S(O)₂CH₂CN | CH₃ | H | H | 4-Cl | 2-Cl | H | 4-F | m.p. 101-108° C. |
| I | CH₃ | H | H | 4-Cl | 2-Cl | H | 4-F | m.p. 108-114° C. |
| Br | CH₃ | H | H | 4-Cl | 2-Cl | H | 4-F | oil, δ 7.75 (s, 1H |

TABLE Va-continued

| Q | $R^1$ | $R^2$ | $R^5$ | $R^6$ | $R^7$ | $R^8$ | $R^9$ | Properties |
|---|---|---|---|---|---|---|---|---|
| | | | | | | | | triazole C—H) |
| F | $CH_3$ | H | H | 4-Cl | 2-Cl | H | 4-F | |
| CHO | $CH_3$ | H | H | 4-Cl | 2-Cl | H | 4-F | m.p. 174–175° C. |
| SH | H | H | H | H | 4-F | H | 4-F | |
| $CH_2SCN$ | H | H | H | H | 4-Cl | H | 4-Cl | |
| $SO_2CH_2SCN$ | H | H | H | 4-Cl | 2-Cl | H | 4-Cl | |
| $SCH_3$ | H | H | H | H | 4-F | H | 2-F | |
| $SCH_2CN$ | $CH_3$ | H | H | H | 4-Cl | H | 2-Cl | |
| $SO_2CH_2CN$ | $CH_3$ | H | H | H | 4-Cl | H | 2-Cl | |
| I | $CH_3$ | H | H | H | 4-F | H | 4-F | |
| Br | $CH_3$ | H | H | H | 4-F | H | 4-F | |
| Cl | $CH_3$ | H | H | H | 4-F | H | 4-F | |
| H | H | $CF_3$ | H | H | 4-F | H | H | m.p. 102–108° C. |
| H | $CH_3$ | $CF_3$ | H | H | 4-F | H | H | oil, δ 7.7 (s, 1H triazole C—H) |
| H | H | $CF_3$ | H | 4-Cl | 2-Cl | H | H | m.p. 136–142° C. |
| H | $CH_3$ | $CF_3$ | H | 4-Cl | 2-Cl | H | H | oil, δ 8.0 (s, 1H triazole C—H) |
| H | H | $CH_2CN$ | H | H | 4-F | H | 4-F | m.p. 147–157° C. |
| H | $CH_3$ | $CH_2CN$ | H | H | 4-F | H | 4-F | |
| $SCH_3$ | H | H | H | H | 4-F | 4-Cl | 2-Cl | oil, δ 7.9 (s, 1H triazole C—H) |
| H | $CH_3$ | $CH_3$ | H | H | 4-F | H | 4-F | oil, δ 7.75 (s, 1H triazole C—H) |
| H | H | $CH_3$ | H | H | 4-F | 4-Cl | 2-Cl | m.p. 104–108° C. |
| H | $CH_3$ | $CH_3$ | H | H | 4-F | 4-Cl | 2-Cl | m.p. 118–119° C. |
| H | H | $CH_3$ | H | H | 4-Cl | 4-Cl | 2-Cl | |
| H | $CH_3$ | CH | H | H | 4-Cl | 4-Cl | 2-Cl | |
| H | H | $(CH_2)_3CH_3$ | H | H | 4-F | H | 4-F | m.p. 152–154° C. |
| H | $CH_3$ | $(CH_2)_3CH_3$ | H | H | 4-F | H | 4-F | m.p. 110–120° C. |
| H | H | cyclopropyl | H | H | 4-Cl | H | 4-Cl | |
| H | $CH_3$ | cyclopropyl | H | H | 4-Cl | H | 4-Cl | |
| H | H | CHO | H | 4-Cl | 2-Cl | H | 4-F | |
| H | $CH_3$ | CHO | H | 4-Cl | 2-Cl | H | 4-F | |
| H | H | $CH_2OH$ | H | 4-Cl | 2-Cl | H | 4-F | |
| H | $CH_3$ | $CH_2OH$ | H | 4-Cl | 2-Cl | H | 4-F | |
| H | H | $CH_2F$ | H | H | 4-F | H | 4-F | |
| H | $CH_3$ | $CH_2F$ | H | H | 4-F | H | 4-F | |
| H | H | CN | H | 4-Cl | 2-Cl | H | 4-F | |
| H | $CH_3$ | CN | H | 4-Cl | 2-Cl | H | 4-F | |
| H | H | CN | H | 4-Cl | 2-Cl | H | 4-Cl | |
| H | $CH_3$ | CN | H | 4-Cl | 2-Cl | H | 4-Cl | |
| H | H | $CH=CH_2$ | H | H | 4-Cl | H | 4-Cl | |
| H | $CH_3$ | $CH=CH_2$ | H | H | 4-Cl | H | 4-Cl | |
| H | H | C≡CH | H | H | 4-Cl | H | 4-Cl | |
| H | $CH_3$ | C≡CH | H | H | 4-Cl | H | 4-Cl | |
| H | H | C≡$CCH_3$ | H | H | 4-Cl | H | 4-Cl | |
| H | $CH_3$ | C≡$CCH_3$ | H | H | 4-Cl | H | 4-Cl | |
| H | H | $CH_2CH=CHCH_3$ | H | H | 4-Cl | H | 4-Cl | |
| H | $CH_3$ | $CH_2CH=CHCH_3$ | H | H | 4-Cl | H | 4-Cl | |
| H | H | H | 6-Cl | 4-Cl | 2-Cl | H | 4-F | |
| H | $CH_3$ | H | 6-Cl | 4-Cl | 2-Cl | H | 4-F | |
| H | H | H | 6-Cl | 4-Cl | 2-Cl | 4-Cl | 2-Cl | |
| H | $CH_3$ | H | 6-Cl | 4-Cl | 2-Cl | 4-Cl | 2-Cl | |
| H | H | H | H | 4-Cl | 2-CN | H | 4-Cl | |
| H | $CH_3$ | H | H | 4-Cl | 2-CN | H | 4-Cl | |
| $CH_3$ | $CH_3$ | H | H | H | 4-$C_6H_5$ | H | 4-F | oil, δ 7.7 (s, 1H triazole C—H) |
| $CH_3$ | $CH_3$ | H | H | H | 4-F | H | 4-$CF_3$ | oil, δ 7.6 (s, 1H triazole C—H) |
| $CH_3$ | H | $CH_3$ | H | H | 4-F | H | 4-F | oil, δ 7.6 (s, 1H triazole C—H) |

TABLE Va-continued

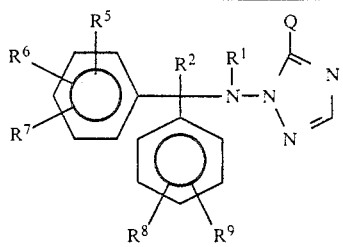

| Q | R¹ | R² | R⁵ | R⁶ | R⁷ | R⁸ | R⁹ | Properties |
|---|---|---|---|---|---|---|---|---|
| H | H | H | H | 4-Cl | 3-Cl | H | 4-F | m.p. 100–106° C. |
| H | CH₃ | H | H | 4-Cl | 3-Cl | H | 4-F | m.p. 120–125° C. |
| H | H | H | H | 4-Cl | 2-Cl | H | 4-CN | m.p. 140–150° C. |
| H | CH₃ | H | H | 4-Cl | 2-Cl | H | 4-CN | oil, δ 7.83 (s, 1H triazole C—H) |
| H | H | H | H | 4-Cl | 2-CN | H | 4-F | |
| H | CH₃ | H | H | 4-Cl | 2-CN | H | 4-F | |
| H | H | H | H | 4-CN | 2-Cl | H | 4-F | |
| H | CH₃ | H | H | 4-CN | 2-Cl | H | 4-F | |
| H | CH₂CO₂CH₂C₆H₅ | H | H | 4-Cl | 2-Cl | H | 4-F | oil, δ 7.9 (s, 1H triazole C—H) |
| H | C₂H₅ | H | H | 4-Cl | 2-Cl | H | 4-F | oil, δ 7.9 (s, 1H triazole C—H) |
| H | CH₂—CH=CH₂ | H | H | H | 4-C₆H₃—O | H | 4-Cl | oil, δ 7.76 (s, 1H triazole C—H) |
| H | H | H | H | 4-Cl | 2-Cl | H | 4-CH₃—S | oil, δ 7.79 (s, 1H triazole C—H) |
| H | CH₃ | H | H | 4-Cl | 2-Cl | H | 4-CH₃—S | oil, δ 7.8 (s, 1H triazole C—H) |
| H | H | H | H | 6-F | 2-F | H | 4-F | m.p. 116–122° C. |
| H | CH₃ | H | H | 6-F | 2-F | H | 4-F | oil, δ 8.07 (s, 1H triazole C—H) |
| H | CH₂C(Br)=CH₂ | H | H | 6-F | 2-F | H | 4-F | oil, δ 8.10 (s, 1H triazole C—H) |
| H | H | H | H | 4-Cl | 2-Cl | H | 4-CH₃SO₂ | m.p. 103–109° C. |
| H | CH₃ | H | H | 4-Cl | 2-Cl | H | 4-CH₃SO₂ | m.p. 162–165° C. |
| H | H | H | 5-Cl | 4-Cl | 2-Cl | H | 4-F | m.p. 136–140° C. |
| H | CH₃ | H | 5-Cl | 4-Cl | 2-Cl | H | 4-F | oil, δ 7.98 (s, 1H triazole C—H) |
| H | 4-F—C₆H₄ | H | H | 4-Cl | 2-Cl | H | 4-Cl | |
| H | 4-CN—C₆H₄ | H | H | 4-Cl | 2-Cl | H | 4-F | |

Following the procedures described earlier and exemplified by Examples 5a, 5b, 5c, 5d, 5e, 5f, 5g, 5h, 5i, 5j, 5k and 5l, compounds in Table Vb can be prepared.

TABLE Vb

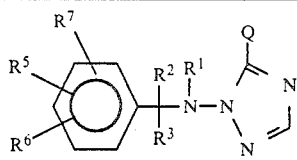

| Q | R¹ | R² | R³ | R⁵ | R⁶ | R⁷ | Properties |
|---|---|---|---|---|---|---|---|
| H | CH₃ | H | 3-thienyl | H | H | 4-F | oil, δ 7.8 (s, 1H triazole C—H) |
| H | H | H | 3-thienyl | H | 4-Cl | 2-Cl | |
| H | H | H | 2-thienyl | H | 4-Cl | 2-Cl | |
| H | CH₃ | H | 3-thienyl | H | 4-Cl | 2-Cl | |
| H | CH₃ | H | 2-thienyl | H | 4-Cl | 2-Cl | |
| H | H | H | 4-pyridyl | H | H | H | m.p. 140–142° C. |
| H | CH₃ | H | 4-pyridyl | H | H | H | |

TABLE Vb-continued

| Q | R¹ | R² | R³ | | R⁵ | R⁶ | R⁷ | Properties |
|---|----|----|----|---|----|----|----|------------|
| H | H | H | 3-pyridyl | | H | H | H | m.p. 127–129° C. |
| H | CH₃ | H | 3-pyridyl | | H | H | H | |
| H | H | H | 3-pyridyl | | H | 4-Cl | 2-Cl | m.p. 74–76° C. |
| H | CH₃ | H | 3-pyridyl | | H | 4-Cl | 2-Cl | |
| H | H | H | 2-pyridyl | | H | 4-Cl | 2-Cl | m.p. 56–61° C. |
| H | CH₃ | H | 2-pyridyl | | H | 4-Cl | 2-Cl | oil, δ 7.84 (s, 1H triazole C—H) |
| H | H | H | 2-(5-Cl-thienyl) | | H | H | 4-F | m.p. 111–120° C. |
| H | H | H | 3-(2,5-diCl-thienyl) | | H | H | 4-F | |
| H | CH₃ | H | 2-(5-Cl-thienyl) | | H | H | 4-Cl | |
| H | CH₃ | H | 3-(2,5-diCl-thienyl) | | H | H | 4-Cl | |
| H | H | CN | (CH₂)₃—CH₃ | | H | H | 4-Cl | |
| H | H | CN | (CH₂)₃CH₃ | | H | 4-Cl | 2-Cl | |
| H | H | CN | (CH₂)₃CH₃ | | H | H | 4-C₆H₅ | |
| H | CH₃ | CN | (CH₂)₃CH₃ | | H | H | 4-Cl | |
| H | CH₃ | CN | (CH₂)₃CH₃ | | H | 4-Cl | 2-Cl | |
| H | CH₃ | CN | (CH₂)₃CH₃ | | H | H | 4-C₆H₅ | |
| H | H | CF₃ | (CH₂)₃CH₃ | | H | H | H | m.p. 64–70° C. |
| H | H | H | cyclopentyl | | H | H | 4-F | m.p. 88–92° C. |
| H | CH₃ | H | cyclopentyl | | H | H | 4-F | oil, δ 8.01 (s, 1H trizole C—H) |
| H | H | H | cyclopentyl | | H | 4-Cl | 2-Cl | m.p. 115–118° C. |
| H | CH₃ | H | cyclopentyl | | H | 4-Cl | 2-Cl | oil, δ 8.02 (s, 1H triazole C—H) |
| H | H | H | cyclohexyl | | H | H | 4-F | m.p. 108–111° C. |
| H | CH₃ | H | cyclohexyl | | H | H | 4-F | oil, δ 8.02 (s, 1H triazole C—H) |
| H | H | H | cyclohexyl | | H | 4-Cl | 2-Cl | m.p. 105–109° C. |
| H | CH₃ | H | cyclohexyl | | H | 4-Cl | 2-Cl | oil, δ 8.02 (s, 1H triazole C—H) |
| H | H | H | (CH₂)₂—CH₃ | | H | 4-Cl | 2-Cl | oil, δ 7.81 (s, 1H trizole C—H) |
| H | CH₃ | H | (CH₂)₂—CH₂ | | H | 4-Cl | 2-Cl | oil, δ 7.97 (s, 1H triazole C—H) |
| H | H | H | (CH₂)₃—CH₃ | | H | 4-Cl | 2-Cl | |
| H | CH₃ | H | (CH₂)₃—CH₃ | | H | 4-Cl | 2-Cl | |
| H | H | H | cyclproryl | | H | H | 4-F | oil, δ 7.80 (s, 2H triazole C—H) |
| H | CH₃ | H | cyclopropyl | | H | H | 4-F | |
| H | H | H | cyclopropyl | | H | 4-Cl | 2-Cl | oil, δ 7.82 (s, 1H triazole C—H) |
| H | CH₃ | H | cyclopropyl | | H | 4-Cl | 2-Cl | oil, δ 7.95 (s, 1H triazole C—H) |
| H | H | H | CH(CH₃)cyclopropyl | | H | H | 4-F | |
| H | CH₃ | H | CH(CH₃)cyclopropyl | | H | H | 4-F | |
| H | H | H | 3-(2,5-diCl-thienyl) | | H | H | 4-F | m.p. 90–94° C. |
| H | CH₃ | H | 3-(2,5-diCl-thienyl) | | H | H | 4-F | oil, δ 7.81 (s, 1H triazole C—H) |
| H | H | H | 2-(5-Cl-thienyl) | | H | 4-Cl | 2-Cl | oil, δ 7.85 (s, 1H triazole C—H) |
| H | CH₃ | H | 2-(5-Cl-thienyl) | | H | 4-Cl | 2-Cl | oil, δ 7.82 (s, 1H triazole C—H) |
| H | H | H | 1-(4-Cl—C₆H₄)-vinyl | | H | 4-F | 2-F | m.p. 88–92° C. |
| H | CH₃ | H | 1-(4-Cl—C₆H₄)-vinyl | | H | 4-F | 2-F | oil, δ 7.9 (s, 1H triazole C—H) |
| H | H | H | 1-(4-F—C₆H₄)-vinyl | | H | 4-F | 2-F | m.p. 85–88° C. |
| H | CH₃ | H | 1-(4-F—C₆H₄)-vinyl | | H | 4-F | 2-F | oil, δ 7.9 (s, 1H triazole C—H) |
| H | H | H | 1-(4-CN—C₆H₄)-vinyl | | H | 4-F | 2-F | |
| H | CH₃ | H | 1-(4-CN—C₆H₄)-vinyl | | H | 4-F | 2-F | |
| H | H | H | 1-(2,4-diF—C₆H₃)-vinyl | | H | 4-F | 2-F | |
| H | H | H | 1-(2,4-diCl—C₆H₃)-vinyl | | H | 4-F | 2-F | |
| H | H | H | 1-(4-CF₃—C₆H₄)-vinyl | | H | 4-F | 2-F | |
| H | H | H | 1-(4-CH₃O—C₆H₄)-vinyl | | H | 4-F | 2-F | |
| H | H | H | 1-(4-Br—C₆H₄)-vinyl | | H | 4-F | 2-F | |
| H | H | H | 1-C₆H₅-vinyl | | H | 4-F | 2-F | |
| H | H | H | 1-(1,4-diF—C₆H₃)-vinyl | | H | 4-Cl | 2-Cl | |
| H | H | H | 1-(3-Cl—C₆H₄)-vinyl | | H | 4-Cl | 2-Cl | |
| H | H | H | 1-(4-CN—C₆H₄)-vinyl | | H | H | 4-F | |
| H | H | H | 1-(2,4-diF—C₆H₃)-vinyl | | H | H | 4-F | |
| H | H | H | 1-(4-F—C₆H₄)-vinyl | | H | H | 4-CN | |
| H | H | H | 1-(4-F—C₆H₄)-vinyl | | H | H | 4-CH₃O | |
| H | H | H | 4-Cl—C₆H₄—CH(CH₃)— | | H | 4-F | 2-F | Isomer A: m.p. 95–97° C. |

TABLE Vb-continued

| Q | $R^1$ | $R^2$ | $R^3$ | | $R^5$ | $R^6$ | $R^7$ | Properties |
|---|---|---|---|---|---|---|---|---|
| H | H | H | 4-F—$C_6H_4$—CH($CH_3$)— | | H | 4-F | 2-F | Isomer B: m.p. 83–85° C.<br>Isomer A: m.p. 115–116° C.<br>Isomer B: m.p. 60–61° C. |
| H | H | H | 4-F—$C_6H_4$—CH($C_2H_5$)— | | H | 4-F | 2-F | Isomer A: m.p. 127–131° C.<br>Isomer B: oil, δ 7.73<br>(s, 1H triazole C—H) |
| H | H | H | 2,4-diF—$C_6H_3$—CH($CH_3$)— | | H | 4-F | 2-F | |
| H | H | H | 2,4-diCl—$C_6H_3$—CH($CH_3$)— | | H | 4-F | 2-F | |
| H | H | H | 4-$CF_3$—$C_6H_4$—CH($CH_3$)— | | H | 4-F | 2-F | |
| H | H | H | 4-$CH_3O$—$C_6H_4$—CH($CH_3$)— | | H | 4-F | 2-F | |
| H | H | H | 4-Br—$C_6H_4$—CH($CH_3$)— | | H | 4-F | 2-F | |
| H | H | H | $C_6H_5$—CH($CH_3$)— | | H | 4-F | 2-F | |
| H | H | H | 2,4-diF—$C_6H_3$—CH($CH_3$)— | | H | 4-F | 2-F | |
| H | H | H | 3-Cl—$C_6H_4$—CH($CH_3$)— | | H | 4-Cl | 2-Cl | |
| H | H | H | 4-CN—$C_6H_4$—CH($CH_3$)— | | H | H | 4-F | |
| H | H | H | 2,4-diF—$C_6H_3$—CH($CH_3$)— | | H | H | 4-F | |
| H | H | H | 4-F—$C_6H_4$—CH($CH_3$)— | | H | H | 4-CN | |
| H | H | H | 4-F—$C_6H_4$—CH($CH_3$)— | | H | 4-CN | 2-F | |
| H | H | H | 4-Cl—$C_6H_4$—CH(OH)— | | H | 4-Cl | 2-Cl | |
| H | H | H | 4-F—$C_6H_4$—CH(OH)— | | H | 4-F | 2-F | |
| H | $CH_3$ | H | 4-Cl—$C_6H_4$—CH(OH)— | | H | 4-F | 2-F | |
| H | $CH_3$ | H | 4-Cl—$C_6H_4$—CH(OH)— | | H | 4-F | 2-F | |
| H | H | H | 4-Cl—$C_6H_4$—CH($SCH_3$)— | | H | 4-F | 2-F | Isomer A:<br>m.p. 106–107° C.<br>Isomer B: oil,<br>δ 7.8<br>(s, 1H<br>triazole C—H) |
| H | $CH_3$ | H | 4-Cl—$C_6H_4$—CH($SCH_3$)— | | H | 4-F | 2-F | Isomer A: oil,<br>δ 8.3 (s, 1H<br>triazole C—H)<br>Isomer B:<br>m.p. 111–115° C. |
| H | H | H | t-butyl | | H | H | 4-Cl | m.p. 134–135° C. |
| H | $CH_3$ | H | t-butyl | | H | H | 4-Cl | m.p. 78–81° C. |
| H | $CH_2$—CH=$CH_2$ | H | t-butyl | | H | H | 4-Cl | m.p. 78–80° C. |
| H | H | H | 4-F—$C_6H_4$—CH($OCH_3$)— | | H | H | 4-F | Isomer A:<br>m.p. 142–143° C.<br>Isomer B: oil,<br>δ 7.8 (s, 1H<br>triazole C—H) |
| H | H | H | 4-F—$C_6H_4$—CH($OCH_3$)— | | H | 4-F | 2-F | oil, δ 7.8<br>(2s, 1H<br>triazole C—H) |
| H | H | H | 4-F—$C_6H_4$—CH($OCH_3$)— | | H | 4-Cl | 2-Cl | m.p. 105–124° C. |
| H | $CH_3$ | H | 4-F—$C_6H_4$—CH($OCH_3$)— | | H | 4-Cl | 2-F | Isomer A: oil,<br>δ 8.2 (s, 1H<br>triazole C—H)<br>Isomer B: oil,<br>δ 8.05 (s, 1H<br>triazole C—H) |
| H | $CH_3$ | H | 4-F—$C_6H_4$—CH($OCH_3$)— | | H | 4-Cl | 2-F | Isomer A: oil,<br>δ 8.2 (s, 1H<br>triazole C—H)<br>Isomer B: oil,<br>δ 8.0 (s, 1H<br>triazole C—H) |
| H | H | H | 2-(4-Cl—$C_6H_4$)-vinyl(cis) | | H | H | 4-F | m.p. 115–117° C. |
| H | $CH_3$ | H | 2-(4-Cl—$C_6H_4$)-vinyl(cis) | | H | H | 4-F | oil, δ 7.8<br>(2s, 2H<br>triazole C—H) |
| H | H | H | 2-(4-Cl—$C_6H_4$)-vinyl(trans) | | H | 4-F | 2-F | oil, δ 7.92<br>(s, 1H<br>triazole C—H) |
| H | $CH_3$ | H | 2-(4-Cl—$C_6H_4$)-vinyl(trans) | | H | 4-F | 2-F | |
| H | H | H | 4-Cl—$C_6H_4$—$(CH_2)_2$— | | H | 4-F | 2-F | m.p. 104–106° C. |
| H | $CH_3$ | H | 4-Cl—$C_6H_4$—$(CH_2)_2$— | | H | 4-F | 2-F | |
| H | H | H | 2,4-diF—$C_6H_3$—$CH_2$—CH($CH_3$)— | | H | H | 4-F | |
| H | $CH_3$ | H | 2,4-diF—$C_6H_3$—CH($CH_3$)— | | H | H | 4-F | |
| H | H | H | 2,4-diF—$C_6H_3$—CH($CH_3$)—$CH_3$— | | H | H | 4-F | |
| H | $CH_3$ | H | 2,4-diF—$C_6H_3$—CH($CH_3$)—$CH_3$— | | H | H | 4-F | |
| H | $CH_3$ | H | $C_6H_5$—CH($SCH_3$)$_3$— | | H | 4-F | 2-F | Isomer A:<br>m.p. 148–150° C. |

TABLE Vb-continued

| Q | R¹ | R² | R³ | | R⁵ | R⁶ | R⁷ | Properties |
|---|---|---|---|---|---|---|---|---|
| H | H | H | C₆H₅—CH(SCH₃)— | | H | 4-F | 2-F | Isomer B: m.p. 101–104° C. oil, δ 7.75 (2s, 1H triazole C—H) |
| H | CH₃ | H | 4-Cl—C₆H₄—CH(CH₃)— | | H | 4-F | 2-F | oil, δ 8.0 and 8.2 (2s, 1H triazole C—H) |
| H | CH₃ | H | 4-F—C₆H₄—CH(CH₃)— | | H | 4-F | 2-F | oil, 8.0 and 8.2 (2s, 1H triazole C—H) |
| H | H | H | 3,5-diCl-3-pyridyl- | | H | H | 4-Cl | m.p. 45–50° C. |
| H | CH₃ | H | 3,5-diCl-3-pyridyl- | | H | H | 4-Cl | m.p. 50–53° C. |
| H | H | H | 3,5-diCl-2-pyridyl- | | H | H | 4-F | oil, δ 7.9 (s, 1H triazole C—H) |
| H | CH₃ | H | 3,5-diCl-3-pyridyl- | | H | H | 4-F | oil, δ 7.95 (s, 1H triazole C—H) |
| H | C₂H₅ | H | 3,5-diCl-3-pyridyl | | H | H | 4-F | m.p. 98–102° C. |
| H | —CH₂CH=CH₂ | H | 3,5-diCl-3-pyridyl | | H | H | 4-F | oil, δ 7.9 (s, 1H triazole C—H) |
| H | H | H | 4-n-butyl-5-Cl-2-pyridyl | | H | 4-Cl | 2-Cl | oil, δ 7.87 (s, 1H triazole C—H) |
| H | CH₃ | H | 5-Cl-2-pyridyl | | H | 4-Cl | 2-Cl | oil, δ 7.85 (s, 1H triazole C—H) |
| H | H | H | 5-Cl-2-pyridyl | | H | 4-Cl | 2-Cl | m.p. 92–96° C. |
| H | CH₃ | H | 5-Cl-2-pyridyl | | H | H | 4-F | m.p. 127–129° C. |
| H | H | H | 5-Cl-2-pyridyl | | H | H | 4-F | m.p. 106–107° C. |
| H | CH₃ | H | 5-Cl-2-pyridyl | | H | 4-F | 2-F | m.p. 97–100° C. |
| H | H | H | 5-Cl-2-pyridyl | | H | 4-F | 2-F | oil, δ 7.8 (s, 2H triazole C—H) |
| H | CH₃ | H | 3,5-diCl-2-pyridyl | | H | 4-F | 2-F | m.p. 99–102° C. |
| H | H | H | 3,5-diCl-2-pyridyl | | H | 4-F | 2-F | oil, δ 7.95 (s, 1H triazole C—H) |
| H | CH₃ | H | 2,6-diF-3-pyridyl | | H | H | 4-F | oil, δ 7.9 (s, 1H triazole C—H) |
| H | H | H | 2,6-diF-3-pyridyl | | H | H | 4-F | m.p. 138–142° C. |
| H | CH₃ | H | 5-Cl-2-pyridyl | | H | H | 4-CN | |
| H | H | H | 5-CN-2-pyridyl | | H | 4-Cl | 2-Cl | |
| H | CH₃ | H | 5-CN-2-pyridyl | | H | 4-Cl | 2-Cl | |
| H | H | H | 4-F—C₆H₄—CH₂—CF₂— | | H | H | 4-Cl | |
| H | CH₃ | H | 4-F—C₆H₄—CF₂—CH₂— | | H | H | 4-Cl | |
| H | H | H | 4-F—C₆H₄—CH(Cl)—CH(CH₃)— | | H | H | 4-Cl | |
| H | H | H | 4-Cl—C₆H₄—O—CH₂— | | H | 4-F | 2-F | |
| H | CH₃ | H | 4-Cl—C₆H₄—O—CH₂— | | H | 4-F | 2-F | |
| H | H | H | 4-Cl—C₆H₄—S—CH₂ | | H | 4-F | 2-F | |
| H | CH₃ | H | 4-Cl—C₆H₄—S—CH₂ | | H | 4-F | 2-F | |
| H | H | H | 4-CN—C₆H₄—O—CH(CH₃)— | | H | 4-Cl | 2-Cl | |
| H | CH₃ | H | 4-CN—C₆H₄—O—CH(CH₂)— | | H | 4-Cl | 2-Cl | |
| H | H | H | 3-F—C₆H₄—S—CH₂ | | H | 4-Cl | 2-Cl | |
| H | H | H | n-butyl | | H | H | 4-F | oil, δ 7.8 (s, 1H triazole C—H) |
| H | H | H | 4-Cl—C₆H₄—C(CH₃)₂— | | H | 4-F | 2-F | |
| H | CH₃ | H | 4-Cl—C₆H₄—C(CH₃)₂— | | H | 4-F | 2-F | |
| H | 4-NO₂—C₆H₄ | H | CH₃ | | H | 4-Cl | 2-Cl | |
| H | 4-NO₂—C₆H₄— | H | C₂H₅ | | H | 4-Cl | 2-Cl | |
| H | 4-F—C₆H₄— | H | CH₃ | | H | 4-Cl | 2-Cl | |
| H | 4-Cl—C₆H₄— | H | CH₃ | | H | 4-Cl | 2-Cl | |
| H | H | H | (CH₂)₃CH₃ | | H | H | 4-CF₃ | m.p. 47–49° C. |
| H | CH₃ | H | (CH₂)₃CH₃ | | H | H | 4-CF₃ | |
| H | CH₃ | H | (CH₂)₃CH₃ | | H | H | 4-F | oil, δ 7.43 (s, 1H triazole C—H) |

TABLE Vb-continued

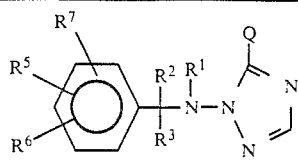

| Q | R¹ | R² | R³ | | R⁵ | R⁶ | R⁷ | Properties |
|---|---|---|---|---|---|---|---|---|
| H | H | H | (CH₂)₃CH₃ | | H | H | 4-F | oil, δ 7.8 (s, 1H triazole C—H) |
| H | CH₃ | CF₃ | (CH₂)₃CH₃ | | H | H | H | oil, δ 8.0 (s, 1H triazole C—H) |
| H | H | H | CF₂CF₃ | | H | H | 4-F | |
| H | CH₃ | H | CF₂CF₃ | | H | H | 4-F | |
| H | H | H | cyclohexyl | | H | H | 4-Cl | |
| H | CH₃ | H | cyclohexyl | | H | H | 4-Cl | |
| H | H | H | CH(CH₃)cyclopropyl | | H | 4-Cl | 2-Cl | |
| H | CH₃ | CN | CH(CH₃)cyclopropyl | | H | 4-Cl | 2-Cl | |
| H | H | H | CH₂-cyclopentyl | | H | 4-Cl | 2-Cl | |
| H | CH₃ | H | CH₂-cyclopentyl | | H | 4-Cl | 2-Cl | |
| H | H | H | CH₂-cyclohexyl | | H | 4-Cl | 2-Cl | |
| H | CH₃ | H | CH₂-cyclohexyl | | H | 4-Cl | 2-Cl | |
| I | CH₃ | H | 1-(4-F—C₆H₄)-vinyl | | H | H | 4-F | |
| H | CH₂CH=CH₂ | H | 1-(4-F—C₆H₄)-vinyl | | H | H | 4-F | oil, δ 7.75 (s, 1H triazole C—H) |
| H | H | H | 4-F—C₆H₄—CH₂ | | H | H | 4-F | m.p. 116-117° C. |
| H | CH₃ | H | 4-F—C₆H₄—CH₂ | | H | H | 4-F | m.p. 81-86° C. |
| H | allyl | H | 4-F—C₆H₄—CH(CH₃) | | H | H | 4-F | |
| H | H | H | 1-(4-F—C₆H₄)-vinyl | | H | H | 4-F | |
| H | CH₃ | H | 4-F—C₆H₄—CH(CH₃) | | H | H | 4-F | oil, δ 8.0 and 8.5 (2s, 1H triazole C—H) |
| H | H | H | 1-(4-Cl—C₆H₄)-vinyl | | H | H | 4-Cl | |
| H | H | H | 4-F—C₆H₄—CH(CH₃) | | H | 4-Cl | 2-Cl | |
| H | CH₃ | H | 4-F—C₆H₄—CH(CH₃) | | H | 4-Cl | 2-Cl | |
| H | H | CF₃ | C₆H₅—CH₂ | | H | 4-Cl | 2-Cl | |
| H | CH₃ | CF₃ | C₆H₅—CH₂ | | H | 4-Cl | 2-Cl | |
| H | H | H | 2,4-diCl—C₆H₃—CH(CH₃) | | H | H | 4-F | |
| H | CH₃ | H | 2,4-diCl—C₆H₃—CH(CH₃) | | H | H | 4-F | |
| H | CH₃ | H | 1-(4-Cl—C₆H₄)-vinyl | | H | H | 4-F | |
| H | CH₃ | CH₃ | 1-(4-F—C₆H₄)-vinyl | | H | H | 4-F | |
| H | H | H | 1-(2,4-diCl—C₆H₃)-vinyl | | H | H | 4-F | m.p. 106-110° C. |
| H | CH₃ | H | 1-(2,4-diCl—C₆H₃)-vinyl | | H | H | 4-F | |
| H | H | CH₃ | 1-(4-F—C₆H₄)-vinyl | | H | 4-Cl | 2-Cl | |
| H | H | CF₃ | 2,4-di-Cl—C₆H₃—CH₂ | | H | H | H | m.p. 129-130° C. |
| H | CH₃ | CF₃ | 2,4-di-Cl—C₆H₃—CH₂ | | H | H | H | oil, δ 8.3 (s, 1H triazole C—H) |
| H | CH₃ | H | 1-(4-F—C₆H₄)-vinyl | | H | 4-Cl | 2-Cl | |
| H | CH₃ | H | 1-(4-F—C₆H₄)-vinyl | | H | H | 4-F | |
| H | H | H | 4-F—C₆H₄—CH₂ | | H | 4-Cl | 2-Cl | m.p. 86-90° C. |
| H | CH₃ | H | 4-F—C₆H₄—CH₂ | | H | 4-Cl | 2-Cl | oil, δ 8.07 (s, 1H triazole C—H) |
| H | H | H | 2-(2,4-diCl—C₆H₃)-vinyl | | H | H | 4-F | |
| H | CH₃ | H | 2-(2,4-diCl—C₆H₃)-vinyl | | H | H | 4-F | |
| H | H | H | 4-F—C₆H₄—CF₂ | | H | H | 4-Cl | |
| H | CH₃ | H | 4-F—C₆H₄—CF₂ | | H | H | 4-Cl | |
| H | H | H | 1-(4-F—C₆H₄)-vinyl | | H | 4-Cl | 2-Cl | m.p. 110-113° C. |
| H | CH₃ | H | 1-(4-F—C₆H₄)-vinyl | | H | 4-Cl | 2-Cl | oil, δ 7.95 (s, 1H triazole C—H) |
| H | H | H | 1-(4-F—C₆H₄)-vinyl | | H | H | 4-Cl | |
| H | CH₃ | H | 1-(4-F—C₆H₄)-vinyl | | H | H | 4-Cl | |
| H | H | H | 4-F—C₆H₄—CH(n-propyl) | | H | H | 4-Cl | |
| H | CH₃ | H | 4-F—C₆H₄—CH(n-propyl) | | H | H | 4-Cl | |
| H | CH₃ | H | CH₃ | | H | H | 4-F | m.p. 34-42° C. |
| H | CH₂—C₆H₅ | H | CH₃ | | H | H | 4-F | oil, δ 7.9 (s, 1H triazole C—H) |
| H | CH₃ | H | 2,4-diCl—C₆H₃—CH₂ | | H | H | 4-F | m.p. 133-137° C. |
| H | CH₃ | H | 2,4-diCl—C₆H₃—CH₂ | | H | H | 4-F | oil, δ 8.04 (s, 1H triazole C—H) |
| H | CH₂CH=CH₂ | H | 2,4-diCl—C₆H₃—CH₂ | | H | H | 4-F | oil, δ 7.94 (s, 1H triazole C—H) |

TABLE Vb-continued

| Q | R¹ | R² | R³ | | R⁵ | R⁶ | R⁷ | Properties |
|---|---|---|---|---|---|---|---|---|
| H | H | H | 2,4-diCl—C₆H₃—CH₂ | | H | 4-Cl | 2-Cl | m.p. 87–95° C. |
| H | CH₃ | H | 2,4-diCl—C₆H₃—CH₂ | | H | 4-Cl | 2-Cl | oil, δ 8.06 (s, 1H triazole C—H) |
| H | H | H | 2,4-diCl—C₆H₃—CH(CH₃)— | | H | H | 4-F | Isomer A: oil, δ 7.7 (s, 1H triazole C—H) Isomer B: oil, δ 7.7 (s, 1H triazole C—H) |
| H | H | H | 4-F—C₆H₄—CH(CH₃)— | | H | 4-Cl | 2-Cl | Isomer A: oil, δ 7.7 (s, 1H triazole C—H) Isomer B: oil, δ 7.7 (s, 1H triazole C—H) |
| H | CH₃ | H | 4-F—C₆H₄—CH(CH₃)— | | H | 4-Cl | 2-Cl | oil. δ 7.7 (s, 1H triazole C—H) |

Following the procedures described earlier and exemplified by Examples 5a, 5b, 5c, 5f, 5g and 5h, compounds in Table Vc can be prepared.

TABLE Vc

| Q | R¹ | R² | R⁵ | R⁶ | R⁷ | R⁸ | R⁹ | Properties |
|---|---|---|---|---|---|---|---|---|
| H | H | H | H | H | 4-C₆H₅ | H | 4-F | |
| H | H | H | H | H | 4-F | H | 4-CF₃ | |
| H | H | H | H | H | 4-F | H | 2-CF₃ | |
| H | H | H | H | H | 4-F | H | 3-CF₃ | |
| H | H | H | H | H | 2-F | 4-F | 2-F | |
| H | H | H | H | H | H | H | H | |
| H | H | H | H | H | 4-Cl | H | 4-Cl | |
| H | H | H | H | H | 2-(CHBr—CH₂Br) | H | 4-F | |
| H | H | H | H | H | 4-CH₃ | 4-Cl | 2-Cl | |
| H | H | H | H | H | 4-OCH₃ | 4-Cl | 2-Cl | |
| H | H | H | H | H | 2-F | H | 4-Cl | |
| H | H | H | H | H | 3-CF₃ | 4-Cl | 2-Cl | |
| H | H | H | H | H | 4-F | 5-F | 3-F | |
| H | H | H | H | H | 4-F | H | 3-F | |
| H | H | H | H | H | 4-Cl | 4-F | 2-F | |
| H | H | H | H | 3-Cl | 2-Cl | 4-Cl | 3-Cl | |
| H | H | H | H | H | 3-F | 4-Cl | 2-Cl | |
| H | H | H | H | H | 4-F | 5-F | 2-F | |
| H | H | H | H | H | 4-CN | H | 4-F | |
| H | H | H | H | H | 4-SCH₃ | H | 4-F | |
| H | H | H | 6-F | 4-F | 2-F | H | 4-Cl | |
| H | H | H | H | H | 4-SO₂CH₃ | H | 4-F | |
| H | H | H | H | H | 2-CF₃ | H | 4-Cl | |
| H | H | H | H | 4-Cl | 2-Cl | H | 4-F | m.p. 103–107° C. |
| H | H | H | H | H | 4-F | H | 4-Cl | |
| H | H | H | H | H | 4-F | H | 4-F | m.p. 130–134° C. |
| H | H | H | H | H | 2-F | H | 4-F | |
| H | H | H | H | H | 2-Cl | H | 4-F | |
| H | H | H | H | 3-Cl | 2-Cl | H | 4-F | |
| H | H | H | H | 4-F | 2-F | H | 4-F | |
| H | H | H | H | H | 4-CH₃ | H | 4-F | |

TABLE Vc-continued

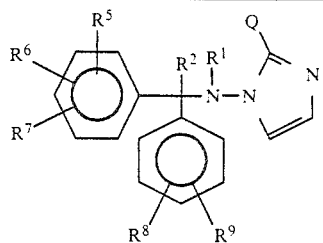

| Q | R¹ | R² | R⁵ | R⁶ | R⁷ | R⁸ | R⁹ | Properties |
|---|---|---|---|---|---|---|---|---|
| H | H | H | H | H | 4-OCH₃ | H | 4-F | |
| H | H | H | H | H | 4-NO₂ | H | 4-F | |
| H | H | H | H | 4-Cl | 2-CH₃ | H | 4-F | |
| H | H | H | H | 4-F | 2-CH₃ | H | 4-F | |
| H | H | H | H | 5-F | 3-F | H | 4-F | |
| H | H | H | H | 4-Cl | 2-Cl | H | 2-CH₃ | |
| H | H | H | H | 4-Cl | 2-Cl | H | 4-Cl | m.p. 116–117° C. |
| H | H | H | H | 4-Cl | 2-Cl | H | 3-Cl | |
| H | H | H | H | 4-Cl | 2-Cl | H | 2-Cl | |
| H | H | H | H | 4-F | 2-CH₃ | 4-Cl | 2-Cl | |
| H | H | H | H | 4-Cl | 2-CH₃ | 4-Cl | 2-Cl | |
| H | H | H | H | H | 4-C₆H₅ | 4-Cl | 2-Cl | |
| H | H | H | H | H | 4-(4-Cl—C₆H₄) | 4-Cl | 2-Cl | |
| H | H | H | H | H | 4-C₆H₅O | 4-Cl | 2-Cl | |
| H | CH₃ | H | H | H | 4-C₆H₅ | H | 4-F | |
| H | CH₃ | H | H | H | 4-F | H | 4-CF₃ | |
| H | CH₃ | H | H | H | 4-F | H | 2-CF₃ | |
| H | CH₃ | H | H | H | 4-F | H | 3-CF₃ | |
| H | CH₃ | H | H | H | 2-F | 4-F | 2-F | |
| H | CH₃ | H | H | H | H | H | H | |
| H | CH₃ | H | H | H | 4-Cl | H | 4-Cl | |
| H | CH₃ | H | H | H | 2-(CHBr—CH₂Br) | H | 4-F | |
| H | CH₃ | H | H | H | 4-CH₃ | 4-Cl | 2-Cl | |
| H | CH₃ | H | H | H | 4-OCH₃ | 4-Cl | 2-Cl | |
| H | CH₃ | H | H | H | 2-F | H | 4-Cl | |
| H | CH₃ | H | H | H | 3-CF₃ | 4-Cl | 2-Cl | |
| H | CH₃ | H | H | H | 4-F | 5-F | 3-F | |
| H | CH₃ | H | H | H | 4-F | H | 3-F | |
| H | CH₃ | H | H | H | 4-Cl | 4-F | 2-F | |
| H | CH₃ | H | H | 3-Cl | 2-Cl | 4-Cl | 3-Cl | |
| H | CH₃ | H | H | H | 3-F | 4-Cl | 2-Cl | |
| H | CH₃ | H | H | H | 4-F | 5-F | 2-F | |
| H | CH₃ | H | H | H | 4-CN | H | 4-F | |
| H | CH₃ | H | H | H | 4-SCH₃ | H | 4-F | |
| H | CH₃ | H | 6-F | 4-F | 2-F | H | 4-Cl | |
| H | CH₃ | H | H | H | 4-SO₂CH₃ | H | 4-F | |
| H | CH₃ | H | H | H | 2-CF₃ | H | 4-Cl | |
| H | CH₃ | H | H | 4-Cl | 2-Cl | H | 4-F | oil, δ 6.8 (s, 1H imidazole C—H) |
| H | CH₃ | H | H | H | 4-F | H | 4-Cl | |
| H | CH₃ | H | H | H | 4-F | H | 4-F | m.p. 126–132° C. |
| H | CH₃ | H | H | H | 2-F | H | 4-F | |
| H | CH₃ | H | H | H | 2-Cl | H | 4-F | |
| H | CH₃ | H | H | 3-Cl | 2-Cl | H | 4-F | |
| H | CH₃ | H | H | 4-F | 2-F | H | 4-F | |
| H | CH₃ | H | H | H | 4-CH₃ | H | 4-F | |
| H | CH₃ | H | H | H | 4-OCH₃ | H | 4-F | |
| H | CH₃ | H | H | H | 4-NO₂ | H | 4-F | |
| H | CH₃ | H | H | 4-Cl | 2-CH₃ | H | 4-F | |
| H | CH₃ | H | H | 4-F | 2-CH₃ | H | 4-F | |
| H | CH₃ | H | H | 5-F | 3-F | H | 4-F | |
| H | CH₃ | H | H | 4-Cl | 2-Cl | H | 2-CH₃ | |
| H | CH₃ | H | H | 4-Cl | 2-Cl | H | 4-Cl | m.p. 45–48° C. |
| H | CH₃ | H | H | 4-Cl | 2-Cl | H | 3-Cl | |
| H | CH₃ | H | H | 4-Cl | 2-Cl | H | 2-Cl | |
| H | CH₃ | H | H | 4-F | 2-CH₃ | 4-Cl | 2-Cl | |
| H | CH₃ | H | H | 4-Cl | 2-CH₃ | 4-Cl | 2-Cl | |
| H | CH₃ | H | H | H | 4-C₆H₅ | 4-Cl | 2-Cl | |
| H | CH₃ | H | H | H | 4-(4-Cl—C₆H₄) | 4-Cl | 2-Cl | |
| H | CH₃ | H | H | H | 4-C₆H₅O | 4-Cl | 2-Cl | |
| H | (CH₂)₅CH₃ | H | H | 4-Cl | 2-Cl | H | 4-F | |
| H | CH₂CH=CH₂ | H | H | H | 4-F | H | 4-F | |
| H | CH₂—C₆H₅ | H | H | H | 4-F | H | 4-F | |
| H | CH₂—CH=CH₂ | H | H | H | 4-F | H | 2-F | |
| H | CH₂F | H | H | H | 4-F | H | 4-F | |
| H | CF₂H | H | H | H | 4-F | H | 4-F | |
| H | C(O)CH₃ | H | H | H | 4-F | H | 4-F | |
| H | C(O)CH₃ | H | H | 4-Cl | 2-Cl | 4-Cl | 2-Cl | |
| H | CH₂CO₂C₂H₅ | H | H | H | 4-F | H | 4-F | |

TABLE Vc-continued

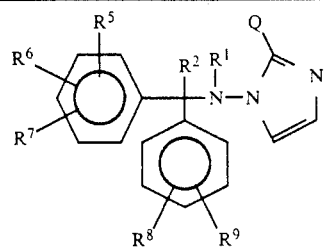

| Q | $R^1$ | $R^2$ | $R^5$ | $R^6$ | $R^7$ | $R^8$ | $R^9$ | Properties |
|---|---|---|---|---|---|---|---|---|
| H | $CH_2CO_2CH_2C_6H_5$ | H | H | H | 4-F | H | 4-F | |
| H | $C(O)OCH_3$ | H | H | H | 4-F | H | 4-F | |
| H | $C(O)OCH_3$ | H | H | H | 4-C | H | 4-Cl | |
| H | $CH_2SCH_3$ | H | H | H | 4-F | H | 4-F | |
| H | $CH_2OCH_3$ | H | H | H | 4-F | H | 4-F | |
| H | $CH_2OCH_3$ | H | H | 4-Cl | 2-Cl | H | 4-F | |
| H | $CH_2C\equiv CH$ | H | H | 4-Cl | 2-Cl | H | 4-F | |
| H | cyclopropyl | H | H | 4-Cl | 2-Cl | H | 4-F | |
| H | $CH_2$-cyclopropyl | H | H | 4-Cl | 2-Cl | H | 4-F | |
| H | $C_2H_5$ | H | H | H | 4-F | H | 4-F | |
| H | $(CH_2)_3CH_3$ | H | H | H | 4-F | H | 4-F | |
| H | $CH_2CO_2H$ | H | H | H | 4-F | H | 4-F | |
| H | $CH_2CH=CHCl$ | H | H | 4-Cl | 2-Cl | H | 4-F | |
| H | $CH_2CH=CH_2$ | H | H | 4-Cl | 2-Cl | H | 4-F | m.p. 41–44° C. |
| H | $CH_2CH_3$ | H | H | 4-Cl | 2-Cl | H | 4-F | m.p. 43–47° C. |
| H | $C(O)NHCH_3$ | H | H | 4-Cl | 2-Cl | H | 4-F | |
| H | $C(O)OC(CH_3)_3$ | H | H | 4-Cl | 2-Cl | H | 4-F | |
| H | $CH_2CH(CH_3)_2$ | H | H | 4-Cl | 2-Cl | H | 4-F | |
| H | $C(O)(CH_2)_3CH_3$ | H | H | 4-Cl | 2-Cl | H | 4-F | |
| H | $CH_2CH(CH_3)_2$ | H | H | 4-Cl | 2-Cl | H | 4-F | |
| H | $C(O)(CH_2)_3CH_3$ | H | H | 4-Cl | 2-Cl | H | 4-F | |
| SH | $CH_3$ | H | H | 4-Cl | 2-Cl | H | 4-F | |
| $SCH_2SCN$ | $CH_3$ | H | H | 4-Cl | 2-Cl | H | 4-F | |
| $S(O)CH_2SCN$ | $CH_3$ | H | H | 4-Cl | 2-Cl | H | 4-F | |
| $S(O)_2CH_2SCN$ | $CH_3$ | H | H | 4-Cl | 2-Cl | H | 4-F | |
| $SCH_3$ | $CH_3$ | H | H | 4-Cl | 2-Cl | H | 4-F | |
| $SCH_2CN$ | $CH_3$ | H | H | 4-Cl | 2-Cl | H | 4-F | |
| $S(O)CH_2CN$ | $CH_3$ | H | H | 4-Cl | 2-Cl | H | 4-F | |
| $SO_2CH_2CN$ | $CH_3$ | H | H | 4-Cl | 2-Cl | H | 4-F | |
| I | $CH_3$ | H | H | 4-Cl | 2-Cl | H | 4-F | |
| Br | $CH_3$ | H | H | 4-Cl | 2-Cl | H | 4-F | |
| F | $CH_3$ | H | H | 4-Cl | 2-Cl | H | 4-F | |
| CHO | $CH_3$ | H | H | 4-Cl | 2-Cl | H | 4-F | |
| SH | H | H | H | H | 4-F | H | 4-F | |
| $SCH_2SCN$ | H | H | H | H | 4-Cl | H | 4-Cl | |
| $SO_2CH_2SCN$ | H | H | H | 4-Cl | 2-Cl | H | 4-Cl | |
| $SCH_3$ | H | H | H | H | 4-F | H | 2-F | |
| $SCH_2CN$ | $CH_3$ | H | H | H | 4-Cl | H | 2-Cl | |
| $SO_2CH_2CN$ | $CH_3$ | H | H | H | 4-Cl | H | 2-Cl | |
| I | $CH_3$ | H | H | H | 4-F | H | 4-F | |
| Br | $CH_3$ | H | H | H | 4-F | H | 4-F | |
| Cl | $CH_3$ | H | H | H | 4-F | H | 4-F | |
| H | H | $CF_3$ | H | H | 4-F | H | H | |
| H | $CH_3$ | $CF_3$ | H | H | 4-F | H | H | |
| H | H | $CF_3$ | H | 4-Cl | 2-Cl | H | H | |
| H | $CH_3$ | $CF_3$ | H | 4-Cl | 2-Cl | H | H | |
| H | H | $CH_2CN$ | H | H | 4-F | H | 4-F | |
| H | $CH_3$ | $CH_2CN$ | H | H | 4-F | H | 4-F | |
| H | H | $(CH_2)_3CH_3$ | H | H | 4-F | H | 4-F | |
| H | $CH_3$ | $(CH_2)_3CH_3$ | H | H | 4-F | H | 4-F | |
| H | H | cyclopropyl | H | H | 4-Cl | H | 4-Cl | |
| H | $CH_3$ | cyclopropyl | H | H | 4-Cl | H | 4-Cl | |
| H | H | CHO | H | 4-Cl | 2-Cl | H | 4-F | |
| H | $CH_3$ | CHO | H | 4-Cl | 2-Cl | H | 4-F | |
| H | H | $CH_2OH$ | H | 4-Cl | 2-Cl | H | 4-F | |
| H | $CH_3$ | $CH_2OH$ | H | 4-Cl | 2-Cl | H | 4-F | |
| H | H | $CH_2F$ | H | H | 4-F | H | 4-F | |
| H | $CH_3$ | $CH_2F$ | H | H | 4-F | H | 4-F | |
| H | H | CN | H | 4-Cl | 2-Cl | H | 4-F | |
| H | $CH_3$ | CN | H | 4-Cl | 2-Cl | H | 4-F | |
| H | H | CN | H | 4-Cl | 2-Cl | H | 4-Cl | |
| H | $CH_3$ | CN | H | 4-Cl | 2-Cl | H | 4-Cl | |
| H | H | $CH=CH_2$ | H | H | 4-Cl | H | 4-Cl | |
| H | $CH_3$ | $CH=CH_2$ | H | H | 4-Cl | H | 4-Cl | |
| H | H | $C\equiv CH$ | H | H | 4-Cl | H | 4-Cl | |
| H | $CH_3$ | $C\equiv CH$ | H | H | 4-Cl | H | 4-Cl | |
| H | H | $C\equiv CCH_3$ | H | H | 4-Cl | H | 4-Cl | |
| H | $CH_3$ | $C\equiv CCH_3$ | H | H | 4-Cl | H | 4-Cl | |
| H | H | $CH_2CH=CHCH_3$ | H | H | 4-Cl | H | 4-Cl | |

TABLE Vc-continued

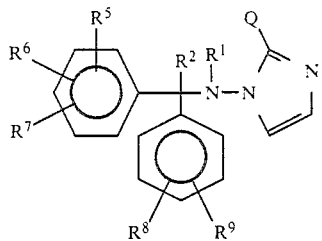

| Q | R¹ | R² | R⁵ | R⁶ | R⁷ | R⁸ | R⁹ | Properties |
|---|---|---|---|---|---|---|---|---|
| H | CH₃ | CH₂CH=CHCH₃ | H | H | 4-Cl | H | 4-Cl | |
| H | H | H | 6-Cl | 4-Cl | 2-Cl | H | 4-F | |
| H | CH₃ | H | 6-Cl | 4-Cl | 2-Cl | H | 4-F | |
| H | H | H | 6-Cl | 4-Cl | 2-Cl | 4-Cl | 2-Cl | |
| H | CH₃ | H | 6-Cl | 4-Cl | 2-Cl | 4-Cl | 2-Cl | |
| H | H | H | H | 4-Cl | 2-CN | H | 4-Cl | |
| H | CH₃ | H | H | 4-Cl | 2-CN | H | 4-Cl | |

Following the procedures described earlier and exemplified by Examples 5a, 5b, 5c, 5d, 5e, 5f, 5g, 5h, 5i, 5j, 5k and 5l, compounds in Table Vb can be prepared.

TABLE Vd

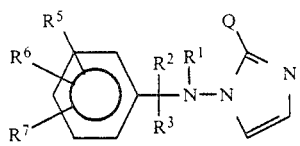

| Q | R¹ | R² | R³ | R⁵ | R⁶ | R⁷ | Properties |
|---|---|---|---|---|---|---|---|
| H | CH₃ | H | 3-thienyl | H | H | 4-F | |
| H | H | H | 3-thienyl | H | 4-Cl | 2-Cl | |
| H | H | H | 2-thienyl | H | 4-Cl | 2-Cl | |
| H | CH₃ | H | 3-thienyl | H | 4-Cl | 2-Cl | |
| H | CH₃ | H | 2-thienyl | H | 4-Cl | 2-Cl | |
| H | H | H | 4-pyridyl | H | H | H | |
| H | CH₃ | H | 4-pyridyl | H | H | H | |
| H | H | H | 3-pyridyl | H | H | H | |
| H | CH₃ | H | 3-pyridyl | H | H | H | |
| H | H | H | 3-pyridyl | H | 4-Cl | 2-Cl | |
| H | CH₃ | H | 3-pyridyl | H | 4-Cl | 2-Cl | |
| H | H | H | 2-pyridyl | H | 4-Cl | 2-Cl | |
| H | CH₃ | H | 2-pyridyl | H | 4-Cl | 2-Cl | |
| H | CH₃ | H | 3-(2,5-diCl-thienyl) | H | H | 4-Cl | |
| H | CH₃ | H | 3-(2,5-diCl-thienyl) | H | H | 4-Cl | |
| H | H | CN | (CH₂)₃CH₃ | H | H | 4-Cl | |
| H | H | CN | (CH₂)₃CH₃ | H | 4-Cl | 2-Cl | |
| H | H | CN | (CH₂)₃CH₃ | H | H | 4-C₆H₅ | |
| H | CH₃ | CN | (CH₂)₃CH₃ | H | H | 4-Cl | |
| H | CH₃ | CN | (CH₂)₃CH₃ | H | 4-Cl | 2-Cl | |
| H | CH₃ | CN | (CH₂)₃CH₃ | H | H | 4-C₆H₅ | |
| H | H | CF₃ | (CH₂)₃CH₃ | H | H | H | |
| H | CH₃ | CF₃ | (CH₂)₃CH₃ | H | H | H | |
| H | H | H | CF₂CF₃ | H | H | 4-F | |
| H | CH₃ | H | CF₂CF₃ | H | H | 4-F | |
| H | H | H | cyclohexyl | H | H | 4-Cl | |
| H | CH₃ | H | cyclohexyl | H | H | 4-Cl | |
| H | H | H | CH(CH₃)cyclopropyl | H | 4-Cl | 2-Cl | |
| H | CH₃ | CN | CH(CH₃)cyclopropyl | H | 4-Cl | 2-Cl | |
| H | H | H | CH₂-cyclopentyl | H | 4-Cl | 2-Cl | |
| H | CH₃ | H | CH₂-cyclopentyl | H | 4-Cl | 2-Cl | |
| H | H | H | CH₂-cyclohexyl | H | 4-Cl | 2-Cl | |
| H | CH₃ | H | CH₂-cyclohexyl | H | 4-Cl | 2-Cl | |
| H | CH₃ | H | 1-(4-F—C₆H₄)-vinyl | H | H | 4-F | |
| H | CH₂CH=CH₂ | H | 1-(4-F—C₆H₄)-vinyl | H | H | 4-F | |
| H | H | H | 4-F—C₆H₄—CH₂ | H | H | 4-F | |
| H | CH₃ | H | 4-F—C₆H₄—CH₂ | H | H | 4-F | |
| H | CH₂CH=CH₂ | H | 4-F—C₆H₄—CH(CH₃) | H | H | 4-F | |
| H | H | H | 1-(4-F—C₆H₄)-vinyl | H | H | 4-F | |
| H | H | H | 4-F—C₆H₄—CH(CH₃) | H | H | 4-F | |
| H | CH₃ | H | 4-F—C₆H₄—CH(CH₃) | H | H | 4-F | |
| H | H | H | 1-(4-Cl—C₆H₄)-vinyl | H | H | 4-Cl | |
| H | H | H | 4-F—C₆H₄—CH(CH₃) | H | 4-Cl | 2-Cl | |

TABLE Vd-continued

| Q | R¹ | R² | R³ | R⁵ | R⁶ | R⁷ | Properties |
|---|---|---|---|---|---|---|---|
| H | CH₃ | H | 4-F—C₆H₄—CH(CH₃) | H | 4-Cl | 2-Cl | |
| H | H | CF₃ | C₆H₅—CH₂ | H | 4-Cl | 2-Cl | |
| H | CH₃ | CF₃ | C₆H₅—CH₂ | H | 4-Cl | 2-Cl | |
| H | H | H | 2,4-diCl-C₆H₃—CH(CH₃) | H | H | 4-F | |
| H | CH₃ | H | 2,4-diCl-C₆H₃—CH(CH₃) | H | H | 4-F | |
| H | CH₃ | H | 1-(4-Cl—C₆H₄)-vinyl | H | H | 4-Cl | |
| H | CH₃ | CH₃ | 1-(4-F—C₆H₄)-vinyl | H | H | 4-F | |
| H | H | CH₃ | 1-(2,4-diCl-C₆H₃)-vinyl | H | H | 4-F | |
| H | CH₃ | H | 1-(2,4-diCl-C₆H₃)-vinyl | H | H | 4-F | |
| H | H | CH₃ | 1-(4-F—C₆H₄)-vinyl | H | 4-Cl | 2-Cl | |
| H | CH₃ | H | 1-(4-F—C₆H₄)-vinyl | H | 4-Cl | 2-Cl | |
| H | CH₃ | H | 1-(4-F—C₆H₄)-vinyl | H | H | 4-F | |
| H | H | H | 4-F—C₆H₄—CH₂ | H | 4-Cl | 2-Cl | |
| H | CH₃ | H | 4-F—C₆H₄—CH₂ | H | 4-Cl | 2-Cl | |
| H | H | H | 2-(2,4-diCl-C₆H₃)-vinyl | H | H | 4-F | |
| H | CH₃ | H | 2-(2,4-diCl-C₆H₃)-vinyl | H | H | 4-F | |
| H | H | H | 4-F—C₆H₄—CF₂ | H | H | 4-Cl | |
| H | CH₃ | H | 4-F—C₆H₄—CF₂ | H | H | 4-Cl | |
| H | H | H | 4-F—C₆H₄—CH(CN) | H | H | 4-Cl | |
| H | CH₃ | H | 4-F—C₆H₄—CH(CN) | H | H | 4-Cl | |
| H | H | H | 4-F—C₆H₄—CF(CN) | H | H | 4-Cl | |
| H | CH₃ | H | 4-F—C₆H₆—CF(CN) | H | H | 4-Cl | |
| H | H | H | 4-F—C₆H₄—CH(n-propyl) | H | H | 4-Cl | |
| H | CH₃ | H | 4-F—C₆H₄—CH(N-propyl) | H | H | 4-Cl | |
| H | H | H | 4-F—C₆H₄—CH₂ | H | 4-Cl | 2-Cl | oil, δ 6.85 (s, 1H triazole C—H) |
| H | CH₃ | H | 4-F—C₆H₄—CH₂ | H | 4-Cl | 2-Cl | |
| H | H | H | 3,5-diCl-2-pyridyl | H | H | 4-F | oil, δ 6.75 (s, 1H triazole C—H) |
| H | CH₃ | H | 3,5-diCl-2-pyridyl | H | H | 4-F | |
| H | CH₃ | H | 2,6-diF-3-pyridyl | H | H | 4-Cl | |
| H | H | H | 2,6-diF-3-pyridyl | H | H | 4-Cl | |
| H | H | H | 4-Cl—C₆H₄—CH(SCH₃)— | H | 4-Cl | 1-Cl | |
| H | H | H | 4-Cl—C₆H₄—CH(OCH₃)— | H | 4-Cl | 2-Cl | |
| H | H | H | 4-Cl—C₆H₄—(CH₂)₂ | H | 4-Cl | 2-Cl | |
| H | H | H | 4-Cl—C₆H₄—O—CH₂— | H | 4-F | 2-F | |
| H | CH₃ | H | 4-Cl—C₆H₄—O—CH₂— | H | 4-F | 2-F | |
| H | H | H | 4-Cl—C₆H₄—S—CH₂— | H | 4-F | 2-F | |
| H | CH₃ | H | 4-Cl—C₆H₄—S—CH₂— | H | 4-F | 2-F | |

Following the procedures described earlier and exemplified by Examples 5b, 5c, 5d, 5e, 5f, 5g, 5h, 5i, 5j, 5k and 5l, compounds in Table Ve can be prepared.

TABLE Ve

| Ar | R¹ | R² | R³ | Z | Q | Properties |
|---|---|---|---|---|---|---|
| 3,5-di-Cl-2-pyridyl | H | H | 5-Cl-1-thienyl | N | H | m.p. 84–85° C. |
| 2,6-diF-3-pyridyl | H | H | 5-Cl-2-pyridyl | N | H | |
| 2,6-diF-3-pyridyl | CH₃ | H | 5-Cl-2-pyridyl | N | H | |
| 2,6-diF-3-pyridyl | H | H | 1-(4-F—C₆H₄)-vinyl | N | H | m.p. 130–132° C. |
| 2,6-diF-3-pyridyl | CH₃ | H | 1-(4-F—C₆H₄)-vinyl | N | H | |
| 2,6-diF-3-pyridyl | H | H | 4-F—C₆H₄—CH(CH₃)— | N | H | Isomer A: m.p. 135–137° C. Isomer B: m.p. 97–101° C. |
| 2,6-diF-3-pyridyl | CH₃ | H | 4-F—C₆H₄—CH(CH₃)— | N | H | oil, δ 7.92 and 8.1 (2s, 1H (triazole C—H) |
| 3,5-diCl-2-pyridyl | H | H | 2-(4-F—C₆H₄)-vinyl | N | H | oil, δ 8.0 (s, 1H triazole C—H) |

TABLE Ve-continued

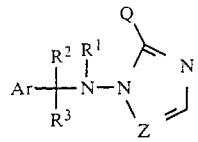

| Ar | R¹ | R² | R³ | Z | Q | Properties |
|---|---|---|---|---|---|---|
| 3,5-diCl-2-pyridyl | CH₃ | H | 1-(4-F—C₆H₄)-vinyl | N | H | |
| 3,5-diCl-2-pyridyl | H | H | 4-F—C₆H₄—CH(CH₃)— | N | H | |
| 3,5-diCl-2-pyridyl | CH₃ | H | 4-F—C₆H₄—CH(CH₃)— | N | H | |
| 3,5-diCl-2-pyridyl | H | H | 4-F—C₆H₄—CH(CH₃)— | CH | H | |
| 3,5-diCl-2-pyridyl | CH₃ | H | 4-F—C₆H₄—CH(CH₃)— | CH | H | |
| 3,5-diCl-2-pyridyl | H | H | 5-Cl-2-pyridyl | N | H | oil, δ 8.0 (s, 1H triazole C—H) |
| 3,5-diCl-2-pyridyl | CH₃ | H | 5-Cl-2-pyridyl | N | H | |
| 2,6-diCl-3-pyridyl | H | H | 2-(4-Cl—C₆H₄)-vinyl | N | H | |
| 2,6-diCl-3-pyridyl | CH₃ | H | 2-(4-Cl—C₆H₄)-vinyl | N | SH | |
| 3,5-diCl-2-pyridyl | H | H | 4-Cl—C₆H₄—O—CH₂— | N | H | |
| 3,5-diCl-2-pyridyl | CH₃ | H | 4-Cl—C₆H₄—O—CH₂ | N | H | |

UTILITY

The compounds of this invention are useful as plant disease control agents. They are effective in controlling a broad spectrum of plant diseases, particularly foliar pathogens of ornamental, vegetable, field, cereal and fruit crops, such as, *Puccinia recondita, Sphaerotheca fuliginea, Erysiphe graminis, Podosphaera leucotricha, Venturia inaequalis, Pyricularia oryzae, Bipolaris oryzae, Pseudocercosporella hepotricoides, Cercospora arachidicola, Cerospora beticola* and *Monilinia fructicola*. They also control soil borne pathogens such as *Rhizoctonia solani*.

In addition to the foregoing, certain compounds of this invention are useful for treating fungal infections in mammals. Pharmaceutical antifungal compositions of these compounds and their method-of-use for treating a fungal infection in a mammal are within the preview of the present invention.

FORMULATION

The compounds of this invention will generally be used in formulation with a liquid or solid diluent or with an organic solvent. Useful formulations of the compounds of Formula I can be prepared in conventional ways. They include dusts, granules, pellets, solutions, emulsions, wettable powders, emulsifiable concentrates and the like. Many of these may be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of a) about 0.1% to 35% surfactant(s) and b) about 5% to 99% solid or liquid inert diluent(s). More specifically, they will contain these ingredients in the following approximate proportions:

| | Active Ingredient | Percent by Weight Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 5-50 | 40-95 | 0-35 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell N.J. The more absorptive diluents are preferred for the wettable powders and the denser ones for dusts. Typical liquid diluents and solvents are described in Marsden, "Solvents Guide, " 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

H. M. Loux, U.S. Pat No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, LIne 43 through Col. 7, Line 62 and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, Line 66 through Col. 5, Line 17 and Examples 1–4.

G. C. Klingman, "Weed Control as a Science", John Wiley and Sons, Inc., New York, 1961, pp. 81–96.

J. D. Fryer and S. A. Evans, "Weed Control Handbook", 5th Edn. Blackwell Scientific Publications, Oxford, 1968, pp. 101–103.

Examples of useful formulations of compounds of the present invention are as follows.

EXAMPLE 6

| Wettable Powder | |
|---|---|
| N-[(2,4-dichlorophenyl)(4-fluorophenyl)methyl]-N-methyl-1H-1,2,4-triazol-1-amine | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled, reblended and packaged.

EXAMPLE 7

| Wettable Powder | |
|---|---|
| N-[(2,4-dichlorophenyl)(4-fluorophenyl)methyl]-N-methyl-1H-imidazol-1-amine | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled, reblended and packaged.

EXAMPLE 8

| Wettable Powder | |
|---|---|
| N-[(2,4-dichlorophenyl)(4-fluorophenyl)methylene]-1H-1,2,4-triazole-1-amine | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled, reblended and packaged.

EXAMPLE 9

| High Strength Concentrate | |
|---|---|
| N-[(2,4-dichlorophenyl)(4-fluorophenyl)methyl]-1H-1,2,4-triazol-1-amine | 98.5% |
| silica aerogel | 0.5% |
| synthetic amorphous fine silica | 1.0% |

The ingredients are blended and ground in a hammermill to produce a high strength concentrate essentially all passing a U.S.S. No. 50 sieve (0.3 mm openings). This material may then be formulated in a variety of ways.

EXAMPLE 10

| Aqueous Suspension | |
|---|---|
| N-[bis-(4-fluorophenyl)methyl]-N-methyl-1H-1,2,4-triazol-1-amine | 25% |
| hydrated attapulgite | 3% |
| crude calcium ligninsulfonate | 10% |
| sodium dihydrogen phosphate | 0.5% |
| water | 61.5% |

The ingredients are ground together in a ball, sand, or roller mill until the solid particles have been reduced to diameters under 10 microns.

EXAMPLE 11

| Solution | |
|---|---|
| N-[bis-(4-fluorophenyl)methyl]-1H-1,2,4-triazol-1-amine | 30% |
| dimethylformamide | 70% |

The ingredients are combined and stirred to produce a solution, which can be used for low volume applications.

EXAMPLE 12

| Emulsifiable Concentrate | |
|---|---|
| N-[(2,4-dichlorophenyl)(4-fluorophenyl)methyl]-N-methyl-1H-1,2,4-triazol-1-amine | 15% |
| blend of calcium sulfonates and nonionic surfactants | 25% |
| xylene | 60% |

The ingredients are combined and stirred until the active is dissolved. A fine screen filter is included in packaging operation to insure the absence of any extraneous undissolved material in the product.

EXAMPLE 13

| Granule | |
|---|---|
| wettable powder of Example 6 | 15% |
| gypsum | 69% |
| potassium sulfate | 16% |

The ingredients are blended in a rotating or fluid bed mixer and water sprayed on to accomplish granulation. When most of the material has reached the desired range of 1.0 to 0.42 mm. (U.S.S. No. 18 to 40 sieves), the granules are removed, dried, and screened. Oversize material is crushed to produce additional material in the desired range.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 45 parts by weight. Suitable agents of this type are well-known to those skilled in the art. Some are listed below:

FUNGICIDES

Methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (cymoxanil)
N-trichloromethylthiotetrahydrophthalimide (captan)
N-trichloromethylthiophthalimide (folpet)
dimethyl(4,4'-o-phenylene)bis(3-thioallophanate) (thiophanate-methyl)
2-thiazol-4-yl)benzimidazole (thiabendazole)
aluminum tris(O-ethylene phosphonate) ("Aliette")
tetrachloroisophthalonitrile (chlorothalonil)
2,6-dichloro-4-nitroaniline (dichloran)
N-(2,6-dimethylphenyl)-N-methoxyacetyl)alanine methyl ester (metalaxyl)
cis-N-[(1,1,2,2-tetrachloroethyl)thio]-4-cyclohexene-1,2-dicarbioximide (captafol)
3-(3,5-dichlorophenyl)-N-(1-methyl-ethyl)-2,4-dioxo-1-imidazolidine carboxamide (iprodione)
3-(3,5-dichlorophenyl)-5-ethenyl-5-methyl-2,4-oxazolidinedione (vinclozolin)
2,6-4-tridecylmorpholine (tridemorph) kasugamycin
O-ethyl S,S-diphenyl phosphorodithioate (edofenphos)
1-[bis(4-fluorophenyl)(methyl)(silylmethyl)]-1H-1,2,4-triazole

APPLICATION

Disease control is ordinarily accomplished by applying an effective amount of the compound, normally as part of a formulation containing it, either pre- or post-infection to the portion of the plant to be protected, such as the roots, stems, foliage, fruit, seeds, tubers or bulbs, or to the medium (soil or sand) in which the plants to be protected are growing. The compound may also be applied to the seed from which the plants to be protected are to be grown.

Rates of application for these compounds can be influenced by many factors of the environment and should be determined under actual use conditions. Nevertheless, foliage can normally be protected when treated at a rate of from 1 gram or less up to 5000 grams of active ingredient per hectare. Plant growing in soil that is treated at a concentration from about 0.1 to about 20 kg of active ingredient per hectare can be protected from disease. Seed and seedlings can normally be protected when seed is treated at a rate of from about 0.06 to about 3 grams of active ingredient per kilogram of seed.

In the following Examples 14–26, the percent disease control is determined as the percent inhibition of disease symptom development on treated plants as compared to the average disease symptom development among untreated plants. In these examples, which further illustrate the present invention, the test compounds are as listed in Table A and B.

TABLE A

| CMPD | $R^1$ | $R^2$ | $R^3$ | AR | Q | Z |
|---|---|---|---|---|---|---|
| 1 | $CH_3$ | H | 4-F-Ph | 2,4-DiCl-Ph | H | N |
| 2 | $CH_2CO_2H$ | H | 4-F-Ph | 4-F-Ph | H | N |
| 3 | H | H | 4-F-Ph | 4-F-Ph | H | N |
| 4 | $CH_3$ | H | 4-F-Ph | 4-F-Ph | H | N |
| 5 | $CH_2CO_2ET$ | H | 4-F-Ph | 4-F-Ph | H | N |
| 6 | $CH_2SCH_3$ | H | 4-F-Ph | 4-F-Ph | H | N |
| 7 | $CH_2CH=CH_2$ | H | 4-F-Ph | 4-F-Ph | H | N |
| 8 | $CH_2CH_3$ | H | 4-F-Ph | 4-F-Ph | H | N |
| 9 | $CH_2CO_2CH_2Ph$ | H | 4-F-Ph | 4-F-Ph | H | N |
| 10 | $CH_2Ph$ | H | 4-F-Ph | 4-F-Ph | H | N |
| 11 | H | H | 4-F-Ph | 2-F-Ph | H | N |
| 12 | H | H | 4-F-Ph | 2,4-DiCl-Ph | H | N |
| 13 | H | H | 4-F-Ph | 2-$CF_3$-Ph | H | N |
| 14 | H | H | 2,4-DiF-Ph | 4-Cl-Ph | H | N |
| 15 | H | H | 4-Cl-Ph | 4-Cl-Ph | H | N |
| 16 | H | H | 2-$CF_3$-Ph | 4-Cl-Ph | H | N |
| 17 | H | H | 2,4-DiF-Ph | 2-F-Ph | H | N |
| 18 | H | H | 4-F-Ph | 4-Cl-Ph | H | N |
| 19 | H | H | 4-Cl-Ph | 2,4-DiCl-Ph | H | N |
| 20 | H | H | 2-$CF_3$-Ph | 2,4-DiCl-Ph | H | N |
| 21 | H | H | 2-F-Ph | 2,4-DiCl-Ph | H | N |
| 22 | $CH_3$ | H | 4-F-Ph | 2-$CF_3$-Ph | H | N |
| 23 | $CH_3$ | H | 2,4-DiF-Ph | 4-Cl-Ph | H | N |
| 24 | $CH_3$ | H | 2-$CF_3$-Ph | 4-Cl-Ph | H | N |
| 25 | $CH_3$ | H | 2,4-DiF-Ph | 2-F-Ph | H | N |
| 26 | $CH_3$ | H | 2-F-Ph | 4-Cl-Ph | H | N |
| 27 | $CH_3$ | H | 4-Cl-Ph | 2,4-DiCl-Ph | H | N |
| 28 | $CH_3$ | H | 2-F-Ph | 2,4-DiCl-Ph | H | N |
| 29 | $CH_3$ | H | 4-Cl-Ph | 4-Cl-Ph | H | N |
| 30 | $CH_3$ | H | 4-F-Ph | 4-$CF_3$-Ph | H | N |
| 31 | $CH_3$ | H | 4-F-Ph | 4-Ph-Ph | H | N |
| 32 | H | $CH_3$ | 4-F-Ph | 4-F-Ph | H | N |
| 33 | $CH_3$ | $CH_3$ | 4-F-Ph | 4-F-Ph | H | N |
| 34 | H | n-Bu | 4-F-Ph | 4-F-Ph | H | N |
| 35 | $CH_3$ | n-Bu | 4-F-Ph | 4-F-Ph | H | N |
| 36 | $CH_3$ | H | $CH_3$ | 4-F-Ph | H | N |
| 37 | $CH_2Ph$ | H | $CH_3$ | 4-F-Ph | H | N |
| 38 | $CH_3$ | H | C(=$CH_2$)-4-F-Ph | 4-F-Ph | H | N |
| 39 | $CH_2CH=CH_2$ | H | C(=$CH_2$)-4-F-Ph | 4-F-Ph | H | N |
| 40 | H | H | C(=$CH_2$)-4-F-Ph | 4-F-Ph | H | N |
| 41 | $CH_3$ | H | 3-thienyl | 4-F-Ph | H | N |
| 42 | H | $CF_3$ | Ph | 4-F-Ph | H | N |

TABLE A-continued

| CMPD | R¹ | R² | R³ | AR | Q | Z |
|---|---|---|---|---|---|---|
| 43 | H | CF₃ | Ph | 2,4-DiCl-Ph | H | N |
| 44 | H | CF₃ | CH₂(2,4-DiCl-Ph) | Ph | H | N |
| 45 | CH₃ | CF₃ | Ph | 4-F-Ph | H | N |
| 46 | CH₃ | CF₃ | Ph | 2,4-DiCl-Ph | H | N |
| 47 | CH₃ | CF₃ | CH₂(2,4-DiCl-Ph) | Ph | H | N |
| 48 | CH₃ | H | 4-F-Ph | 2-F-Ph | H | N |
| 49 | CH₂CH=CH₂ | H | 4-F-Ph | 2-F-Ph | H | N |
| 50 | CH₃ | H | 4-F-Ph | 4-Ph-Ph | CH₃ | N |
| 51 | CH₃ | H | 4-F-Ph | 4-CF₃-Ph | CH₃ | N |
| 52 | H(*HCl) | H | 4-F-Ph | 4-F-Ph | H | N |
| 53 | H | H | 4-F-Ph | 2,4-DiCl-Ph | SCH₃ | N |
| 54 | CH₂CH=CH₂ | H | 4-F-Ph | 2,4-DiCl-Ph | H | N |
| 55 | H | H | 2-(CHBr—CH₂Br)Ph | 4-F-Ph | H | N |
| 56 | H | H | 4-CH₃-Ph | 4-F-Ph | H | N |
| 57 | CH₃ | H | 4-CH₃-Ph | 4-F-Ph | H | N |
| 58 | H | H | 4-CH₃-Ph | 2,4-DiCl-Ph | H | N |
| 59 | CH₃ | H | 4-CH₃-Ph | 2,4-DiCl-Ph | H | N |
| 60 | H | H | 4-CH₃O-Ph | 4-F-Ph | H | N |
| 61 | CH₃ | H | 4-CH₃O-Ph | 4-F-Ph | H | N |
| 62 | H | H | 4-CH₃O-Ph | 2,4-DiCl-Ph | H | N |
| 63 | CH₃ | H | 4-CH₃O-Ph | 2,4-DiCl-Ph | H | N |
| 64 | H | H | 3-CF₃-Ph | 4-F-Ph | H | N |
| 65 | H | H | 4-CF₃-Ph | 2,4-DiCl-Ph | H | N |
| 66 | CH₃ | H | 3-CF₃-Ph | 2,4-DiCl-Ph | H | N |
| 67 | H | H | 2-CH₃O-Ph | 4-F-Ph | H | N |
| 68 | H | H | 3,5-DiF-Ph | 4-F-Ph | H | N |
| 69 | CH₃ | H | 2,4-DiF-Ph | 4-F-Ph | H | N |
| 70 | H | H | 3-F-Ph | 4-F-Ph | H | N |
| 71 | CH₃ | H | 3-F-Ph | 4-F-Ph | H | N |
| 72 | H | H | 2,3-DiCl-Ph | 2,4-DiCl-Ph | H | N |
| 73 | H | H | 2,3-DiCl-Ph | 4-F-Ph | H | N |
| 74 | CH₃ | H | 2,3-DiCl-Ph | 4-F-Ph | H | N |
| 75 | H | H | 3-F-Ph | 2,4-DiCl-Ph | H | N |
| 76 | CH | H | 2,5-DiF-Ph | 4-F-Ph | H | N |
| 77 | H | H | 4-F-benzyl | 4-F-Ph | H | N |
| 78 | CH₃ | H | 4-F-benzyl | 4-F-Ph | H | N |
| 79 | H | H | 2-CH₃-4-Cl-Ph | 4-F-Ph | H | N |
| 80 | CH₃ | H | 2-CH₃-4-Cl-Ph | 4-F-Ph | H | N |
| 81 | H | H | 2-CH₃-4-Cl-Ph | 2,4-DiCl-Ph | H | N |
| 82 | CH₃ | H | 2-CH₃-4-Cl-Ph | 2,4-DiCl-Ph | H | N |
| 83 | H | H | 2-CH₃-4-F-Ph | 2,4-DiCl-Ph | H | N |
| 84 | CH₃ | H | 2-CH₃-4-F-Ph | 2,4-DiCl-Ph | H | N |
| 85 | H | CH₂CN | 4-F-Ph | 4-F-Ph | H | N |
| 86 | H | H | CH(CH₃)-4-F-Ph | 4-F-Ph | H | N |
| 87 | CH₃ | H | CH(CH₃)-4-F-Ph | 4-F-Ph | H | N |
| 88 | H | CH₃ | 4-F-Ph | 2,4-DiCl-Ph | H | N |
| 89 | CH₃ | CH₃ | 4-F-Ph | 2,4-DiCl-Ph | H | N |
| 90 | H | H | 3-Pyridyl | Ph | H | N |
| 91 | H | H | 4-pyridyl | Ph | H | N |
| 92 | C(=O)CH₃ | H | 4-F-Ph | 2,4-DiCl-Ph | H | N |
| 93 | CH₃ | H | 4-F-Ph | 2,4-DiCl-Ph | SO₂CH₂CN | N |
| 94 | H | H | Ph | Ph | H | N |
| 95 | CH₃ | H | Ph | Ph | H | N |
| 96 | H | H | C(=CH₂)-2,4-DiCl-Ph | 4-F-Ph | H | N |
| 97 | CH₃ | H | C(=CH₂)-2,4-DiCl-Ph | 4-F-Ph | H | N |
| 98 | H | H | C(=CH₂)-4-F-Ph | 2,4-DiCl-Ph | H | N |
| 99 | CH₃ | H | C(=CH₂)-4-F-Ph | 2,4-DiCl-Ph | H | N |
| 100 | CH₃ | H | n-Bu | 4-F-Ph | H | N |
| 101 | C(=O)CH₃ | H | 4-F-Ph | 4-F-Ph | H | N |
| 102 | CHO | H | 4-F-Ph | 4-F-Ph | H | N |
| 103 | CHO | H | 4-F-Ph | 2,4-DiCl-Ph | H | N |
| 104 | CH₃ | H | 2-pyridyl | 2,4-DiCl-Ph | H | N |
| 105 | CH₂CO₂CH₂Ph | H | 4-F-Ph | 4-F-Ph | H | N |
| 106 | H | H | C(CH₃)-2,4-DiCl-Ph | 4-F-Ph | H | N |
| 107 | H | H | C(CH₃)-2,4-DiCl-Ph | 4-F-Ph | H | N |
| 108 | H | H | C(CH₃)-4-F-Ph | 2,4-DiCl-Ph | H | N |
| 109 | H | H | C(CH₃)-4-F-Ph | 2,4-DiCl-Ph | H | N |
| 110 | CH₃ | H | C(CH₃)-4-F-Ph | 2,4-DiCl-Ph | H | N |
| 111 | H | H | 4-NO₂-Ph | 2,4-DiCl-Ph | H | N |
| 112 | CH₃ | H | 4-NO₂-Ph | 2,4-DiCl-Ph | H | N |
| 113 | H | H | cyclopentyl | 4-F-Ph | H | N |
| 114 | CH₃ | H | cyclopentyl | 4-F-Ph | H | N |
| 115 | H | H | cyclohexyl | 2,4-DiCl-Ph | H | N |
| 116 | CH₃ | H | cyclohexyl | 2,4-DiCl-Ph | H | N |
| 117 | H | H | cyclohexyl | 4-F-Ph | H | N |
| 118 | CH₃ | H | cyclohexyl | 4-F-Ph | H | N |
| 119 | H | H | cyclopentyl | 2,4-DiCl-Ph | H | N |
| 120 | CH₃ | H | cyclopentyl | 2,4-DiCl-Ph | H | N |
| 121 | H | H | n-Bu | 2,4-DiCl-Ph | H | N |
| 122 | CH₃ | H | n-Bu | 2,4-DiCl-Ph | H | N |
| 123 | H | H | cyclopropyl | 4-F-Ph | H | N |

TABLE A-continued

| CMPD | R¹ | R² | R³ | AR | Q | Z |
|------|----|----|----|-----|---|---|
| 124 | H | H | cyclopropyl | 2,4-DiCl-Ph | H | N |
| 125 | CH₃ | H | cyclopropyl | 2,4-DiCl-Ph | H | N |
| 126 | H | H | 4-Cl-2-thienyl | 4-F-Ph | H | N |
| 127 | H | H | 2,5-DiCl-3-thienyl | 4-F-Ph | H | N |
| 128 | CH₃ | H | 2,5-DiCl-3-thienyl | 4-F-Ph | H | N |
| 129 | H | H | 5-Cl-2-thienyl | 2,4-DiCl-Ph | H | N |
| 130 | CH | H | 5-Cl-2-thienyl | 2,4-DiCl-Ph | H | N |
| 131 | H | H | 4-CN-Ph | 2,4-DiCl-Ph | H | N |
| 132 | CH₃ | H | 4-CN-Ph | 2,4-DiCl-Ph | H | N |
| 133 | H | H | CH(OH)-4-Cl-Ph | 2,4-DiCl-Ph | H | N |
| 134 | H | H | CH(OH)-4-Cl-Ph | 2,4-DiF-Ph | H | N |
| 135 | CH₂CH₂OH | H | 4-F-Ph | 2,4-DiCl-Ph | H | N |
| 136 | H | H | C(=CH₂)-4-Cl-Ph | 2,4-DiF-Ph | H | N |
| 137 | H | H | C(=CH₂)-4-F-Ph | 2,4-DiF-Ph | H | N |
| 138 | CH₃ | H | C(=CH₂)-4-Cl-Ph | 2,4-DiF-Ph | H | N |
| 139 | H | H | C(CH₃)-4-Cl-Ph | 2,4-DiF-Ph | H | N |
| 140 | H | H | C(CH₃)-4-Cl-Ph | 2,4-DiF-Ph | H | N |
| 141 | H | H | C(CH₃)-4-F-Ph | 2,4-DiF-Ph | H | N |
| 142 | H | H | C(CH₃)-4-F-Ph | 2,4-DiF-Ph | H | N |
| 143 | CH₃ | H | C(SCH₃)-Ph | 2,4-DiF-Ph | H | N |
| 144 | CH₃ | H | C(SCH₃)-Ph | 2,4-DiF-Ph | H | N |
| 145 | CH₃ | H | 4-F-Ph | 2,4-DiCl-Ph | S(O)CH₂SCN | N |
| 146 | CH₃ | H | 4-F-Ph | 2,4-DiCl-Ph | S(O)CH₂SCN | N |
| 147 | CH₃ | H | 4-F-Ph | 2,4-DiCl-Ph | SO₂CH₂SCN | N |
| 148 | H | H | C(SCH₃)-Ph | 2,4-DiF-Ph | H | N |
| 149 | CH₂CH₃ | H | 4-F-Ph | 2,4-DiCl-Ph | H | N |
| 150 | CH₃ | H | C(CH₃)-4-Cl-Ph | 2,4-DiF-Ph | H | N |
| 151 | CH₃ | H | C(CH₃)-4-F-Ph | 2,4-DiF-Ph | H | N |
| 152 | H | H | 4,6-DiCl-2-pyridyl | 4-Cl-Ph | H | N |
| 153 | H | H | C(SCH₃)-4-Cl-Ph | 2,4-DiF-Ph | H | N |
| 154 | H | H | C(SCH₃)-4-Cl-Ph | 2,4-DiF-Ph | H | N |
| 155 | CH₃ | H | C(SCH₃)-4-Cl-Ph | 2,4-DiF-Ph | H | N |
| 156 | CH₃ | H | C(SCH₃)-4-Cl-Ph | 2,4-DiF-Ph | H | N |
| 157 | CH₃ | H | 4,6-DiCl-2-pyridyl | 4-Cl-Ph | H | N |
| 158 | H | H | 4,6-DiCl-2-pyridyl | 4-F-Ph | H | N |
| 159 | CH₃ | H | 4,6-DiCl-2-pyridyl | 4-F-Ph | H | N |
| 160 | CH₂CH₃ | H | 4,6-DiCl-2-pyridyl | 4-F-Ph | H | N |
| 161 | CH₂CH=CH₂ | H | 4,6-DiCl-2-pyridyl | 4-F-Ph | H | N |
| 162 | H | H | t-Bu | 4-Cl-Ph | H | N |
| 163 | CH | H | t-Bu | 4-Cl-Ph | H | N |
| 164 | CH₂CH=CH₂ | H | t-Bu | 4-Cl-Ph | H | N |
| 165 | H | H | CH(OCH₃)-4-F-Ph | 4-F-Ph | H | N |
| 166 | H | H | CH(OCH₃)-4-F-Ph | 4-F-Ph | H | N |
| 167 | H | H | CH(OCH₃)-4-F-Ph | 2,4-DiF-Ph | H | N |
| 168 | H | CH₃ | CH(OCH₃)-4-F-Ph | 2,4-DiCl-Ph | H | N |
| 169 | CH₃ | H | CH(OCH₃)-4-F-Ph | 2,4-DiF-Ph | H | N |
| 170 | CH₃ | H | CH(OCH₃)-4-F-Ph | 2,4-DiCl-Ph | H | N |
| 171 | H | H | CH=CH-(4-Cl-Ph)[cis] | 4-F-Ph | H | N |
| 172 | CH₃ | H | CH=CH-(4-Cl-Ph)[cis] | 4-F-Ph | H | N |
| 173 | H | H | 4-Cl-Ph | 4-Ph-O-Ph | H | N |
| 174 | CH₂CH=CH₂ | H | 4-Cl-Ph | 4-Ph-O-Ph | H | N |
| 175 | CH₃ | H | 4-Cl-Ph | 4-Ph-O-Ph | H | N |
| 176 | H | H | 3-Cl-Ph | 2,4-DiCl-Ph | H | N |
| 177 | CH | H | 3-Cl-Ph | 2,4-DiCl-Ph | H | N |
| 178 | H | H | 4-F-Ph | 3,4-DiCl-Ph | H | N |
| 179 | CH₃ | H | 4-F-Ph | 3,4-DiCl-Ph | H | N |
| 180 | H | H | 4-F-Ph | 2,5-DiCl-Ph | H | N |
| 181 | CH₃ | H | 4-F-Ph | 2,5-DiCl-Ph | H | N |
| 182 | H | H | 4-F-Ph | 3-Cl-Ph | H | N |
| 183 | CH₃ | H | 4-F-Ph | 3-Cl-Ph | H | N |
| 184 | H | H | 4-F-Ph | 2-Cl-Ph | H | N |
| 185 | CH₃ | H | 4-F-Ph | 2-Cl-Ph | H | N |
| 186 | H | H | 2,4-DiCl-benzyl | 4-F-Ph | H | N |
| 187 | CH₃ | H | 2,4-DiCl-benzyl | 4-F-Ph | H | N |
| 188 | CH₂CH=CH₂ | H | 2,4-DiCl-benzyl | 4-F-Ph | H | N |
| 189 | H | H | 4-F-benzyl | 2,4-DiCl-Ph | H | N |
| 190 | CH₃ | H | 4-F-benzyl | 2,4-DiCl-Ph | H | N |
| 191 | H | H | 2,4-DiCl-Ph | 2,4-DiCl-Ph | H | N |
| 192 | CH₃ | H | 2,4-DiCl-benzyl | 2,4-DiCl-Ph | H | N |
| 193 | H | H | 2,4-DiCl-Ph | 3,4-DiCl-Ph | H | N |
| 194 | CH₃ | H | 2,4-DiCl-Ph | 3,4-DiCl-Ph | H | N |
| 195 | H | H | 2-pyridyl | 2,4-DiCl-Ph | H | N |
| 196 | H | H | 3-pyridyl | 2,4-DiCl-Ph | H | N |
| 197 | H | H | n-Bu | 4-CF₃-Ph | H | N |
| 198 | H | H | n-Bu | 4-F-Ph | H | N |
| 199 | CH₃ | H | 4-F-Ph | 2,4-DiCl-Ph | SH | N |
| 200 | CH₃ | H | 4-F-Ph | 2,4-DiCl-Ph | I | N |
| 201 | CH₃ | H | 4-F-Ph | 2,4-DiCl-Ph | Br | N |
| 202 | CH₃ | H | 4-F-Ph | 2,4-DiCl-Ph | SCH₂CN | N |
| 203 | CH₃ | H | 4-F-Ph | 2,4-DiCl-Ph | SCH₂SCN | N |
| 204 | CH₃ | H | 4-F-Ph | 2,4-DiCl-Ph | S(O)CH₂CN | N |

TABLE A-continued

| CMPD | R¹ | R² | R³ | AR | Q | Z |
|---|---|---|---|---|---|---|
| 205 | H | H | 4-n-Bu,5-Cl-2-pyridyl | 2,4-DiCl-Ph | H | N |
| 206 | H | H | CH=CH-(4-Cl-Ph)[trans] | 2,4-DiF-Ph | H | N |
| 207 | H | H | CH$_2$CH$_2$-4-Cl-Ph | 2,4-DiF-Ph | H | N |
| 208 | H | H | 5-Cl-2-pyridyl | 2,4-DiCl-Ph | H | N |
| 209 | H | H | 5-Cl-2-pyridyl | 4-F-Ph | H | N |
| 210 | H | H | 5-Cl-2-pyridyl | 2,4-DiCl-Ph | H | N |
| 211 | CH$_3$ | H | 5-Cl-2-pyridyl | 2,4-DiCl-Ph | H | N |
| 212 | CH$_3$ | H | 5-Cl-2-pyridyl | 4-F-Ph | H | N |
| 213 | CH$_3$ | H | 5-Cl-2-pyridyl | 2,4-DiF-Ph | H | N |
| 214 | H | H | 3,5-DiCl-2-pyridyl | 2,4-DiF-Ph | H | N |
| 215 | CH$_3$ | H | 3,5-DiCl-2-pyridyl | 2,4-DiF-Ph | H | N |
| 216 | H | H | n-Bu | 2,4-DiF-Ph | H | N |
| 217 | H | H | CH(C$_2$H$_5$)-4-F-Ph | 2,4-DiF-Ph | H | N |
| 218 | H | H | CH(C$_2$H$_5$)-4-F-Ph | 2,4-DiF-Ph | H | N |
| 219 | H | H | 2,6-DiF-3-pyridyl | 4-F-Ph | H | N |
| 220 | CH$_3$ | H | 2,6-DiF-3-pyridyl | 4-F-Ph | H | N |
| 221 | H | H | 5-Cl-2-pyridyl | 2,6-DiF-3-pyridyl | H | N |
| 222 | H | H | C(=CH$_2$)-4-F-Ph | 2,6-DiF-3-pyridyl | H | N |
| 223 | H | H | CH(CH$_3$)-4-F-Ph | 2,6-DiF-3-pyridyl | H | N |
| 224 | H | H | CH(CH$_3$)-4-F-Ph | 2,6-DiF-3-pyridyl | H | N |
| 225 | H | H | 4-CH$_3$-S-Ph | 2,4-DiCl-Ph | H | N |
| 226 | CH$_3$ | H | 4-CH$_3$-S-Ph | 2,4-DiCl-Ph | H | N |
| 227 | H | H | 2,6-DiF-Ph | 4-F-Ph | H | N |
| 228 | CH$_3$ | H | 2,6-DiF-Ph | 4-F-Ph | H | N |
| 229 | CH$_2$—C(Br)=CH$_2$ | H | 2,6-DiF-Ph | 4-F-Ph | H | N |
| 230 | H | H | 4-CH$_3$SO$_2$-Ph | 2,4-DiCl-Ph | H | N |
| 231 | CH$_3$ | H | 4-CH$_3$SO$_2$-Ph | 2,4-DiCl-Ph | H | N |
| 232 | H | H | 4-F-Ph | 2,4,5-TRI-Cl-Ph | H | N |
| 233 | CH$_3$ | H | 4-F-Ph | 2,4,5-TRI-Cl-Ph | H | N |
| 234 | CH$_3$ | H | CH(CH$_3$)-4-F-Ph | 2,6-DiF-3-pyridyl | H | N |
| 235 | H | H | CH(=CH$_3$)4-F-Ph | 3,5-DiCl-2-pyridyl | H | N |
| 236 | H | H | 4-Cl-Ph | 3,5-DiCl-2-pyridyl | H | N |
| 237 | CH$_3$ | H | 4-F-Ph | 2,4-DiCl-Ph | CHO | N |
| 238 | H | H | 4-F-Ph | 4-F-Ph | H | CH |
| 239 | H | H | 4-F-Ph | 2,4-DiCl-Ph | H | CH |
| 240 | H | H | 4-F-Ph-CH$_2$ | 2,4-DiCl-Ph | H | CH |
| 241 | CH$_3$ | H | 4-F-Ph | 4-F-Ph | H | CH |
| 242 | CH$_3$ | H | 4-F-Ph | 2,4-DiCl-Ph | H | CH |
| 243 | H | H | 4-Cl-Ph | 2,4-DiCl-Ph | H | CH |
| 244 | CH$_3$ | H | 4-Cl-Ph | 2,4-DiCl-Ph | H | CH |
| 245 | C$_2$H$_5$ | H | 4-F-Ph | 2,4-DiCl-Ph | H | CH |
| 246 | CH$_2$CH=CH$_2$ | H | 4-F-Ph | 2,4-DiCl-Ph | H | CH |
| 247 | H | H | 2,5-DiCl-2-pyridyl | 4-F-Ph | H | CH |

TABLE B

| CMPD | AR | R⁴ | Z | Q |
|---|---|---|---|---|
| 248 | 4-F-Ph | 4-F-Ph | N | H |
| 249 | 4-Cl-Ph | 4-Cl-Ph | N | H |
| 250 | 4-F-Ph | 2-Cl-Ph | N | H |
| 251 | Ph | 3-pyridyl | N | H |
| 252 | 4-F-Ph | 2,4-DiCl-Ph | N | H |
| 253 | Ph | 4-pyridyl | N | H |
| 254 | 2,4-DiCl-Ph | 2-pyridyl | N | H |
| 255 | 2,4-DiCl-Ph | 3-pyridyl | N | H |
| 256 | Ph | Ph | N | H |
| 257 | Ph | Ph | N | H |
| 258 | 4-CN-Ph | 2,4-DiCl-Ph | N | H |
| 259 | 4-Cl-Ph | 3,5-DiCl-2-pyridyl | N | H |
| 260 | 4-F-Ph | 3,5-DiCl-2-pyridyl | N | H |
| 261 | 4-F-Ph | 3,5-DiCl-2-pyridyl | CH | H |
| 262 | 2,4-DiCl-Ph | 4-F-Ph | CH | H |
| 263 | 4-Cl-Ph | 4-F-Ph-O | N | H |
| 264 | 4-Cl-Ph | 4-Cl-Ph-S | N | H |
| 265 | 4-Cl-Ph | 4-Cl-Ph-N(CH3) | N | H |
| 266 | 4-F-Ph | 2,4-DiCl-Ph | N | SH |
| 267 | 4-F-Ph | 2,4-DiCl-Ph | N | SCH$_2$SCN |

Results for Examples 14–26 are given in Table C. In the table, a rating of 100 indicates 100% disease control and a rating of 0 indicates no disease control relative to the controls. NT indicates that no test was performed.

EXAMPLE 14

The test compounds were dissolved in acetone in an amount equal to 6% of the final volume and then suspended at a concentration of 100 or 200 ppm in purified water containing 250 ppm of the surfactant TREM 014 (polyhydric alcohol esters). This suspension was sprayed to the point of run-off on wheat seedlings. The following day plants were inoculated with a spore suspension of *Puccinia reconita*, the causal agent of wheat leaf rust, and incubated in a saturated humidity chamber at 20° C. for 24 hrs and then in a growth chamber at 20° C. for 8 days, when disease ratings were made.

EXAMPLE 15

The test compounds were dissolved in acetone in an amount equal to 6% of the final volume and then suspended at a concentration of 100 or 200 ppm in purified water containing 250 ppm of the surfactant TREM 014 (polyhydric alcohol esters). This suspension was sprayed to the point of run-off on rice seedlings. The following day plants were inoculated with a spore suspension of *Pyricularia oryzae*, the causal agent of rice blast, and incubated in a saturated humidity chamber at 27° C. for 24 hrs and then in a growth chamber at 29° C. for 4 days, when disease ratings were made.

EXAMPLE 16

The test compounds were dissolved in acetone in an amount equal to 6% of the final volume and then suspended at a concentration of 100 or 200 ppm in purified water containing 250 ppm of the surfactant TREM 014 (polyhydric alcohol esters). This suspension was sprayed to the point of run-off on broad bean seedlings. The following day plants were inoculated with a spore suspension of *Botrytis cinerea*, the causal agent of bean grey mold, and incubated in a saturated humidity chamber at 20° C. for 24 hrs when disease ratings were made.

EXAMPLE 17

The test compounds were dissolved in acetone in an amount equal to 6% of the final volume and then suspended at a concentration of 100 or 200 ppm in purified water containing 250 ppm of the surfactant TREM 014 (polyhydric alcohol esters). This suspension was sprayed to the point of run-off on wheat seedlings. The following day plants were inoculated with a spore dust of *Erysiphe graminis* f. sp. tritici, the causal agent of wheat powdery mildew, and incubated in a growth chamber at 20° C. for 6 days, when disease ratings were made.

EXAMPLE 18

The test compounds were dissolved in acetone in an amount equal to 6% of the final volume and then suspended at a concentration of 100 or 200 ppm in purified water containing 250 ppm of the surfactant TREM 014 (polyhydric alcohol esters). This suspension was sprayed to the point of run-off on rice seedlings. The following day plants were inoculated with a spore suspension of *Rhizoctonia solani*, the causal agent of rice sheath blight, and incubated in a saturated humidity chamber at 27° C. for 48 hrs and then om a growth chamber at 29° C. for 4 days, when disease ratings were made.

EXAMPLE 19

The test compounds were dissolved in acetone in an amount equal to 6% of the final volume and then suspended at a concentration of 100 or 200 ppm in purified water containing 250 ppm of the surfactant TREM 014 (polyhydric alcohol esters). This suspension was sprayed to the point of run-off on peanut seedlings. The following day plants were inoculated with a spore suspension of *Cercosporidium personatum*, the causal agent of Peanut Late Leafspot, and incubated in a saturated humidity chamber at 22° C. for for 24 hrs and then in a high humidity chamber at 27° C. for 7 days, and then in a growth chamber at 29° C. for 7 days, when disease ratings were made.

EXAMPLE 20

The test compounds were dissolved in acetone in an amount equal to 6% of the final volume and then suspended at a concentration of 100 or 200 ppm in purified water containing 250 ppm of the surfactant TREM 014 (polyhydric alcohol esters). This suspension was sprayed to the point of run-off on tomato seedlings. The following day plants were inoculated with a spore suspension of *Phytophthora infestans*, the causal agent of tomato late blight, and incubated in a saturated humidity chamber at 20° C. for 24 hrs and then in a growth chamber at 20° C. for 5 days, when disease ratings were made.

EXAMPLE 21

The test compounds were dissolved in acetone in an amount equal to 6% of the final volume and then suspended at a concentration of 100 or 200 ppm in purified water containing 250 ppm of the surfactant TREM 014 (polyhydric alcohol esters). This suspension was sprayed to the point of run-off on grape seedlings. Thee following day plants were inoculated with a spore suspension of *Plasmopara viticola*, the causal agent of grape downy mildew, and incubated in a saturated humidity chamber at 20° C. for 24 hrs and then a growth chamber at 20° C. for 7 days, and then held in a saturated humidity chamber at 20° C. for 24 hrs, when disease ratings were made.

EXAMPLE 22

The test compounds were dissolved in acetone in an amount equal to 6% of the final volume and then suspended at a concentration of 100 or 200 ppm in TREM 014 (polyhydric alcohol esters). This suspension was sprayed to the point of run-off on apple seedlings. The following day plants were inoculated with a spore suspension of (*Venturia inaequalis*, the causal agent of apple scab, and incubated in a saturated humidity chamber at 20° C. for 24 hrs and then in a growth chamber at 22° C. for 11 days, when disease ratings were made.

EXAMPLE 23

The test compounds were dissolved in acetone so that 1 ml of solution yielded concentration of 0.5 kilogram/hectare when added to cotton seeds and soil in pots. Seeds and soil were then inoculated with a mixture of sand, cereal and mycelium of the fungus *Rhizoctonia solani*, causal agent of cotton blight, and incubated in a growth chamber at 30° C. for for 14 days. Disease ratings were then made.

EXAMPLE 24

The test compounds were dissolved in acetone so that 1 ml of solution yielded concentration of 0.5 kilogram/hectare when added to cucumber seeds and soil in pots. Seeds and soil were then inoculated with a mixture of sand, cereal and mycelium of the fungus *Pythium aphanadermatum*, causal agent of cucumber damping off, and incubated in a growth chamber at 30° C. for 14 days. Disease ratings were then made.

EXAMPLE 25

The test compounds were dissolved in acetone so that 1 ml of solution yielded concentration of 0.5 kilogram/hectare when added to lima bean seeds and soil in pots. Seeds and soil were then inoculated with a mixture of sand, cereal and mycelium of the fungus *Sclerotium rolfsii*, causal agent of southern blight, and incubated in a growth chamber at 30° C. for for 14 days. Disease ratings were then made.

EXAMPLE 26

The test compounds were dissolved in acetone so that 1 ml of solution yielded concentration of 0.5 kilogram/hectare when added to cucumber seeds and soil in pots. Seeds and soil were then inoculated with a mixture of sand, cereal and mycelium of the fungus *Fusarium oxysporum*, f. sp. cucumerinum, causal agent of cucumber wilt, and incubated in a growth chamber at 30° C. for for 14 days. Disease ratings were then made.

TABLE C

| CMPD | RATE[1] | EX. 14 | EX. 15 | EX. 16 | EX. 17 | EX. 18 | EX. 19 | EX. 20 | EX. 21 | EX. 22 | EX. 23 | EX. 24 | EX. 25 | EX. 26 |
|---|---|---|---|---|---|---|---|---|---|---|---|---|---|---|
| 1 | 100 | 100 | 51 | 96 | 100 | 36 | 100 | 76 | 0 | 100 | 0 | 0 | 0 | 0 |
| 2 | 100 | 0 | 20 | 0 | 84 | 0 | 95 | 0 | 0 | 0 | 0 | 0 | 0 | 0 |
| 3 | 100 | 80 | 0 | 90 | 98 | 0 | 95 | 0 | 21 | 92 | 0 | 0 | 0 | 0 |
| 4 | 100 | 96 | 0 | 98 | 98 | 0 | 100 | 0 | 85 | 100 | 0 | 0 | 0 | 60 |
| 5 | 100 | 44 | 0 | 88 | 86 | 0 | 100 | 0 | 0 | 54 | 0 | 0 | 0 | 0 |
| 6 | 100 | 0 | 0 | 94 | 96 | 0 | 96 | 0 | 0 | 86 | 0 | 0 | 0 | 0 |
| 7 | 100 | 96 | 0 | 83 | 98 | 0 | 98 | 0 | 92 | 100 | 0 | 0 | 0 | 60 |
| 8 | 100 | 54 | 0 | 90 | 100 | 0 | 96 | 0 | 0 | 86 | 0 | 0 | 0 | 0 |
| 9 | 100 | 54 | 0 | 84 | 98 | 0 | 100 | 0 | 26 | 100 | 0 | 0 | 0 | 0 |
| 10 | 100 | 56 | 0 | 96 | 98 | 0 | 77 | 0 | 44 | 40 | 0 | 0 | 0 | 0 |
| 11 | 100 | 56 | 0 | 96 | 94 | 0 | 95 | 0 | 21 | 81 | 0 | 0 | 0 | 60 |
| 12 | 100 | 100 | 45 | 98 | 100 | 81 | 100 | 0 | 0 | 100 | 0 | 0 | 0 | 0 |
| 13 | 100 | 98 | 20 | 0 | 95 | 23 | 100 | 8 | 58 | 75 | — | — | — | — |
| 14 | 100 | 88 | 56 | 95 | 100 | — | 100 | 0 | 90 | 100 | 0 | 0 | 0 | 50 |
| 15 | 100 | 73 | 56 | 85 | 96 | — | 100 | 0 | 0 | 48 | 0 | 0 | 0 | 0 |
| 16 | 100 | 41 | 56 | 0 | 96 | — | 92 | 0 | 96 | 12 | 0 | 0 | 0 | 80 |
| 17 | 100 | 41 | 2 | 75 | 94 | — | 100 | 0 | 29 | 100 | 0 | 0 | 0 | 80 |
| 18 | 100 | 41 | 56 | 59 | 96 | — | 98 | 0 | 0 | 88 | 0 | 0 | 0 | 0 |
| 19 | 100 | 73 | 80 | 75 | 98 | — | 98 | 0 | 0 2B | 100 | 0 | 0 | 50 | 0 |
| 20 | 100 | 0 | 56 | 0 | 90 | — | 0 | 0 | 29 | 12 2B | 0 | 0 | 0 | 50 |
| 21 | 100 | 73 | 56 | 0 | 94 | — | 98 | 0 | 29 | 72 | 0 | 0 | 0 | 0 |
| 22 | 100 | 41 | 56 | 32 | 96 | — | 96 | 0 | 29 | 96 | 0 | 0 | 0 | 50 |
| 23 | 100 | 95 | 56 | 97 | 100 | — | 98 | 0 | 69 | 88 | 0 | 0 | 0 | 0 |
| 24 | 100 | 95 | 7 | 30 | 66 | 17 | 79 | 8 | 25 | 83 | — | — | — | — |
| 25 | 100 | 41 | 56 | 0 | 94 | — | 100 | 0 | 0 | 88 | 0 | 0 | 0 | 80 |
| 26 | 100 | 73 | 56 | 91 | 98 | — | 82 | 0 | 96 | 100 | 0 | 0 | 0 | 0 |
| 27 | 100 | 88 | 56 | 32 | 100 | — | 98 | 0 | 0 | 72 | 0 | 0 | 0 | 0 |
| 28 | 100 | 88 | 56 | 32 | 99 | — | 98 | 0 | 0 | 88 | 0 | 0 | 0 | 0 |
| 29 | 100 | 41 | 2 | 0 | 98 | — | 82 | 0 | 0 | 88 | 0 | 0 | 0 | 0 |
| 30 | 100 | 0 | 78 | 90 | 100 | 0 | 96 | 86 | 47 | 68 | 0 | 0 | 0 | 0 |
| 31 | 100 | 79 | 0 | 90 | 98 | 19 | 92 | 23 | 0 | 68 | 0 | 0 | 0 | 0 |
| 32 | 100 | 100 | 20 | 86 | 99 | 48 | 100 | 0 | 0 | 77 | 0 | 0 | 0 | 0 |
| 33 | 100 | 79 | 45 | 94 | 93 | 19 | 100 | 0 | 0 | 96 | 0 | 0 | 0 | 0 |
| 34 | 400 | 0 | 2 | 0 | 72 | — | 92 | 0 | 0 | 12 | 0 | 0 | 0 | 0 |
| 35 | 100 | 0 | 28 | 24 | 77 | 0 | 31 | 0 | 25 | 25 2 | — | — | — | — |
| 36 | 500 | 0 | 0 | 0 | 35 | 0 | 3 | 0 | 0 | 0 2B | 0 | 0 | 0 | 90 |
| 37 | 100 | 80 | 31 | 72 | 94 | 0 | 0 | 0 | 0 | 65 | 0 | 0 | 0 | 50 |
| 38 | 100 | 95 | 0 | 44 | 86 | 0 | 77 | 0 | 82 | 22 | 0 | 0 | 0 | 100 |
| 39 | 100 | 0 | 13 | 66 | 78 | 0 | 77 | 0 | 91 | 54 | 0 | 0 | 0 | 0 |
| 40 | 100 | 54 | 0 | 55 | 100 | 36 | 96 | 23 | 26 | 68 | 0 | 0 | 0 | 0 |
| 41 | 100 | 0 | 78 | 90 | 84 | 0 | 92 | 0 | 0 | 68 | 0 | 0 | 0 | 80 |
| 42 | 100 | 87 | 73 | 20 | 53 | 19 | 96 | 0 | 92 | 89 | 0 | 0 | 0 | 0 |
| 43 | 100 | 94 | 41 | 20 | 72 | 0 | 96 | 0 | 22 | 89 | 0 | 0 | 0 | 0 |
| 44 | 100 | 33 | 0 | 52 | 22 | 0 | 80 | 68 | 0 | 51 2H | 0 | 0 | 0 | 0 |
| 45 | 100 | 0 | 3 | 0 | 29 | 0 | 58 | 0 | 0 | 53 | 0 | 0 | 0 | 100 |
| 46 | 100 | 77 | 3 | 0 | 57 | 0 | 23 | 25 | 0 | 75 | 0 | 0 | 0 | 0 |
| 47 | 100 | 0 | 3 | 54 | 29 | 0 | 0 | 0 | 0 | 53 | 0 | 0 | 0 | 0 |
| 48 | 100 | 80 | 0 | 90 | 94 | 0 | 98 | 0 | 0 | 97 | 0 | 0 | 0 | 70 |
| 49 | 100 | 80 | 0 | 96 | 94 | 0 | 77 | 0 | 44 | 97 | 0 | 0 | 0 | 70 |
| 50 | 100 | 54 | 51 | 73 | 98 | 0 | 92 | 62 | 0 | 68 | 0 | 0 | 0 | 0 |
| 51 | 100 | 0 | 20 | 0 | 84 | 0 | 75 | 0 | 17 | 56 | 0 | 0 | 0 | 0 |
| 52 | 100 | 98 | 20 | 95 | 98 | 34 | 100 | 0 | 0 | 77 | 0 | 0 | 0 | 70 |
| 53 | 100 | 79 | 45 | 0 | 81 | 0 | 47 | 0 | 86 | 96 | 0 | 0 | 0 | 0 |
| 54 | 100 | 88 | 2 | 59 | 100 | — | 98 | 0 | 0 | 100 | 0 | 0 | 0 | 50 |
| 55 | 400 | 41 | 56 | 91 | 72 | — | 82 | 0 | 100 | 88 | 0 | 0 | 0 | 0 |
| 56 | 100 | 41 | 2 | 97 | 90 | — | 92 | 0 | 29 | 12 | 0 | 0 | 0 | 0 |
| 57 | 100 | 41 | 2 | 75 | 90 | — | 65 | 0 | 0 | 48 | 0 | 0 | 0 | 0 |
| 58 | 100 | 88 | 2 | 75 | 94 | — | 82 | 0 | 0 | 72 | 30 | 0 | 0 | 60 |
| 59 | 100 | 73 | 2 | 32 | 96 | — | 96 | 0 | 29 | 96 | 0 | 0 | 0 | 0 |
| 60 | 100 | 41 | 2 | 75 | 90 | — | 96 | 0 | 0 | 12 | 0 | 0 | 0 | 0 |
| 61 | 100 | 41 | 2 | 32 | 94 | — | 65 | 0 | 0 | 96 | 0 | 0 | 0 | 0 |
| 62 | 100 | 73 | 56 | 0 | 83 | — | 96 | 0 | 0 | 12 | 0 | 0 | 0 | 0 |
| 63 | 100 | 96 | 0 | 81 | 95 | 0 | 28 | 45 | 0 | 60 | 0 | 0 | 0 | 0 |
| 64 | 100 | 41 | 2 | 0 | 90 | — | 96 | 0 | 69 | 0 | 0 | 0 | 0 | 0 |
| 65 | 100 | 41 | 2 | 32 | 83 | — | 98 | 0 | 0 | 12 | 0 | 0 | 0 | 0 |
| 66 | 100 | 53 | 0 | 49 | 39 | 0 | 28 | 0 | 0 | 33 | 0 | 0 | 0 | 0 |
| 67 | 100 | 41 | 2 | 32 | 83 | — | 0 | 0 | 0 | 12 | 0 | 0 | 0 | 0 |
| 68 | 100 | 41 | 2 | 32 | 96 | — | 98 | 0 | 0 | 12 | 0 | 0 | 0 | 0 |
| 69 | 100 | 84 | 0 | 25 | 75 | 0 | 21 | 31 | 0 | 0 | — | — | — | — |
| 70 | 100 | 73 | 2 | 0 | 83 | — | 98 | 0 | 51 | 48 | 0 | 0 | 0 | 0 |
| 71 | 100 | 94 | 0 | 0 | 95 | — | 52 | 0 | — | 72 | — | — | — | — |
| 72 | 100 | 79 | 0 | 0 | 0 | 0 | 28 | 0 | 0 | 100 | 0 | 0 | 0 | 0 |
| 73 | 100 | 91 | 0 | 69 | 63 | 0 | 61 | 0 | 62 | 79 | 0 | 0 | 0 | 0 |
| 74 | 100 | 93 | 0 | 7 | 98 | 0 | 79 | 0 | 15 | 87 | — | — | — | — |
| 75 | 100 | 100 | 33 | 61 | 97 | 0 | 100 | 7 | 25 | 76 | — | — | — | — |
| 76 | 100 | 79 | 0 | 69 | 78 | 0 | 80 | 0 | 22 2B | 97 | 0 | 0 | 0 | 0 |
| 77 | 100 | 53 | 0 | 0 | 39 | 0 | 80 | 0 | 0 | 0 | 0 | 0 | 0 | 0 |
| 78 | 100 | 84 | 0 | 7 | 95 | 0 | 42 | 68 | 0 | 22 | — | — | — | — |
| 79 | 100 | 96 | 0 | 81 | 95 | 62 | 100 | 0 | 0 | 100 | 0 | 0 | 0 | 0 |
| 80 | 100 | 91 | 0 | 89 | 98 | 50 | 100 | 0 | 22 2B | 100 | 0 | 0 | 0 | 0 |

TABLE C-continued

| CMPD | RATE[1] | EX. 14 | EX. 15 | EX. 16 | EX. 17 | EX. 18 | EX. 19 | EX. 20 | EX. 21 | EX. 22 | EX. 23 | EX. 24 | EX. 25 | EX. 26 |
|---|---|---|---|---|---|---|---|---|---|---|---|---|---|---|
| 81 | 100 | 53 | 0 | 0 | 87 | 0 | 28 | 0 | 22 | 0 | 0 | 0 | 0 | 0 |
| 82 | 100 | 79 | 0 | 81 | 97 | 0 | 96 | 0 | 0 | 91 | 0 | 0 | 0 | 0 |
| 83 | 100 | 91 | 0 | 81 | 95 | 62 | 100 | 0 | 0 | 91 | 0 | 0 | 0 | 0 |
| 84 | 100 | 96 | 58 | 69 | 95 | 19 | 91 | 23 | 0 | 79 | 0 | 0 | 0 | 0 |
| 85 | 100 | 41 | 2 | 32 | 94 |  | 65 | 0 | 0 | 12 | 0 | 0 | 0 | 0 |
| 86 | 100 | 100 | 0 | 93 | 95 | 97 | 100 | 0 | 0 | 100 | 0 | 0 | 0 | 0 |
| 87 | 100 | 96 | 0 | 0 | 92 | 19 | 0 | 0 | 0 | 60 | 0 | 0 | 0 | 0 |
| 88 | 100 | 97 | 0 | 59 | 97 | 100 | 83 | 0 | 77 | 100 | 0 | 0 | 0 | 0 |
| 89 | 100 | 0 | 0 | 75 | 95 | 0 | 0 | 19 | 100 | 0 | 0 | 0 | 0 | 0 |
| 90 | 100 | 37 | 0 | 0 | 0 | 41 | 0 | 0 | 0 | 0 | 0 | 0 | 0 |  |
| 91 | 100 | — | 72 | — | — | — | — | — | — | — | 0 | 0 | 0 | 0 |
| 92 | 500 | 100 | 22 | 92 | 100 | 0 | 100 | 0 | 63 | 100 | 0 | 0 | 0 | 0 |
| 93 | 100 | 94 | 0 | 98 | 96 | 19 | 100 | 0 | 18 | 100 | 0 | 0 | 0 | 0 |
| 94 | 500 | 87 | 22 | 78 | 100 | 0 | 73 | 24 | 24 | 24 | 0 | 0 | 0 | 0 |
| 95 | 500 | 0 | 22 | 0 | 91 | 0 | 97 | 0 | 0 | 60 | 0 | 0 | 0 | 80 |
| 96 | 500 | 60 | 0 | 0 | 99 | — | 59 | 18 | 0 | 0 | 0 | 0 | 0 | 0 |
| 97 | 500 | 82 | 0 | 0 | 100 | — | 91 | 0 | 25 | 67 | 0 | 0 | 0 | 0 |
| 98 | 500 | 82 | 0 | 0 | 100 | 59 | 100 | 0 | 76 | 85 | 0 | 0 | 0 | 0 |
| 99 | 500 | 96 | 51 | 0 | 100 | 30 | 91 | 0 | 86 | 95 | 0 | 0 | 0 | 0 |
| 100 | 500 | 36 | 54 | 0 | 98 | 0 | 78 | 22 | 9 | 13 | 0 | 0 | 0 | 50 |
| 101 | 500 | 36 | 22 | 39 | 97 | 0 | 3 | 0 | 0 | 24 | 0 | 0 | 0 | 0 |
| 102 | 200 | 97 | 79 | 36 | 100 | 0 | 100 | 22 | 35 | 80 | 0 | 0 | 0 | 0 |
| 103 | 200 | 97 | 79 | 36 | 100 | 0 | 100 | 0 | 0 | 94 | 0 | 0 | 0 | 0 |
| 104 | 500 | 97 | 91 | 97 | 100 | 0 | 100 | 44 | 71 | 94 | 0 | 0 | 0 | 0 |
| 105 | 200 | 55 | 0 | 45 | 94 | 90 | 79 | 0 | 0 | 0 | 0 | 0 | 0 | 0 |
| 106 | 100 | 99 | 16 | 21 | 100 | 0 | 99 | 0 | 30 | 81 | — | — | — | — |
| 107 | 100 | 38 | 5 | 61 | 97 | 0 | 38 | 0 | 8 | 7 | — | — | — | — |
| 108 | 100 | 100 | 11 | 71 | 100 | 0 | 100 | 0 | 51 | 100 | — | — | — | — |
| 109 | 100 | 99 | 16 | 36 | 99 | — | 100 | 0 | 15 | 94 | — | — | — | — |
| 110 | 100 | 100 | 16 | 21 | 100 | 0 | 99 | 0 | 30 | 91 | — | — | — | — |
| 111 | 200 | 98 | 0 | 91 | 98 | 36 | 100 | 0 | 78 | 68 | 0 | 0 | 0 | 0 |
| 112 | 200 | 98 | 51 | 97 | 100 | 50 | 100 | 0 | 18 | 100 | 0 | 0 | 0 | 0 |
| 113 | 200 | 0 | 0 | 0 | 94 | 62 | 100 | 0 | 0 | 93 | 60 | 0 | 0 | 100 |
| 114 | 200 | 49 | 0 | 0 | 83 | 72 | 87 | 0 | 0 | 50 | 0 | 0 | 0 | 100 |
| 115 | 200 | 100 | 0 | 91 | 100 | 72 | 100 | 21 | 0 | 100 | 0 | 0 | 0 | 0 |
| 116 | 200 | 49 | 0 | 76 | 100 | 0 | 94 | 46 | 86 | 100 | 0 | 0 | 0 | 100 |
| 117 | 200 | 49 | 0 | 0 | 83 | 72 | 87 | 0 | 0 | 50 | 0 | 0 | 0 | 100 |
| 118 | 200 | 0 | 0 | 33 | 83 | 0 | 47 | 0 | 25 | 50 | 0 | 0 | 0 | 0 |
| 119 | 200 | 100 | 0 | 91 | 100 | 97 | 100 | 46 | 0 | 93 | 0 | 0 | 0 | 100 |
| 120 | 200 | 98 | 0 | 76 | 100 | 62 | 100 | 21 | 0 | 100 | 0 | 0 | 0 | 100 |
| 121 | 200 | 77 | 57 | 80 | 100 | 36 | 100 | 0 | 0 | 100 | 50 | 0 | 0 | 0 |
| 122 | 200 | 49 | 3 | 67 | 99 | 0 | 95 | 0 | 0 | 100 | 0 | 0 | 0 | 0 |
| 123 | 500 | 0 2B | 22 | 0 | 98 | 0 | 73 | 0 | 0 | 94 | 0 | 0 | 0 | 0 |
| 124 | 200 | 90 | 57 | 8 | 100 | 19 | 100 | 0 | 0 | 86 | 50 | 0 | 0 | 0 |
| 125 | 200 | 49 | 3 | 44 | 100 | 0 | 100 | 0 | 0 | 95 | 0 | 0 | 0 | 0 |
| 126 | 500 | 0 | 22 | 78 | 35 | 0 | 0 | 24 | 24 | 24 | 0 | 0 | 0 | 0 |
| 127 | 200 | 77 | 3 | 67 | 100 | 19 | 100 | 0 | 0 | 67 | 0 | 0 | 0 | 0 |
| 128 | 200 | 77 | 57 | 80 | 100 | 0 | 95 | 0 | 26 | 100 | 0 | 0 | 0 | 0 |
| 129 | 200 | 90 | 3 | 44 | 100 | 36 | 100 | 26 | 77 | 95 | 0 | 0 | 0 | 0 |
| 130 | 200 | 79 | 18 | 77 | 100 | 0 | 100 | 0 | 99 | 100 | 0 | 0 | 0 | 0 |
| 131 | 200 | 98 | 0 | 95 | 100 | 0 | 98 | 0 | 0 | 100 | 0 | 0 | 0 | 0 |
| 132 | 200 | 100 | — | 98 | 100 | 0 | 98 | 0 | 23 | 100 | 0 | 0 | 0 | 0 |
| 133 | — | — | — | — | — | — | — | — | — | — | — | — | — | — |
| 134 | — | — | — | — | — | — | — | — | — | — | — | — | — | — |
| 135 | 200 | 0 | 78 | 80 | 96 | 83 | 90 | 47 | 25 | 64 | 0 | 0 | 0 | 0 |
| 136 | 200 | 98 | 0 | 81 | 99 | 0 | 100 | 0 | 99 | 72 | 0 | 0 | 0 | 0 |
| 137 | 200 | 100 | 0 | 12 | 100 | 69 | 100 | 0 | 46 | 88 | 0 | 0 | 0 | 50 |
| 138 | 200 | 100 | 0 | 12 | 100 | 93 | 94 | 0 | 93 | 88 | 0 | 0 | 0 | 0 |
| 139 | 200 | 100 | 0 | 93 | 100 | 83 | 100 | 0 | 93 | 100 | 70 | 0 | 0 | 0 |
| 140 | 200 | 95 | 0 | 93 | 100 | 0 | 97 | 0 | 25 | 88 | 0 | 0 | 90 | 0 |
| 141 | 200 | 100 | 0 | 98 | 100 | 100 | 100 | 0 | 76 | 100 | 0 | 0 | 0 | 0 |
| 142 | 200 | 95 | 0 | 12 | 100 | 100 | 100 | 0 | 0 | 48 | 70 | 0 | 0 | 70 |
| 143 | 200 | 52 | 0 | 3 2B | 91 | 36 | 77 | 0 | 0 | 17 | 0 | 0 | 0 | 0 |
| 144 | 200 | 52 | 0 | 91 | 59 | 0 | 95 | 0 | 0 | 17 | 0 | 0 | 0 | 0 |
| 145 | 200 | 79 | 0 | 97 | 100 | 50 | 100 | 93 | 100 | 74 | 0 | 0 | 0 | 0 |
| 146 | 200 | 52 | 52 | 95 | 100 | 50 | 100 | 77 | 99 | 74 | 0 | 0 | 0 | 0 |
| 147 | 200 | 98 | 52 | 98 | 100 | 73 | 100 | 64 | 100 | 96 | 0 | 0 | 0 | 0 |
| 148 | 200 | 52 | 0 | 98 | 100 | 62 | 100 | 0 | 0 | 51 | 0 | 0 | 0 | 0 |
| 149 | 200 | 100 | 57 | 97 | 100 | 36 | 100 | 0 | 26 | 100 | 0 | 0 | 0 | 0 |
| 150 | 200 | 100 | 3 | 8 | 100 | 19 | 100 | 0 | 77 | 67 | 50 | 0 | 0 | 0 |
| 151 | 200 | 100 | 3 | 44 | 100 | 19 | 77 | 0 | 26 | 67 | 0 | 0 | 0 | 0 |
| 152 | 200 | 96 | 25 | 75 | 100 | 0 | 100 | 0 | 0 | 96 | 0 | 0 | 0 | 0 |
| 153 | 200 | 98 | 11 | 94 | 100 | 50 | 100 | 0 | 24 | 3 | 0 | 0 | 0 | 0 |
| 154 | 200 | 76 | 11 | 0 | 95 | 0 | 79 | 26 | 24 | 3. | 0 | 0 | 0 | 0 |
| 155 | 200 | 98 | 11 | 0 | 98 | 34 | 59 | 0 | 63 | 42 | 50 | 0 | 0 | 0 |
| 156 | 200 | 46 | 11 | 0 | 91 | 0 | 59 | 0 | 0 | 3 | 0 | 0 | 0 | 0 |
| 157 | 40 | 79 | 18 | 86 | 99 | 0 | 96 | 0 | 0 | 100 | — | — | — | — |
| 158 | 40 | 59 | 36 | 96 | 100 | 0 | 100 | 0 | 0 | 100 | 0 | 0 | 0 | 60 |
| 159 | 40 | 7 | 0 | 80 | 100 | 0 | 77 | 0 | 0 | 65 | 0 | 0 | 0 | 0 |
| 160 | 200 | 81 | 0 | 92 | 100 | 19 | 100 | 0 | 0 | 65 | 0 | 0 | 0 | 76 |

TABLE C-continued

| CMPD | RATE[1] | EX. 14 | EX. 15 | EX. 16 | EX. 17 | EX. 18 | EX. 19 | EX. 20 | EX. 21 | EX. 22 | EX. 23 | EX. 24 | EX. 25 | EX. 26 |
|---|---|---|---|---|---|---|---|---|---|---|---|---|---|---|
| 161 | 200 | 100 | 49 | 92 | 100 | 0 | 100 | 0 | 53 | 65 | 0 | 0 | 0 | 0 |
| 162 | 200 | 80 | 1 | 52 | 100 | 0 | 100 | 0 | 76 | 56 | 0 | 0 | 0 | 0 |
| 163 | 200 | 80 | 1 | 0 | 100 | 0 | 96 | 0 | 0 | 17 | 0 | 0 | 0 | 0 |
| 164 | 200 | 0 | 0 | 0 | 99 | 0 | 0 | 0 | 0 | 17 | 0 | 0 | 0 | 0 |
| 165 | 200 | 55 | 1 | 89 | 100 | 0 | 100 | 0 | 0 | 17 | 0 | 0 | 0 | 0 |
| 166 | 200 | 0 | 1 | 83 | 98 | 0 | 16 | 0 | 24 | 56 | 0 | 0 | 0 | 0 |
| 167 | 200 | 90 | 25 | 98 | 100 | 0 | 98 | 0 | 45 | 100 | 0 | 0 | 0 | 0 |
| 168 | 200 | 98 | 25 | 98 | 99 | 19 | 98 | 0 | 45 | 64 | 0 | 0 | 0 | 0 |
| 169 | 200 | 52 | 0 | 0 | 100 | 0 | 33 | 0 | 23 | 0 | 0 | 0 | 0 | 80 |
| 170 | 200 | 100 | 0 | 56 | 100 | 0 | 64 | 0 | 23 | 0 | 0 | 0 | 0 | 0 |
| 171 | 200 | 100 | 0 | 98 | 100 | 0 | 98 | 0 | 0 | 33 | 0 | 0 | 0 | 0 |
| 172 | 200 | 79 | 0 | 27 | 100 | 0 | 33 | 0 | 23 | 0 | 0 | 0 | 0 | 70 |
| 173 | 200 | — | 0 | 80 | 61 | 19 | 97 | 0 | — | 68 | — | — | — | — |
| 174 | 200 | — | 0 | 10 | 95 | 0 | 4 | 0 | — | 0 | — | — | — | — |
| 175 | 200 | — | 0 | 10 | 97 | 0 | 87 | 0 | — | 68 | — | — | — | — |
| 176 | 100 | 97 | 0 | 0 | 85 | 0 | 64 | 0 | 0 | 46 | 0 | 0 | 0 | 0 |
| 177 | 100 | 28 | 0 | 59 | 98 | 22 | 96 | 19 | 11 | 87 | 0 | 0 | 0 | 0 |
| 178 | 100 | 86 | 0 | 85 | 91 | 0 | 83 | 19 | 0 | 46 | 0 | 0 | 0 | 0 |
| 179 | 100 | 0 | 0 | 32 | 75 | 22 | 29 | 0 | 95 | 46 | 0 | 0 | 0 | 0 |
| 180 | 200 | 83 | 0 | 95 | 99 | 0 | 96 | 0 | 0 | 0 | 0 | 0 | 0 | 0 |
| 181 | 200 | 98 | 51 | 91 | 100 | 36 | 96 | 0 | 78 | 100 | 0 | 0 | 0 | 80 |
| 182 | 200 | 92 | 0 | 95 | 100 | 0 | 96 | 0 | 0 | 96 | &E | 70 | 0&E | &E |
| 183 | 200 | 62 | 0 | 85 | 96 | 0 | 82 | 0 | 64 | 86 | 50 | 0 | 0 | 0 |
| 184 | 200 | 83 | 0 | 91 | 100 | 0 | 96 | 0 | 89 | 68 | 0 | 0 | 0 | 0 |
| 185 | 200 | 98 | 0 | 95 | 100 | 0 | 100 | 0 | 89 | 96 | 0 | 80 | 0 | 0 |
| 186 | 200 | 83 | 0 | 0 | 94 | 0 | 26 | 0 | 44 | 0 | 0 | 0 | 0 | 0 |
| 187 | 200 | 62 | 0 | 85 | 94 | 0 | 26 | 0 | 18 | 68 | 0 | 0 | 0 | 0 |
| 188 | 200 | 62 | 0 | 85 | 94 | 50 | 62 | 0 | 44 | 86 | 0 | 0 | 0 | 0 |
| 189 | 200 | 92 | 0 | 85 | 100 | 50 | 96 | 0 | 89 | 39 2B | 0 | 0 | 0 | 0 |
| 190 | 200 | 83 | 0 | 0 | 99 | 0 | 62 | 0 | 98 | 86 | 0 | 0 | 0 | 0 |
| 191 | 200 | 83 | 0 | 60 | 100 | 0 | 62 | 0 | 95 | 68 | 0 | 0 | 0 | 0 |
| 192 | 200 | 62 | 0 | 0 | 98 | 0 | 62 | 0 | 64 | 86 | 0 | 0 | 0 | 0 |
| 193 | 200 | 62 | — | 0 | 89 | 0 | 92 | 0 | 0 | 0 | 0 | | 0 | 0 |
| 194 | 200 | 62 | — | 85 | 100 | 0 | 82 | 0 | 0 | 68 | 0 | 0 | 0 | 0 |
| 195 | 100 | 72 | — | 0 | 83 | 0 | 97 | 0 | 0 | 65 | 0 | 0 | — | 0 |
| 196 | 100 | 72 | — | 53 | 71 | 0 | 41 | 0 | 0 | 34 | 0 | 0 | 0 | 0 |
| 197 | 100 | 37 | — | 0 | 52 | 0 | 0 | 0 | 0 | 0 | 0 | 0 | 0 | 0 |
| 198 | 100 | 72 | — | 22 | 52 | 0 | 70 | 0 | 0 | 0 | 0 | 0 | 0 | 90 |
| 199 | 100 | 94 | 0 | 90 | 94 | 19 | 97 | 0 | 0 | 95 | 0 | 0 | 0 | 0 |
| 200 | 100 | 97 | 55 | 0 | 100 | 19 | 100 | 0 | 74 | 95 | 0 | 0 | 0 | 0 |
| 201 | 100 | 37 | 55 | 22 | 71 | 0 | 41 | 0 | 0 | 0 | 0 | 0 | 0 | 0 |
| 202 | 100 | 37 | 0 | 22 | 94 | 0 | 41 | 0 | 18 | 34 | 0 | 0 | 0 | 0 |
| 203 | 100 | 72 | 0 | 0 | 96 | 19 | 86 | 0 | 0 | 95 | 0 | 0 | 0 | 0 |
| 204 | 100 | 87 | 55 | 96 | 99 | 19 | 100 | 0 | 0 | 65 | 0 | 0 | 0 | 0 |
| 205 | 500 | — | 16 | 0 | 100 | 19 | 94 | 0 | — | 86 | — | — | — | — |
| 206 | 200 | — | 0 | 71 | 98 | 50 | 100 | 0 | — | 98 | — | — | — | — |
| 207 | 200 | — | 0 | 71 | 98 | 81 | 100 | 0 | — | 100 | — | — | — | — |
| 208 | 200 | — | 0 | 94 | 99 | 62 | 100 | 0 | — | 100 | — | — | — | — |
| 209 | 200 | — | 22 | 71 | 100 | 0 | 100 | 0 | — | 83 | — | — | — | — |
| 210 | 200 | — | 22 | 71 | 100 | 0 | 100 | 0 | — | 98 | — | — | — | — |
| 211 | 200 | — | 65 | 83 | 100 | 73 | 100 | 0 | — | 100 | — | — | — | — |
| 212 | 200 | — | 22 | 0 | 76 | 0 | 16 | 0 | — | 45 | — | — | — | — |
| 213 | 200 | — | 65 | 94 | 100 | 19 | 100 | 0 | — | 100 | — | — | — | — |
| 214 | 200 | — | 65 | 83 | 100 | 50 | 100 | 0 | — | 100 | — | — | — | — |
| 215 | 200 | — | 65 | 83 | 100 | 0 | 100 | 0 | — | 100 | — | — | — | — |
| 216 | 200 | — | 52 | 0 | 98 | 0 | 100 | 14 | — | 73 2B | — | — | — | — |
| 217 | — | — | — | — | — | — | — | — | — | — | — | — | — | — |
| 218 | — | — | — | — | — | — | — | — | — | — | — | — | — | — |
| 219 | 200 | — | 0 | 79 | 98 | 0 | — | 0 | — | — | — | — | — | — |
| 220 | 200 | — | 0 | 87 | 96 | 0 | — | 0 | — | — | — | — | — | — |
| 221 | 200 | — | 0 | 42 | 90 | 0 | — | 0 | — | — | — | — | — | — |
| 222 | 200 | — | 5 | 4 | 84 | 0 | — | 0 | — | — | — | — | — | — |
| 223 | 200 | — | 5 | 87 | 84 | 0 | — | 0 | — | — | — | — | — | — |
| 224 | 200 | — | 92 | 0 | 73 | 0 | — | 0 | — | — | — | — | — | — |
| 225 | 200 | — | 84 | 83 | 85 | 0 | 16 | 0 | — | 92 | — | — | — | — |
| 226 | 200 | — | 0 | 90 | 95 | 0 | 57 | 0 | — | 83 | — | — | — | — |
| 227 | 200 | — | 0 | 21 | 98 | 0 | 100 | 0 | — | 100 | — | — | — | — |
| 228 | 200 | — | 0 | 0 | 91 | 0 | 16 | 0 | — | 83 | — | — | — | — |
| 229 | 200 | — | 65 | 21 | 76 | 0 | 57 | 0 | — | 15 | — | — | — | — |
| 230 | 200 | — | 52 | 0 | 60 | 0 | 43 | 0 | — | 14 | — | — | — | — |
| 231 | 200 | — | 79 | 0 | 60 | 0 | 86 | 0 | — | 49 | — | — | — | — |
| 232 | — | — | — | — | — | — | — | — | — | — | — | — | — | — |
| 233 | — | — | — | — | — | — | — | — | — | — | — | — | — | — |
| 234 | 200 | — | — | 11 | — | — | — | — | — | — | — | — | — | — |
| 235 | 200 | — | — | 81 | — | — | — | — | — | — | — | — | — | — |
| 236 | 200 | — | — | 47 | — | — | — | — | — | — | — | — | — | — |
| 237 | — | — | — | — | — | — | — | — | — | — | — | — | — | — |
| 238 | 100 | 0 | 2 | 91 | 83 | — | 92 | 0 | 0 | 72 | 0 | 0 | 0 | 0 |
| 239 | 100 | 73 | 2 | 97 | 90 | — | 98 | 0 | 69 | 72 | 30 | 0 | 0 | 0 |
| 240 | 100 | 41 | 2 | 91 | 90 | — | 96 | 0 | 96 | 88 | 0 | 0 | 0 | 0 |

TABLE C-continued

| CMPD | RATE[1] | EX. 14 | EX. 15 | EX. 16 | EX. 17 | EX. 18 | EX. 19 | EX. 20 | EX. 21 | EX. 22 | EX. 23 | EX. 24 | EX. 25 | EX. 26 |
|---|---|---|---|---|---|---|---|---|---|---|---|---|---|---|
| 241 | 100 | 89 | 16 | 93 | 91 | 53 | 89 | 51 | 0 | 85 | — | — | — | — |
| 242 | 100 | 100 | 0 | 97 | 75 | 100 | 92 | 42 | 11 | 72 | 0 | 0 | 0 | 0 |
| 243 | 200 | 91 | 0 | 97 | 100 | 19 | 96 | 26 | 0 | 62 | 0 | 0 | 0 | 0 |
| 244 | 200 | 79 | 84 | 98 | 99 | 19 | 98 | 0 | 45 | 62 | 0 | 0 | 0 | 0 |
| 245 | 200 | 98 | 99 | 95 | 100 | 73 | 100 | 0 | 23 | 83 | 0 | 0 | 0 | 0 |
| 246 | 200 | 98 | 84 | 97 | 100 | 62 | 98 | 0 | 63 | 62 | 0 | 0 | 0 | 0 |
| 247 | 200 | 0 | 0 | 93 | 97 | 62 | 100 | 0 | 0 | 0 | 0 | 0 | 0 | 80 |
| 248 | 100 | 96 | 96 | 96 | 98 | 17 | — | 0 | 6 | 74 | 50 | 0 | 90 | 80 |
| 249 | — | — | — | — | — | — | — | — | — | — | — | — | — | — |
| 250 | 100 | 87 | 0 | 0 | 91 | 0 | 100 | 0 | 22 | 88 | 0 | 0 | 0 | 0 |
| 251 | 100 | 53 | 0 | 0 | 0 | 0 | 91 | 0 | 0 | 0 | 0 | 0 | 0 | 0 |
| 252 | 100 | 100 | 0 | 0 | 100 | 0 | 100 | 0 | 0 | 100 | 0 | 0 | 0 | 0 |
| 253 | 100 | 20 | 2 | 0 | 0 | — | 0 | 0 | 46 | 40 | 0 | 0 | 0 | 0 |
| 254 | 100 | 87 | — | 0 | 90 | 0 | 97 | 0 | 0 | 65 | 0 | 0 | 0 | 0 |
| 255 | 100 | 87 | — | 0 | 83 | 0 | 97 | 0 | 18 | 95 | 0 | 0 | 0 | 0 |
| 256 | 100 | 72 | 0 | 22 | 90 | 0 | 97 | 0 | 0 | 65 | 0 | 0 | 0 | 0 |
| 257 | 500 | 49 | 0 | 47 | 100 | 69 | 73 | 0 | 100 | 72 3B | 0 | 0 | 0 | 0 |
| 258 | 200 | 90 | 3 | 44 | 100 | 0 | 95 | 0 | 0 | 86 | 0 | 0 | 0 | 0 |
| 259 | 200 | 79 | 0 | 0 | 100 | 0 | 86 | 0 | 0 | 48 | 50 | 0 | 0 | 0 |
| 260 | 40 | 7 | 0 | 0 | 100 | 0 | 55 | 0 | 0 | 100 | 0 | 0 | 0 | 0 |
| 261 | 200 | 90 | 84 | 99 | 100 | 0 | 98 | 0 | 21 | 84 | 0 | 0 | 0 | 50 |
| 262 | 200 | — | 65 | 100 | 100 | 100 | 100 | 0 | — | 100 | — | — | — | — |
| 263 | 200 | — | 22 | 71 | 100 | 19 | 57 | 0 | — | 83 | — | — | — | — |
| 264 | 200 | — | 22 | 52 | 95 | 0 | 16 | 0 | — | 67 | — | — | — | — |
| 265 | 200 | — | 65 | 90 | 99 | 0 | 96 | 0 | — | 98 | — | — | — | — |
| 266 | — | — | — | — | — | — | — | — | — | — | — | — | — | — |
| 267 | — | — | — | — | — | — | — | — | — | — | — | — | — | — |

[1] Concentration in ppm refers to examples 14-22.
2 Letter rating refers to observed phytotoxicity.
3. Dash (—) indicates not tested.

I claim:
1. A compound having the formula:

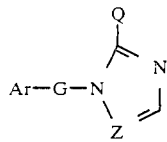
                                  I wherein
Ar is phenyl, pyridyl or thienyl each substituted with 1-3 substituents selected from $R^5$, $R^6$ and $R^7$;
Z is N;
Q is H, $S(O)_nR^{18}$, halogen, CHO, $C_1$-$C_4$ alkyl, or SH and its corresponding disulfide;
n is 0, 1 or 2;
G is

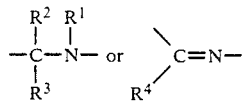

where the nitrogen is bonded to the triazole;
$R^1$ is H, $C_1$ to $C_6$ alkyl, $C_1$ to $C_4$ haloalkyl, ($C_3$ to $C_6$ cycloalkyl)methyl, $C_3$ to $C_6$ cycloalkyl, $CH_2CO_2R^{10}$, ($C_2$ to $C_4$ alkenyl)methyl, ($C_2$ to $C_4$ haloalkenyl)methyl, $CH_2SCH_3$, $CH_2OCH_3$, ($C_2$ to $C_4$ alkynyl)methyl, $C(O)R^{12}$, $C(O)(C_1$ to $C_4$ haloalkyl), CHO, $C(O)NH_2$, $CO_2R^{12}$, $C(O)NHR^{12}$, phenyl or benzyl each optionally substituted with $NO_2$, CN or 1 to 3 halogens;
$R^2$ is H, $C_1$ to $C_4$ alkyl, $C_1$ to $C_4$ haloalkyl, cyclopropyl, $CH_2CN$, $CO_2R^{11}$, CHO, $CH_2OH$, CN, $C_2$ to $C_4$ alkenyl or $C_2$ to $C_4$ alkynyl;
$R^3$ is pyridylmethyl, thienylmethyl, phenylmethyl, benzylmethyl, phenoxymethyl or thiophenoxymethyl each substituted with $R^8$ and $R^9$ on the aromatic radical and with $R^{16}$ and $R^{17}$ on the aliphatic carbon, phenyl substituted with $R^8$ and $R^9$, $C_1$ to $C_4$ alkyl, $C_1$ to $C_4$ haloalkyl, $C_3$ to $C_6$ cycloalkyl, thienyl optionally substituted with 1 to 2 halogen, styryl substituted with $R^8$ and $R^9$, ($C_3$ to $C_6$ cycloalkyl)methyl, ($C_3$ to $C_6$ cycloalkyl)ethyl, pyrimidine or pyridine each substituted with $R^8$ and $R^9$;
$R^4$ is phenyl substituted with $R^8$ and $R^9$, benzyl substituted with $R^8$ and $R^9$, $C_3$ to $C_6$ cycloalkyl, thienyl optionally substituted with 1 to 2 halogen, styryl substituted with $R^8$ and $R^9$, pyridine or pyrimidine each substituted with $R^8$ and $R^9$, ($C_3$ to $C_6$ cycloalkyl)methyl, ($C_3$ to $C_6$ cycloalkyl)ethyl, $OR^{13}$, $SR^{13}$, or $N(R^{14})(R^{15})$;
$R^5$ is H or halogen;
$R^6$ is H, halogen, methyl, $CF_3$ or $OCH_3$;
$R^7$ is H, halogen, $C_1$ to $C_4$ alkyl, $C_1$ to $C_4$ haloalkyl, $C_1$ to $C_2$ alkoxy, CN, $CO_2R^{12}$, $NO_2$, $S)O)_mCH_3$, phenyl optionally substituted with 1 to 3 halogens, or phenoxy optionally substituted with 1 to 3 halogen;
m is 0, 1 or 2;
$R^8$ is H or halogen;
$R^9$ is H, halogen, methyl, $CF_3$, $OCH_3$, CN or $CO_2R^{12}$;
$R^{10}$ is H, $C_1$ to $C_6$ alkyl, benzyl optionally substituted with 1 to 3 halogen, or phenyl optionally substituted with 1 to 3 halogen;
$R^{11}$ is H or $C_1$ to $C_3$ alkyl;
$R^{12}$ is $C_1$ to $C_4$ alkyl;
$R^{13}$ is $C_1$ to $C_5$ alkyl, ($C_2$ to $C_4$ alkenyl)methyl, ($C_2$ to $C_4$ alkynyl)methyl, phenyl substituted with $R^8$ and $R^9$, benzyl substituted with $R^8$ and $R^9$, $C_3$ to $C_7$ cycloalkyl, ($C_3$ to $C_7$ cycloalkyl)methyl or $C_1$ to $C_5$ haloalkyl;
$R^{14}$ is H or $R^{13}$;
$R^{15}$ is H, $C_1$ to $C_4$ alkyl, ($C_2$ to $C_4$ alkenyl)methyl or ($C_2$ to $C_4$ alkynyl)methyl; or $R^{14}$ and $R^{15}$ may together form a 5- or 6-membered saturated heterocycle which contains the amine nitrogen and is selected from the group of pyrrolidino, and morpholino;

$R^{16}$ is H, halogen, $CF_3$, OH, $C_1$ to $C_3$ alkyl, $C_1$ to $C_3$ alkoxy or $C_1$-$C_3$ alkylthio;

$R^{17}$ is H, F, Cl or $CH_3$;

$R^{18}$ is $C_1$-$C_4$ alkyl, $CH_2CN$; $CH_2SCN$;

and their agriculturally suitable salts, provided that a) when $R^2$ or $R^3$ is $CF_3$ then the other is not n-butyl;

b) when $R^3$ is phenoxymethyl or thiophenoxymethyl then $R^{17}$ and $R^{17}$ are other than Br, I, Cl or OH.

2. The compounds of claim 1 wherein:

Q is H;

$R^1$ is H, $C_1$ to $C_3$ alkyl, allyl or propargyl;

$R^2$ is H, $C_1$ to $C_3$ alkyl, CN or $C_2$ to $C_3$ alkenyl;

$R^3$ is phenyl substituted with $R^8$ and $R^9$; phenylmethyl, pyridylmethyl, phenoxymethyl, thiophenoxymethyl or thienylmethyl each substituted with $R^8$ and $R^9$ on the aryl radical and $R^{16}$ and $R^{17}$ on the aliphatic carbon;

$R^{15}$ is $C_1$ to $C_4$ alkyl, ($C_2$ to $C_4$ alkenyl)methyl, or ($C_2$ to $C_4$ alkynyl)methyl; and $R^4$ is phenyl substituted with $R^8$ and $R^9$, benzyl substituted with $R^8$ and $R^9$, $C_3$ to $C_6$ cycloalkyl, thienyl optionally substituted with 1 to 2 halogen, styryl substituted with $R^8$ and $R^9$, pyridine substituted with $R^8$ and $R^9$, ($C_3$ to $C_6$ cycloalkyl)methyl or ($C_3$ to $C_6$ cycloalkyl)ethyl.

3. The compounds of claim 2 wherein:

$R^5$ is H, F or Cl;

$R^6$ is F, Cl, $CH_3$ or $CF_3$;

$R^7$ is halogen, $CH_3$, $OCH_3$, CN, phenyl optionally substituted with 1 to 3 halogens or phenoxy optionally substituted with 1 to 3 halogens;

$R^8$ is H, F, Cl;

$R^9$ is H, F or Cl.;

$R^{16}$ is H, F, Cl or $C_1$ to $C_2$ alkyl; and $R^{17}$ is H.

4. The compounds of claim 3 wherein:

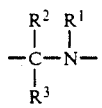

$R^1$ is H or $CH_3$;

$R^2$ is H or $CH_3$;

$R^3$ is phenyl or phenylmethyl optionally substituted with 1 to 3 F or Cl and optionally substituted on alkyl with H or $CH_3$;

$R^7$ is H, F, Cl, $CH_3$, $OCH_3$ or $C_6H_5$; and

Ar is phenyl, or wherein

and $R^4$ is phenyl substituted with $R^8$ and $R^9$.

5. The compound of claim 1 which is N-[(2,4-dichlorophenyl)(4-fluorophenyl)methyl]-N-methyl-1H-1,2,4-triazol-1-amine.

6. The compound of claim 1 which is N-[(2,4-dichlorophenyl)(4-fluorophenyl)methyl]-1H-1,2,4-triazol-1-amine.

7. The compound of claim 1 which is N-[bis-(4-fluorophenyl)methyl]-N-methyl-1H-1,2,4-triazol-1-amine.

8. The compound of claim 1 which is N-[bis-(4-fluorophenyl)methyl]-1H-1,2,4-triazol-1-amine.

9. The compound of claim 1 which is N-[(2,4-dichlorophenyl)(4-fluorophenyl)methylene]-1H-1,2,4-triazole-1-amine.

10. The compound of claim 1 which is 1H-1,2,4-triazol-1-amine, N-((1-(2,4-dichlorophenyl)-2-(4-fluorophenyl)propyl).

11. The compound of claim 1 which is 1H-1,2,4-triazol-1-amine, N-(((4-cyano-phenyl)(2,4-dichlorophenyl)methyl))-N-methyl.

12. The compound of claim 1 which is 1H-1,2,4-triazol-1-amine, N-((2-(4-chloro-phenyl)-1-(2,4-difluorophenyl)propyl)).

13. The compound of claim 1 which is 1H-1,2,4-triazol-1-amine, N-((1-(2,4-difluorophenyl)-2-(4-fluorophenyl)propyl)).

14. A composition for controlling fungus disease which comprises an effective amount of a compound of claim 1 and at least one of the following: surfactant, solid or liquid inert diluent.

15. A composition for controlling fungus disease which comprises an effective amount of a compound of claim 2 and at least one of the following: surfactant, solid or liquid inert diluent.

16. A composition for controlling fungus disease which comprises an effective amount of a compound of claim 3 and at least one of the following: surfactant, solid or liquid inert diluent.

17. A composition for controlling fungus disease which comprises an effective amount of a compound of claim 4 and at least one of the following: surfactant, solid or liquid inert diluent.

18. A composition for controlling fungus disease which comprises an effective amount of a compound of claim 5 and at least one of the following: surfactant, solid or liquid inert diluent.

19. A composition for controlling fungus disease which comprises an effective amount of a compound of claim 6 and at least one of the following: surfactant, solid or liquid inert diluent.

20. A composition for controlling fungus disease which comprises an effective amount of a compound of claim 7 and at least one of the following: surfactant, solid or liquid inert diluent.

21. A composition for controlling fungus disease which comprises an effective amount of a compound of claim 8 and at least one of the following: surfactant, solid or liquid inert diluent.

22. A composition for controlling fungus disease which comprises an effective amount of a compound of claim 9 and at least one of the following: surfactant, solid or liquid inert diluent.

23. A composition for controlling fungus disease which comprises an effective amount of a compound of claim 10 and at least one of the following: surfactant, solid or liquid inert diluent.

24. A composition for controlling fungus disease which comprises an effective amount of a compound of claim 11 and at least one of the following: surfactant, solid or liquid inert diluent.

25. A composition for controlling fungus disease which comprises an effective amount of the compound of claim 12 and at least one of the following: surfactant, solid or liquid inert diluent.

26. A composition for controlling fungus disease which comprises an effective amount of the compound of claim 13 and at least one of the following: surfactant, solid or liquid inert diluent.

27. A method for controlling fungus disease which comprises applying to the locus of infestation to be protected an effective amount of a compound of claim 1.

28. A method for controlling fungus disease which comprises applying to the locus of infestation to be protected an effective amount of a compound of claim 2.

29. A method for controlling fungus disease which comprises applying to the locus of infestation to be protected an effective amount of a compound of claim 3.

30. A method for controlling fungus disease which comprises applying to the locus of infestation to be protected an effective amount of a compound of claim 4.

31. A method for controlling fungus disease which comprises applying to the locus of infestation to be protected an effective amount of a compound of claim 5.

32. A method for controlling fungus disease which comprises applying to the locus of infestation to be protected an effective amount of a compound of claim 6.

33. A method for controlling fungus disease which comprises applying to the locus of infestation to be protected an effective amount of a compound of claim 7.

34. A method for controlling fungus disease which comprises applying to the locus of infestation to be protected an effective amount of a compound of claim 8.

35. A method for controlling fungus disease which comprises applying to the locus of infestation to be protected an effective amount of a compound of claim 9.

36. A method for controlling fungus disease which comprises applying to the locus of infestation to be protected an effective amount of a compound of claim 10.

37. A method for controlling fungus disease which comprises applying to the locus of infestation to be protected an effective amount of a compound of claim 11.

38. A method for controlling fungus disease which comprises applying to the locus of infestation to be protected an effective amount of the compound of claim 12.

39. A method for controlling fungus disease which comprises applying to the locus of infestation to be protected an effective amount of the compound of claim 13.

* * * * *